US011344605B2

(12) United States Patent
Kallikourdis et al.

(10) Patent No.: US 11,344,605 B2
(45) Date of Patent: May 31, 2022

(54) THERAPEUTIC USE OF INHIBITORS OF T CELL ACTIVATION OR STIMULATION

(71) Applicant: Humanitas Mirasole S.p.A., Milan (IT)

(72) Inventors: Marinos Kallikourdis, Milan (IT); Gianluigi Condorelli, Milan (IT)

(73) Assignee: Humanitas Mirasole S.p.A., Milan (IT)

( * ) Notice: Subject to any disclaimer, the term of this patent is extended or adjusted under 35 U.S.C. 154(b) by 0 days.

(21) Appl. No.: 16/069,676

(22) PCT Filed: Sep. 27, 2016

(86) PCT No.: PCT/EP2016/072934
§ 371 (c)(1),
(2) Date: Jul. 12, 2018

(87) PCT Pub. No.: WO2017/121502
PCT Pub. Date: Jul. 20, 2017

(65) Prior Publication Data
US 2020/0164031 A1 May 28, 2020

(30) Foreign Application Priority Data
Jan. 15, 2016 (EP) .................................... 16151539

(51) Int. Cl.
*C07K 14/705* (2006.01)
*A61K 38/17* (2006.01)
*A61P 9/00* (2006.01)
*A61P 9/04* (2006.01)
*C07K 16/28* (2006.01)
*A61K 39/00* (2006.01)
*A61K 48/00* (2006.01)

(52) U.S. Cl.
CPC .. *A61K 38/1774* (2013.01); *A61K 39/001102* (2018.08); *A61P 9/04* (2018.01); *C07K 14/705* (2013.01); *C07K 16/2827* (2013.01); *A61K 48/00* (2013.01); *C07K 2319/30* (2013.01); *C07K 2319/32* (2013.01)

(58) Field of Classification Search
None
See application file for complete search history.

(56) References Cited

U.S. PATENT DOCUMENTS

2005/0123539 A1* 6/2005 Rusnak ............. C07K 16/2818
424/144.1
2013/0323258 A1* 12/2013 Burton ....................... A61P 7/04
424/139.1

FOREIGN PATENT DOCUMENTS

RU       2014102956 A    8/2015
WO   WO 2011/103584 A2   8/2011

OTHER PUBLICATIONS

Chen L, et al. Nat Rev Immunol. 2013, 13(4):227-242.*
Palmer CS, et al. Int Rev Immunol. 2016, 35(6):477-488.*
Skalniak et al. Oncotarget, 2017, vol. 8, (No. 42), pp. 72167-72181.*
Aqel et al. (2019) Clinical and Experimental Immunology, 196: 215-225.*
Abe et al., Prevention of experimental autoimmune myocarditis by hydrodynamics-based naked plasmid DNA encoding CTLA4-Ig gene delivery. J Card Fail. Sep. 2005;11(7):557-64.
Ancey et al., Secretion of IL-6, IL-11 and LIF by human cardiomyocytes in primary culture. Cytokine. May 21, 2002;18(4):199-205.
Bluestone, Is CTLA-4 a master switch for peripheral T cell tolerance? J Immunol. Mar. 1, 1997;158(5):1989-93.
Bulut et al., The number of regulatory T cells correlates with hemodynamic improvement in patients with inflammatory dilated cardiomyopathy after immunoadsorption therapy. Scand J Immunol. Jan. 2013;77(1):54-61. doi: 10.1111/sji.12000.
Condorelli et al., Akt induces enhanced myocardial contractility and cell size in vivo in transgenic mice. Proc Natl Acad Sci U S A. Sep. 17, 2002;99(19):12333-8.
Condorelli et al., Heart-targeted overexpression of caspase3 in mice increases infarct size and depresses cardiac function. Proc Natl Acad Sci U S A. Aug. 14, 2001;98(17):9977-82. Epub Aug. 7, 2001.
Condorelli et al., Increased cardiomyocyte apoptosis and changes in proapoptotic and antiapoptotic genes bax and bcl-2 during left ventricular adaptations to chronic pressure overload in the rat. Circulation. Jun. 15, 1999;99(23):3071-8.
Dhirapong et al., Therapeutic effect of CTLA4-Ig on a murine model of primary biliary cirrhosis. Hepatology. Feb. 2013; 57(2): 708-715. doi: 10.1002/hep.26067. Author Manuscript.
Epelman et al., Embryonic and adult-derived resident cardiac macrophages are maintained through distinct mechanisms at steady state and during inflammation. Immunity. Jan. 16, 2014;40(1):91-104. doi: 10.1016/j.immuni.2013.11.019.
Garetto et al. Peak inflammation in atherosclerosis, primary biliary cirrhosis and autoimmune arthritis is counter-intuitively associated with regulatory T cell enrichment. Immunobiology. Aug. 2015;220(8):1025-9. doi: 10.1016/j.imbio.2015.02.006. Epub Feb. 26, 2015.
Han et al., CTLA4-Ig relieves inflammation in murine models of coxsackievirus B3-induced myocarditis. Can J Cardiol. Mar.-Apr. 2012;28(2):239-44. doi: 10.1016/j.cjca.2011.11.014. Epub Feb. 14, 2012.
Hofmann et al., How can we cure a heart "in flame"? A translational view on inflammation in heart failure. Basic Res Cardiol. Jul. 2013;108(4):356. doi: 10.1007/s00395-013-0356-y. Epub Jun. 6, 2013.
Kanellakis et al., CD4+CD25+Foxp3+ regulatory T cells suppress cardiac fibrosis in the hypertensive heart. J Hypertens. Sep. 2011;29(9):1820-8. doi: 10.1097/HJH.0b013e328349c62d.
Kemi et al., Activation or inactivation of cardiac Akt/mTOR signaling diverges physiological from pathological hypertrophy. J Cell Physiol. Feb. 2008;214(2):316-21.

(Continued)

Primary Examiner — Ilia I Ouspenski
(74) Attorney, Agent, or Firm — Wolf, Greenfield & Sacks, P.C.

(57) ABSTRACT

The present invention relates to the use of inhibitors of T cell costimulation and/or activation and/or function in the treatment and/or prevention of cardiac pathologies, in particular heart failure diseases, and/or of related symptoms.

17 Claims, 40 Drawing Sheets

Figure 1A:
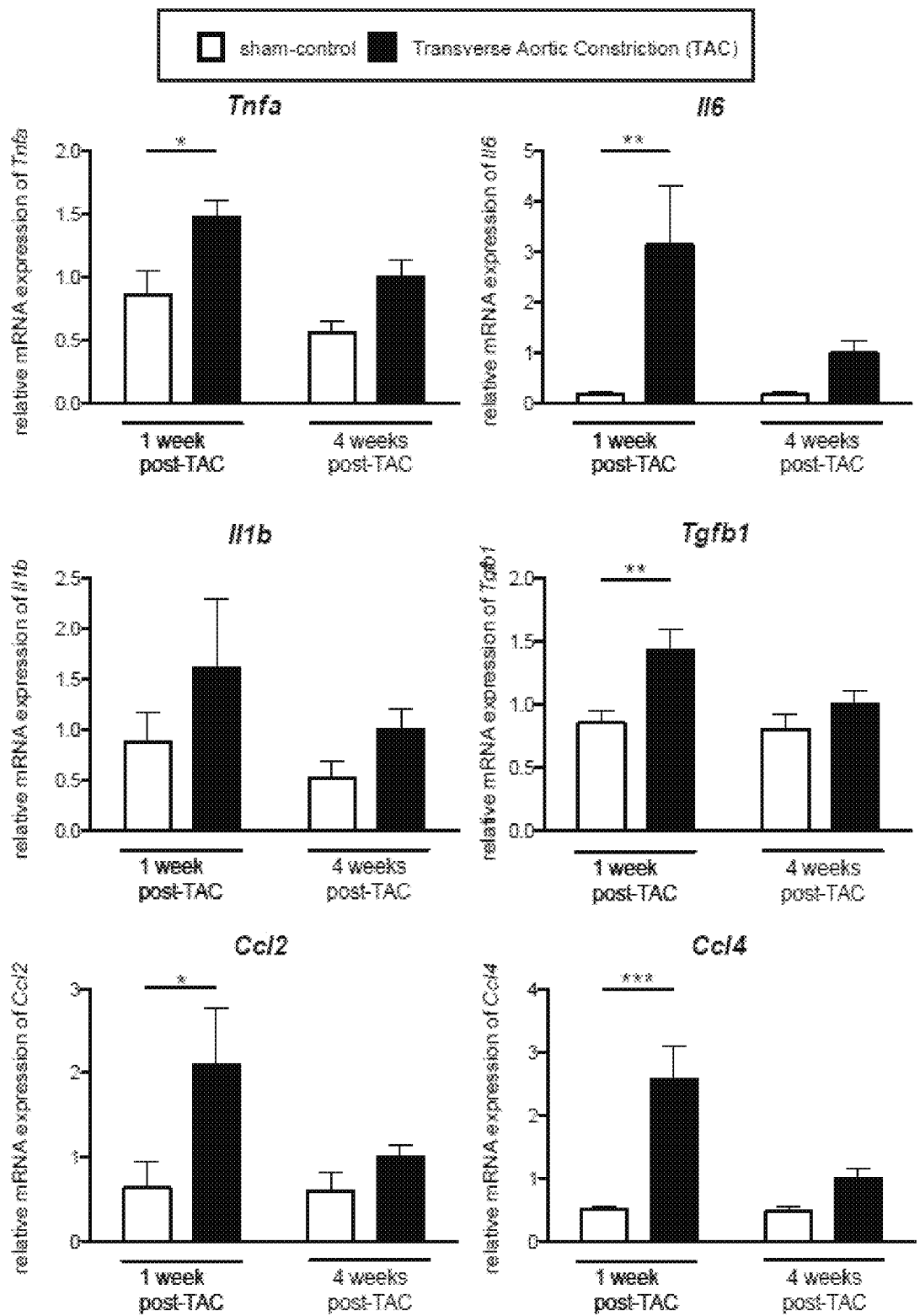

Specification includes a Sequence Listing.

(56) References Cited

OTHER PUBLICATIONS

Ko et al., CTLA4-Ig modifies dendritic cells from mice with collagen-induced arthritis to increase the CD4+CD25+Foxp3+ regulatory T cell population. J Autoimmun. Mar. 2010;34(2):111-20. doi: 10.1016/j.jaut.2009.07.006. Epub Aug. 8, 2009.

Kong et al., The pathogenesis of cardiac fibrosis. Cell Mol Life Sci. Feb. 2014;71(4):549-74. doi: 10.1007/s00018-013-1349-6. Epub May 7, 2013.

Krummey et al., Braking bad: novel mechanisms of CTLA-4 inhibition of T cell responses. Am J Transplant. Dec. 2014;14(12):2685-90. doi: 10.1111/ajt.12938. Epub Nov. 11, 2014.

Kuang et al., Aortic Remodeling Following Transverse Aortic Constriction in Mice is Attenuated with AT1 Receptor Blockade. Arterioscler Thromb Vasc Biol. Sep. 2013; 33(9): 2172-2179. Epub Jul. 18, 2013. doi: 10.1161/ATVBAHA.113.301624.

Kvakan et al., Regulatory T cells ameliorate angiotensin II-induced cardiac damage. Circulation. Jun. 9, 2009;119(22):2904-12. doi: 10.1161/CIRCULATIONAHA.108.832782. Epub May 26, 2009.

Lai et al., Pressure overload-induced cardiac remodeling and dysfunction in the absence of interleukin 6 in mice. Lab Invest. Nov. 2012;92(11):1518-26. doi: 10.1038/labinvest.2012.97. Epub Jul. 23, 2012.

Laroumanie et al. CD4+ T cells promote the transition from hypertrophy to heart failure during chronic pressure overload. Circulation. May 27, 2014;129(21):2111-24. doi: 10.1161/CIRCULATIONAHA.113.007101. Epub Mar. 21, 2014.

Linsley et al., CTLA-4 is a second receptor for the B cell activation antigen B7. J Exp Med. Sep. 1, 1991; 174(3): 561-569. doi: 10.1084/jem.174.3.561.

Loke et al., Alternative activation is an innate response to injury that requires CD4+ T cells to be sustained during chronic infection. J Immunol. Sep. 15, 2007;179(6):3926-36.

Mann, Inflammatory mediators and the failing heart: past, present, and the foreseeable future. Circ Res. Nov. 29, 2002;91(11):988-98.

Mantovani et al., The chemokine system in diverse forms of macrophage activation and polarization. Trends Immunol. Dec. 2004;25(12):677-86.

Meléndez et al., Interleukin 6 mediates myocardial fibrosis, concentric hypertrophy, and diastolic dysfunction in rats. Hypertension. Aug. 2010;56(2):225-31. doi: 10.1161/HYPERTENSIONAHA.109.148635. Epub Jul. 6, 2010.

Moreland et al., Abatacept. Nat Rev Drug Discov. Mar. 2006;5(3):185-6. doi: 10.1038/nrd1989.

Nevers et al., Left Ventricular T-Cell Recruitment Contributes to the Pathogenesis of Heart Failure. Circ Heart Fail. Jul. 2015;8(4):776-87. doi: 10.1161/CIRCHEARTFAILURE.115.002225. Epub May 28, 2015.

Niedermeier et al., CD4+ T cells control the differentiation of Gr1+ monocytes into fibrocytes. Proc Natl Acad Sci U S A. Oct. 20, 2009;106(42):17892-7. doi: 10.1073/pnas.0906070106. Epub Oct. 6, 2009.

Oka et al., Mitochondrial DNA that escapes from autophagy causes inflammation and heart failure. Nature. May 10, 2012;485(7397):251-5. doi: 10.1038/nature10992. Erratum in: Nature. Oct. 11, 2012;490(7419):292.

Peng et al., Angiotensin II-induced dilated cardiomyopathy in Balb/c but not C57BL/6J mice. Exp Physiol. Aug. 2011;96(8):756-64. doi: 10.1113/expphysiol.2011.057612. Epub May 20, 2011.

Perrino et al., Intermittent pressure overload triggers hypertrophy-independent cardiac dysfunction and vascular rarefaction. J Clin Invest. Jun. 2006;116(6):1547-60.

Pieper et al., CTLA4-Ig (abatacept) therapy modulates T cell effector functions in autoantibody-positive rheumatoid arthritis patients. BMC Immunol. Aug. 5, 2013;14:34. doi: 10.1186/1471-2172-14-34. 9 pages.

Pilat et al., Modulating T-cell costimulation as new immunosuppressive concept in organ transplantation. Curr Opin Organ Transplant. Aug. 2012;17(4):368-75. doi: 10.1097/MOT.0b013e328355fc94.

Roncarati et al., Doubly heterozygous LMNA and TTN mutations revealed by exome sequencing in a severe form of dilated cardiomyopathy. Eur J Hum Genet. Oct. 2013;21(10):1105-11. doi: 10.1038/ejhg.2013.16. Epub Mar. 6, 2013.

Sage et al., The coinhibitory receptor CTLA-4 Controls B cell Responses by Modulating T Follicular Helper, T Follicular Regulatory and T Regulatory Cells. Immunity. Dec. 18, 2014; 41(6): 1026-1039. EPub Dec. 5, 2014. doi: 10.1016/j.immuni.2014.12.005.

Serra et al., Exercise training inhibits inflammatory cytokines and more than prevents myocardial dysfunction in rats with sustained β-adrenergic hyperactivity. J Physiol. Jul. 1, 2010; 588(Pt 13):2431-2442. EPub May 4, 2010. doi: 10.1113/jphysiol.2010.187310.

Sharpe, Mechanisms of costimulation. Immunol Rev. May 2009;229(1):5-11. doi: 10.1111/j.1600-065X.2009.00784.x.

Shioi et al., Increased expression of interleukin-1 beta and monocyte chemotactic and activating factor/monocyte chemoattractant protein-1 in the hypertrophied and failing heart with pressure overload. Circ Res. 1997;81(5):664-671. doi:10.1161/01.res.81.5.664.

Souders et al., Pressure overload induces early morphological changes in the heart. Am J Pathol. 2012;181(4):1226-1235. doi:10.1016/j.ajpath.2012.06.015.

Stølen et al., Interval training normalizes cardiomyocyte function, diastolic Ca2+ control, and SR Ca2+ release synchronicity in a mouse model of diabetic cardiomyopathy. Circ Res. 2009;105(6):527-536. doi:10.1161/CIRCRESAHA.109.199810.

Suntharalingam et al., Cytokine storm in a phase 1 trial of the anti-CD28 monoclonal antibody TGN1412. N Engl J Med. 2006;355(10):1018-1028. doi:10.1056/NEJMoa063842.

Tang et al., Defective circulating CD4+CD25+Foxp3+CD127(low) regulatory T-cells in patients with chronic heart failure. Cell Physiol Biochem. 2010;25(4-5):451-458. doi:10.1159/000303050.

Tang et al., Regulatory T cells ameliorate cardiac remodeling after myocardial infarction. Basic Res Cardiol. 2012;107(1):232. doi:10.1007/s00395-011-0232-6.

Tian et al., Inhibition of AIF-1 expression by constitutive siRNA expression reduces macrophage migration, proliferation, and signal transduction initiated by atherogenic stimuli. Am J Physiol Cell Physiol. 2006;290(4):C1083-C1091. doi:10.1152/ajpcell.00381.2005.

Utans et al., Cloning and characterization of allograft inflammatory factor-1: a novel macrophage factor identified in rat cardiac allografts with chronic rejection. J Clin Invest. 1995;95(6):2954-2962. doi:10.1172/JCI118003.

Verma et al., IL 10 Treatment Attenuates Pressure Overload-Induced Hypertrophic Remodeling and Improves Heart Function via STAT3 Dependent Inhibition of NFκB. Circulation. Jul. 24, 2012; 126(4): 418-429. EPub Jun. 15, 2012. doi: 10.1161/CIRCULATIONAHA.112.112185. Author Manuscript.

Weirather et al., Foxp3+ CD4+ T cells improve healing after myocardial infarction by modulating monocyte/macrophage differentiation. Circ Res. 2014;115(1):55-67. doi:10.1161/CIRCRESAHA.115.303895.

Wing et al., Regulatory T cells exert checks and balances on self tolerance and autoimmunity. Nat Immunol. 2010;11(1):7-13. doi:10.1038/ni.1818.

Wynn, Fibrotic disease and the $T_H1/T_H2$ paradigm. Nat Rev Immunol. Aug. 2004; 4(8): 583-594. doi: 10.1038/nril412. Author Manuscript.

Ying, Characterization of the Inflammatory and Fibrotic Response in a Mouse Model of Cardiac Pressure Overload. Histochem Cell Biol. Apr. 2009; 131(4): 471-481. EPub Nov. 22, 2008. doi: 10.1007/s00418-008-0541-5. Author Manuscript.

Yndestad et al., Systemic inflammation in heart failure—the whys and wherefores. Heart Fail Rev. Mar. 2006;11(1):83-92.

Yu et al., Role of T lymphocytes in hypertension-induced cardiac extracellular matrix remodeling. Hypertension. 2006;48(1):98-104. doi:10.1161/01.HYP.0000227247.27111.b2.

Zarrinkoub et al., The epidemiology of heart failure, based on data for 2.1 million inhabitants in Sweden. Eur J Heart Fail. 2013;15(9):995-1002. doi:10.1093/eurjhf/hft064.

PCT/EP2016/072934, Nov. 21, 2016, International Search Report and Written Opinion.

(56) References Cited

OTHER PUBLICATIONS

PCT/EP2016/072934, Jul. 26, 2018, International Preliminary Report on Patentability.

Couzin-Frankel, Breakthrough of the year 2013. Cancer immunotherapy. Science. 2013;342(6165):1432-1433. doi:10.1126/science.342.6165.1432.

Fischer et al., Gene therapy of primary T cell immunodeficiencies. Gene. 2013;525(2):170-173. doi:10.1016/j.gene.2013.03.092.

Peterson, Pressure overload hypertrophy and congestive heart failure. Where is the "Achilles heel"?. J Am Coll Cardiol. 2002;39(4):672-675. doi:10.1016/s0735-1097(01)01790-9.

Sowndramalingam et al., Cardiac energy metabolic alterations in pressure overload-induced left and right heart failure (2013 Grover Conference Series). Pulm Circ. 2015;5(1):15-28. doi: 10.1086/679608.

Takeishi et al., Src and multiple MAP kinase activation in cardiac hypertrophy and congestive heart failure under chronic pressure-overload: comparison with acute mechanical stretch. J Mol Cell Cardiol. 2001;33(9):1637-1648. doi:10.1006/jmcc.2001.1427.

Vinh et al., Inhibition and genetic ablation of the B7/CD28 T-cell costimulation axis prevents experimental hypertension. Circulation. 2010;122(24):2529-2537. doi:10.1161/CIRCULATIONAHA.109.930446.

Martini et al., T Cell Costimulation Blockade Blunts Age-Related Heart Failure. Circ Res. Sep. 25, 2020;127(8):1115-1117. doi: 10.1161/CIRCRESAHA.119.316530. Epub Aug. 17, 2020.

Picchianti Diamanti et al., Abatacept (cytotoxic T lymphocyte antigen 4-immunoglobulin) improves B cell function and regulatory T cell inhibitory capacity in rheumatoid arthritis patients non-responding to anti-tumour necrosis factor-α agents. Clin Exp Immunol. Sep. 2014;177(3):630-40. doi: 10.1111/cei.12367.

Promislow et al., Pulmonary arterial hypertension associated with abatacept treatment for rheumatoid arthritis: A case report. Can J Resp Crit Care Sleep Med. 2018;2(1):41-44. doi: 10.1080/24745332.2017.1387507.

Schiattarella, Declaration filed in Application No. EP 16775169.2. Feb. 4, 2021. 2 pages.

Torella, Declaration filed in Application No. EP 16775169.2. Mar. 5, 2021. 1 page.

Raphael et al., Limitations of the New York Heart Association functional classification system and self-reported walking distances in chronic heart failure. Heart. Apr. 2007;93(4):476-82. doi: 10.1136/hrt.2006.089656. Epub Sep. 27, 2006.

* cited by examiner

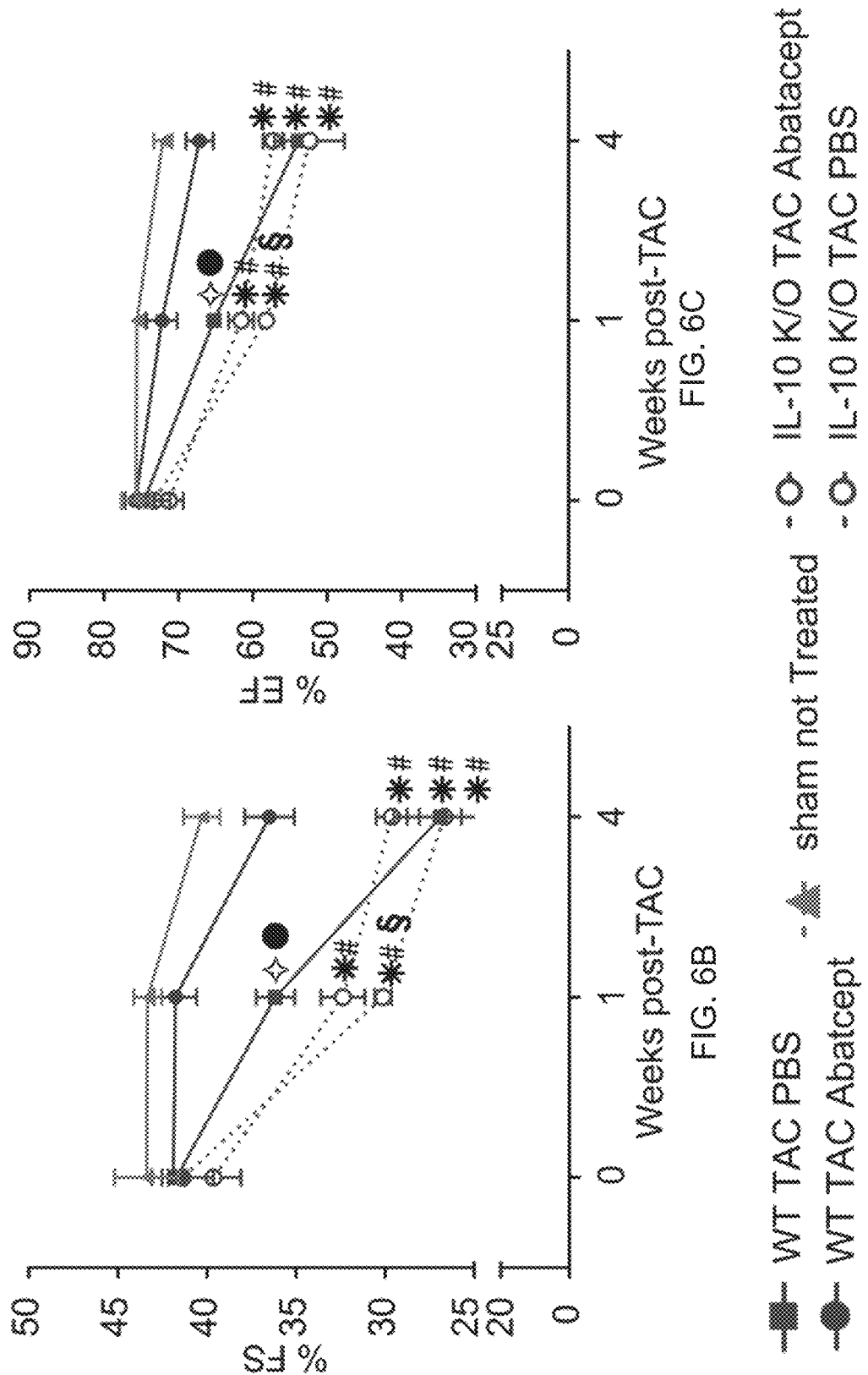

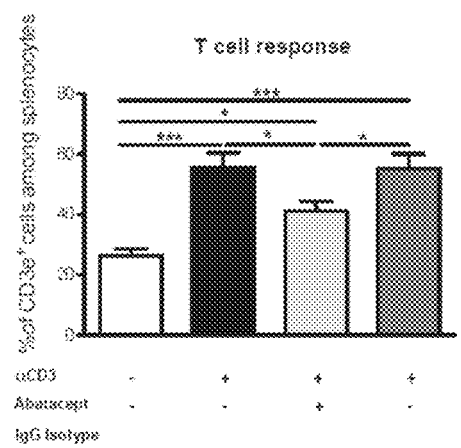 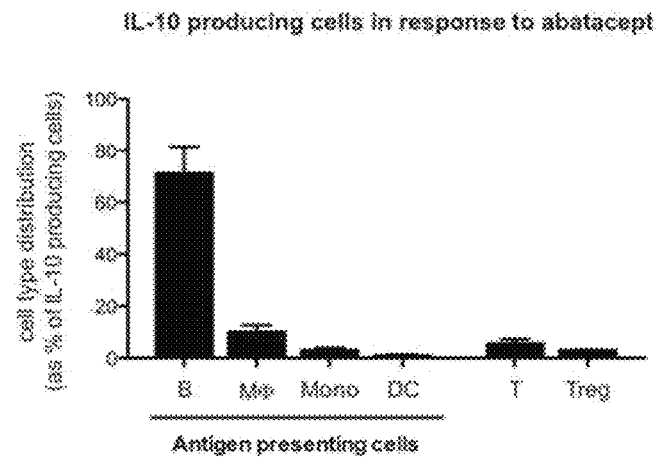
FIG. 11A FIG. 11B
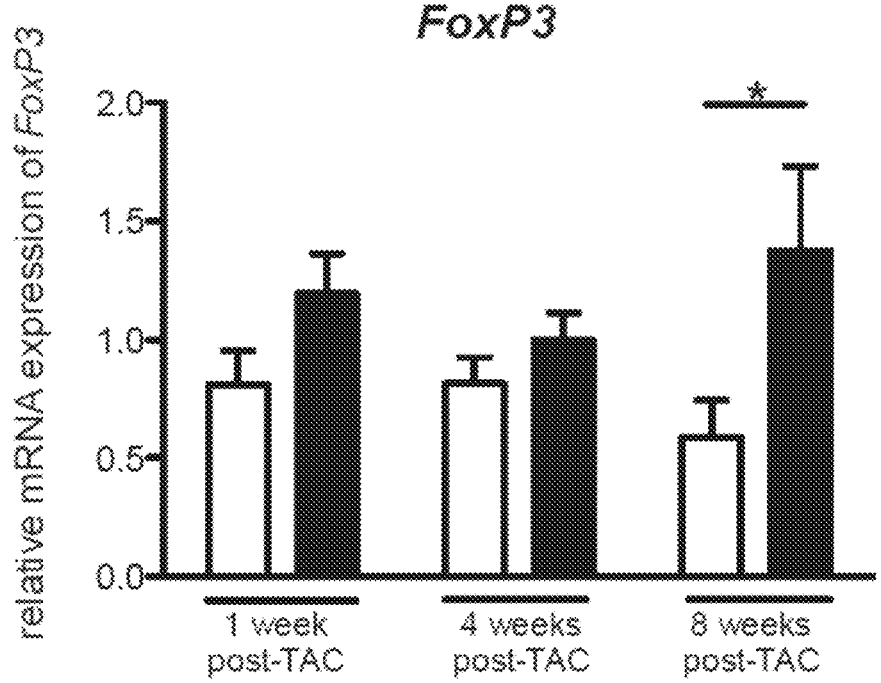
FIG. 12

SEQUENCE LISTING

<160> NUMBER OF SEQ ID NOS: 10

<210> SEQ ID NO 1
<211> LENGTH: 357
<212> TYPE: PRT
<213> ORGANISM: Artificial Sequence
<220> FEATURE:
<223> OTHER INFORMATION: CTLA4-Ig

<400> SEQUENCE: 1

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
```

-continued

```
                355

<210> SEQ ID NO 2
<211> LENGTH: 383
<212> TYPE: PRT
<213> ORGANISM: Artificial Sequence
<220> FEATURE:
<223> OTHER INFORMATION: CTLA4-Ig

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
```

His Asn His Tyr Thr Gln Lys Ser Leu Ser Leu Ser Pro Gly Lys
            370                 375                 380

<210> SEQ ID NO 3
<211> LENGTH: 18
<212> TYPE: DNA
<213> ORGANISM: Artificial Sequence
<220> FEATURE:
<223> OTHER INFORMATION: synthetic primer

<400> SEQUENCE: 3
cgcatcaagg agctcacc                                                 18

<210> SEQ ID NO 4
<211> LENGTH: 18
<212> TYPE: DNA
<213> ORGANISM: Artificial Sequence
<220> FEATURE:
<223> OTHER INFORMATION: synthetic primer

<400> SEQUENCE: 4
ctgcagccgc agtaggtt                                                 18

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
gtcagtcgtt tgggctgtaa c                                             21

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
agacccaggc agagtcagaa                                               20

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
cacagatctg atggatttca aga                                           23

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
cctcatcttc taccggcatc                                               20

<210> SEQ ID NO 9

```
<211> LENGTH: 24
<212> TYPE: DNA
<213> ORGANISM: Artificial Sequence
<220> FEATURE:
<223> OTHER INFORMATION: synthetic primer

<400> SEQUENCE: 9
aaatcagtta tggttccttt ggtc                                          24

<210> SEQ ID NO 10
<211> LENGTH: 26
<212> TYPE: DNA
<213> ORGANISM: Artificial Sequence
<220> FEATURE:
<223> OTHER INFORMATION: synthetic primer

<400> SEQUENCE: 10
gctctagaat taccacagtt atccaa                                        26
```

THERAPEUTIC USE OF INHIBITORS OF T CELL ACTIVATION OR STIMULATION

RELATED APPLICATION

This application is a national stage filing under 35 U.S.C. § 371 of International Patent Application Ser. No. PCT/EP2016/072934, filed Sep. 27, 2016, the contents of which is incorporated herein by reference in its entirety.

This application claims priority from European patent application no. 16151539.0, filed in the name of HUMANITAS MIRASOLE S. P. A. on Jan. 15, 2016, which is hereby incorporated by reference in its entirety. All documents cited herein are incorporated herein by reference in their entirety.

BACKGROUND ART

Heart failure (HF) is a major cause of hospitalization, morbidity, and mortality; it is often encountered as the final stage of pathological cardiac hypertrophy and fibrosis brought about by hemodynamic overload (Zarrinkoub et al., 2013). Some forms of cardiomyopathy—termed inflammatory cardiomyopathies—are caused by autoimmunity or by immune responses to infection, indicating that cardiac dysfunction can also result from disease of the immune system (Bulut et al., 2012). Intriguingly, recent studies have uncovered that HF induced by hemodynamic overload also involves a significant inflammatory component (Shioi et al., 1997) (Oka et al., 2012) (Hofmann and Frantz, 2013). This inflammation is characterized by the presence in the myocardium of cells of the innate immune system (macrophages) and upregulation of pro-inflammatory cytokines, such as TNFα, IL-6, and IL-1β, which impact negatively on disease outcome (Shioi et al., 1997) (Ancey et al., 2002) (Souders et al., 2012). Even though its congenic absence can be compensated (Lai et al., 2012), IL-6 administration is sufficient to set off the process leading to pathological cardiac hypertrophy (Melendez et al., 2010). It is believed that the innate immune cells and cytokines promote inflammation in the heart, worsening the disease outcome. Although the concept of inflammation as a major component of HF is consolidated (Mann, 2002), clinical trials attempting to combat HF by blocking cytokines have not been successful (Yndestad et al., 2006) (Hofiiiann and Frantz, 2013). The reason for this failure could be the redundant function of individual cytokines (Lai et al., 2012). Therefore, in order to identify more suitable immunotherapy targets for HF, we need to better characterize the involvement and hierarchy of different soluble immune mediators and of the cells of the innate and the adaptive immune system in the disease.

The innate immune system acts via the production of cytokines as a non-specific, but effective and rapid, line of defense against pathogens. During long-lasting responses, however, it becomes subject to the control of the adaptive immune system's T lymphocytes (T cells) (Loke et al., 2007), which, along with B cells, mediate antigen-specific immune responses. Therefore, T cells, if involved in HF pathogenesis, could become attractive and more specific immunotargets for therapeutic intervention. This assumption is supported by the implication of T cells in pressure overload-induced cardiac fibrosis (Yu et al., 2006).

SUMMARY OF THE INVENTION

The inventors identified immune mediators involved in pressure overload-induced HF, finding that T cells infiltrated the pathologically hypertrophic myocardium, in line with their role in long-lasting inflammation. In fact, inflammation is a key factor distinguishing pathological hypertrophy from physiological, "benign" hypertrophy, which occurs during exercise training. Taking advantage of the presence of T cells, inventors utilized abatacept—an FDA-approved CTLA4-Ig fusion protein (marketed under the trade name ORENCIA®) that blocks T cell costimulation, selectively inhibiting pro-inflammatory T cell function (Moreland et al., 2006)—to significantly blunt cardiac dysfunction in a mouse HF model. Abatacept systemically inhibited T cell activation and reduced cardiac T cell infiltration, leading to reduced cardiomyocyte death, via a mechanism dependent upon the anti-inflammatory cytokine interleulin-10 (IL-10). Taken together, the findings of the present inventors indicate that T cells are involved in the development of pathological cardiac hypertrophy and that interfering with their activation, using e.g. existing, clinically-validated strategies, has the potential to become a therapeutic option for heart failure.

DETAILED DESCRIPTION OF THE INVENTION

It is therefore an object of the invention an inhibitor of T cell costimulation and/or activation and/or function for use in the treatment and/or prevention of cardiac pathologies, preferably heart failure diseases, and/or of related symptoms. Preferably, said inhibitor is an inhibitor of at least one molecule promoting T cell costimulation. More preferably said inhibitor increases IL-10 levels in the heart. IL-10 levels refer to mRNA or protein levels. In a preferred embodiment of the invention, said inhibitor comprises or consists of at least one molecule selected from the group consisting of: CTLA4, PD-1, PD-L1 or PD-L2, BTLA, CD160, LAG-3, 2B4, B7-H3, B7-H4, B7S3, BTNL2, blocking anti-CD28 antibodies, a functional fragment, a functional derivative or a functional analogue thereof. Preferably, the molecule promoting T cell costimulation is selected from the group consisting of: B7-1 and B7-2 (also known as CD80 and CD86), CD40, CD40L (also known as CD154), OX40, OX40L, CD30, CD30L, 4-1BB, 4-BBL, GITR, GITR ligand, LIGHT, CD27, CD45RB, CD2, LFA-3, B7-H3, B7-H4, ICOS and ICOS ligands. In a preferred embodiment of the invention, the inhibitor is at least one molecule selected from the group consisting of: blocking antibody or functional fragment thereof, or small molecule inhibitor or polynucleotide. Preferably, said inhibitor is a molecule comprising or consisting of CTLA4 or a functional fragment or a functional derivative or a functional analogue thereof. More preferably, the inhibitor is a CTLA4-Ig molecule or a functional fragment or a functional derivative thereof or a functional analogue thereof. Preferably said CTLA4-Ig molecule is a fusion protein comprising a first amino acid sequence containing amino acid residues corresponding to the extracellular domain of CTLA4 and a second amino acid sequence containing the Fc region of the Immunoglobulin IgG1. More preferably said CTLA4-Ig molecule comprises or essentially consists of the amino acid sequence of SEQ ID NO: 1, or a functional fragment or a functional derivative thereof or a functional analogue thereof. In a more preferred embodiment, said inhibitor is Abatacept. Other objects of the invention are a nucleic acid molecule encoding for the inhibitor as defined above, for use in the treatment and/or prevention of cardiac pathologies, preferably heart failure diseases, and/or of related symptoms; an expression vector comprising said nucleic acid or encoding for the inhibitor as defined above, for use in the treatment and/or prevention of cardiac pathologies, preferably heart failure diseases, and/or of related symptoms; a genetically engineered host cell or nanoparticle or microvesicle which expresses the inhibitor as defined above, for use in the treatment and/or prevention of cardiac pathologies, preferably heart failure diseases, and/or of related symptoms. A further object of the invention is a pharmaceutical composition comprising the inhibitor as above defined, or the nucleic acid molecule as above defined, or the expression vector as above defined, or the genetically engineered host cell or nanoparticle or microvesicle as above defined, and at least one pharmaceutically acceptable carrier, for use in the treatment and/or prevention of cardiac pathologies, preferably heart failure diseases, and/or of related symptoms. The inhibitor as above defined is preferably selected from:

a) polynucleotide;
b) a polypeptide;
c) a polynucleotide coding for said polypeptide;
d) a vector comprising or expressing said polynucleotide of a) or c);
e) a genetically engineered host cell able to express in suitable conditions said polypeptide or said polynucleotide of a) or c);
f) a small molecule;
g) an antibody or synthetic or recombinant derivative thereof.

Cardiac pathologies comprise at least one pathology selected from the group consisting of: heart failure diseases; heart failure following myocarditis; coronary artery disease, which may lead to heart attacks and heart muscle weakness; primary heart muscle weakness which may derive from viral infections or toxins, such as prolonged alcohol exposure; heart valve disease causing heart muscle weakness which may be due to too much leaking of blood or heart muscle stiffness from a blocked valve; and hypertension (high blood pressure). Rarer causes of said pathologies include hyperthyroidism (high thyroid hormone), vitamin deficiency, and excess amphetamine ("speed"). Said related symptoms of cardiac pathologies are preferably cardiac fibrosis and/or shortness of breath (dyspnea) and/or asthma due to the heart (cardiac asthma) and/or pooling of blood (stasis) in the general body (systemic) circulation or in the liver's (portal) circulation and/or swelling (edema) and/or blueness or duskiness (cyanosis), and/or enlargement (hypertrophy) of the heart. In some embodiments, the heart failure is not an inflammatory cardiomyopathy caused by autoimmunity. In some embodiments, the heart failure is not an inflammatory cardiomyopathy caused by an immune response to infection. Such infection may, e.g., be viral infection or, e.g., bacterial infection. In some embodiments, the heart failure is not an inflammatory cardiomyopathy caused by autoimmunity or by an immune response to infection (e.g.: not caused by an immune response to viral infection).

In the context of the present invention an "inhibitor of T cell activation" means an agent able to inhibit or reduce T cell activation. For the purpose of this invention, "activation" is defined as the stimulating signal (known also as "signal 1") received by T cells via their T cell receptor (e.g. via antigen complexed with a major histocompatibility molecule, or via anti-CD3 antibodies), which is not sufficient on its own to drive a T cell response in naïve T cells. For a fully functional T cell response, a second signal (also known as "signal 2") is required, which is not dependent on antigen and which co-stimulates the T cell receptor. This second signal is termed, for the purpose of this invention, "costimulation". For further details on this definition of costimulation, see A Sharpe 2009 Immunological Reviews 2009: 229(1): 5-11.

After being activated and costimulated, the T cells to exhibit a phenotype of an activated (or functional) T cell. The expression "activated (or functional) T cell" describes T cells or B cells that can exhibit some of the following phenotypes: T cell activation can be measured by methods not limited to the following: CD69, CD25, HLA-DR, CD62L and/or CD1 54 expression and/or the production of IL-2, calcium mobilization, ZAP-70 phosphorylation, LAT phosphorylation, Lck phosphorylation, NF-[kappa]B activation, MEK activation, NFAT activation, Ap-I activation; T cell proliferation and cytotoxicity (defined as the ability to kill target cells).

In the context of the present invention an "inhibitor of T cell costimulation" means an agent able to inhibit or reduce T cell costimulation. In the context of the present invention an "inhibitor of T cell function" means an agent able to inhibit or reduce T cell activation, costimulation, differentiation or function The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more decrease) and/or a decrease or reduction in the specified activity of at least about 5%, 10%, 25%, 35%, 40%, 50%, 60%, 75%, 80%, 90%, 95%, 97%, 98%, 99% or 100%. In particular embodiments, the inhibition or reduction results in little or essentially no detectible activity (at most, an insignificant amount, e.g., less than about 10% or about 5%). Nonlimiting examples of inhibitor according to the invention are an antibody or fragment thereof or other ligand or fragment thereof that specifically binds and/or inhibits activity of CD3 protein, CD40 protein, B7 family proteins, and/or CD28 family proteins; cyclosporine; FK504; steroids; and/or substances that target MHC-I and/or MHC-II molecules, immunosuppressive drugs, interferons, corticosteroids, azathioprine, cyclophosphamide, etc. Also included are inhibitors that reduce or inhibit CD3 (e.g., OKT<(R)>3 monoclonal antibody), CD40, B7 and/or CD28 activity in T cells at the transcriptional, post-transcriptional, translational and/or post-translational level, therapies that target T cell activation transcription factors, such as inhibitors of IKB kinase (IKK), which would also inhibit the transcription factor, Nuclear Factor kappa light chain enhancer in B cells (NF-[kappa]b), or cyclosporine, which inhibits the calcineurin pathway important for the activation of the transcription factor, Nuclear Factor of Activated T cells. Also included are Basiliximab (anti-CD25), Alefacept (LFA3-Ig fusion; blocks CD2), Daclizumab (Anti-CD25), Tysabri (anti-VLA4) and anti-CLA4 Ab. Other inhibitors that can be used in the present invention include but are not limited to Omalizumab (Anti-IgE mab; targets mast cells and basophils) and Lumiliximab (anti-CD23; targets mast cells and basophils).

The precursor protein of IL-10 may be represented by the sequence of NCBI Accession numbers: NP_000563.1 GI:10835141. CTLA4 may be represented by the sequence of NCBI Accession numbers: NP_005205.2 GI:21361212 and NP_001032720.1 GI:83700231. PD-1 may be represented by the sequence of NCBI Accession numbers: NP_005009.2 GI: 167857792. PD-L1 may be represented by the sequence of NCBI Accession numbers: NP_001300958.1 GI: 930425329, NP_001254635.1 GI: 390979639, NP_054862.1 GI: 7661534. PD-L2 may be represented by the sequence of NCBI Accession numbers: NP_079515.2 GI: 190014605. BTLA may be represented by the sequence of NCBI Accession numbers: NP_861445.3 GI: 145580621, NP_001078826.1 GI: 145580619. CD160 may be represented by the sequence of NCBI Accession numbers: NP_008984.1 GI: 5901910. LAG-3 may be represented by the sequence of NCBI Accession numbers: NP_002277.4 GI: 167614500. 2B4 may be represented by the sequence of NCBI Accession numbers: NP_057466.1 GI: 7706529, NP_001160136.1 GI: 262263438, NP_001160135.1 GI: 262263435. B7-H3 may be represented by the sequence of NCBI Accession numbers: NP_001019907.1 GI: 67188443, NP_079516.1 GI: 13376852. B7-H4 may be represented by the sequence of NCBI Accession numbers: NP_001240779.1 GI: 359718947, NP_001240778.1 GI: 359718944, NP_078902.2 GI: 99028881. B7S3 may be represented by the sequence of NCBI Accession numbers:NP_001272892.1 GI: 552953846, NP_001272894.1 GI: 552953752. BTNL2 may be represented by the sequence of NCBI Accession numbers: NP_001291490.1 GI: 752292706.

B7-1 (also known as CD80) may be represented by the sequence of NCBI Accession numbers: NP_005182.1 GI: 4885123. B7-2 (also known as CD86) may be represented by the sequence of NCBI Accession numbers: NP_001193854.1 GI: 332634954, NP_001193853.1 GI: 332634950, NP_795711.1 GI: 332634944, NP_787058.4 GI: 332634934, NP_008820.3 GI: 332634929. CD40 may be represented by the sequence of NCBI Accession numbers: NP_001289682.1 GI: 720642787, NP_690593.1 GI: 23312371, NP_001241.1 GI: 4507581. CD40L (also known as CD154) may be represented by the sequence of NCBI Accession numbers: NP_000065.1 GI: 4557433. OX40 may be represented by the sequence of NCBI Accession numbers: NP_003318.1 GI: 4507579. OX40L may be represented by the sequence of NCBI Accession numbers: NP_001284491.1 GI: 662033902, NP_003317.1 GI: 4507603. CD30 may be represented by the sequence of NCBI Accession numbers: NP_001268359.2 GI: 597709797, NP_001234.3 GI: 597709795. CD30L may be represented by the sequence of NCBI Accession numbers: NP_001239219.1 GI: 356582497, NP_001235.1 GI: 4507607. 4-1BB may be represented by the sequence of NCBI Accession numbers: NP_001552.2 GI: 5730095. 4-BBL may be represented by the sequence of NCBI Accession numbers: NP_003802.1. GITR may be represented by the sequence of NCBI Accession numbers: NP_683700.1 GI: 23238197, NP_683699.1 GI: 23238194, NP_004186.1 GI: 4759246. GITR ligand may be represented by the sequence of NCBI Accession numbers: NP_005083.2 GI: 157419142). LIGHT may be represented by the sequence of NCBI Accession numbers: NP_742011.2 GI: 291045244, NP_003798.2 GI: 25952144). CD27 may be represented by the sequence of NCBI Accession numbers: NP_001233.1 GI: 4507587. CD45RB may be represented by the sequence of NCBI Accession number: NG_007730. CD2 may be represented by the sequence of NCBI Accession numbers: NP_001758.2 GI: 156071472. LFA-3 may be represented by the sequence of NCBI Accession numbers: NP_001138294.1 GI: 221316575, NP_001770.1 GI: 4502677. B7-H3 may be represented by the sequence of NCBI Accession numbers: NP_001019907.1 GI: 67188443, NP_079516.1 GI: 13376852. B7-H4 may be represented by the sequence of NCBI Accession numbers: NP_001240779.1 GI: 359718947, NP_001240778.1 GI: 359718944, NP_078902.2 GI: 99028881. ICOS (also known as B7-H2) may be represented by the sequence of NCBI Accession numbers: NP_036224.1 GI: 15029518. ICOS ligands may be represented by the sequence of NCBI Accession numbers: NP_001269981.1 GI: 545688894. The inhibitors according to the invention are preferably monoclonal blocking antibodies or fragments thereof, ScFvs or soluble fusion proteins of the inhibitory molecules. Cytotoxic T-lymphocyte-associated antigen 4 (CTLA4), which is also known as CD152, is a protein involved in the regulation of the immune system. Naturally occurring CTLA4 is described in U.S. Pat. Nos. 5,434,131 , 5,844,095, and 5,851,795. Natural CTLA4 proteins are encoded by the CTLA4 gene. CTLA4 is a cell surface protein, having an N-terminal extracellular domain, a transmembrane domain, and a C-terminal cytoplasmic domain. The extracellular domain binds to and/or interferes with target antigens, such as CD80 and CD86, serves as nature natural break of T cell stimulation. In some embodiments, the extracellular domain of the CTLA4 molecule begins with methionine at position +1 and ends at aspartic acid at position +124; in other embodiments, the extracellular domain begins with alanine at position ~1 and ends at aspartic acid at position +124.

A CTLA4 molecule is a molecule comprising a cytotoxic T-lymphocyte-associated antigen 4 (CTLA4) extracellular domain. In some embodiments, the extracellular domain of CTLA4 comprises a portion of the CTLA4 protein that recognizes and binds to at least one B7 (CD80/86) antigens such as a B7 antigen expressed on B cells and APCs. The extracellular domain may also include fragments or derivatives of CTLA4 that bind a B7 antigen. The CTLA4 extracellular domain can also recognize and bind CD80 (B7-1) and/or CD86 (B7-2). The extracellular domain may also include fragments or derivatives of CTLA4 that bind a binds CD80 and/or CD86. The CTLA4 molecule may be a fusion protein, where a fusion protein is defined as one or more amino acid sequences joined together using methods well known in the art. The joined amino acid sequences thereby form one fusion protein. In some embodiments, the CTLA4 molecule contains at least a portion of an immunoglobulin, such as the Fc portion of an immunoglobulin. In some embodiments, the CTLA4 molecule is an isolated and purified CTLA4 molecule. In a preferred embodiment, the T-cell costimulation inhibitor comprises the extracellular domain of CTLA4, or a functional fragment or immunologically active variant thereof. The T-cell costimulation inhibitor may bind a B7 antigen expressed on B cells or other antigen presenting cells (APCs). In some embodiments, the B7 antigen is expressed on B cells and on APCs. In some embodiments, the fusion protein is Abatacept. Abatacept is a soluble fusion protein that consists of the extracellular domain of human CTLA-4 linked to the modified Fc (hinge, CH2, and CH3 domains) portion of human immunoglobulin G1 (IgG 1). Abatacept is produced by recombinant D A technology in a mammalian cell expression system. The apparent molecular weight of abatacept is 92 kilodaltons. Abatacept was developed by Bristol-Myers Squibb and is disclosed, for example, in U.S. Pat. Nos. 5,851,795, 7,455, 835, and U.S. Pat. Pub. 2001 1/31 1529. Abatacept selectively binds to CD80 and CD86, thereby blocking the interaction with CD28 and interfering with T-cell activation. It inhibits naive T-cell activation, thus having the potential to selectively inhibit T-cell response to specific antigens instead of broad immunosuppression. In some embodiments, the composition further comprises an oil-based carrier such as a water-in-oil emulsion (e.g., IFA or Montamide ISA). The composition may be administered by intravenous infusion, such as in about 50 to 200 ml of physiological saline or at a dose ranging from about 5 mg/kg to about 50 mg/kg or at a dose ranging from about 250 to 2000 mg, or at a dose of 500 mg, 750 mg, or 1000 mg.

Dosages of the agents can vary depending on the subject and the mode of administration, US patent application US Publication Number US 2003/0083246 and US patent application US Publication Number US 2004/0022787 teach dosage and administration schedules for CTLA4Ig having the amino acid sequence shown in SEQ ID NO:2 for treating rheumatic diseases, such as rheumatoid arthritis. All are herein incorporated by reference. An effective amount of CTLA4Ig molecule may be an amount about 0.1 to 100 mg/kg weight of a subject. In another embodiment, the effective amount is an amount about 0.1 to 20 mg/kg weight of a subject. In a specific embodiment, the effective amount of CTLA4Ig is about 2 mg/kg weight of a subject. In another specific embodiment, the effective amount of CTLA4Ig is about 10 mg/kg weight of a subject. In another specific embodiment, an effective amount of CTLA4Ig is 500 mg for a subject weighing less than 60 kg, 750 mg for a subject weighing between 60-100 kg and 1000 mg for a subject weighing more than 100 kg. An effective amount of CTLA4Ig molecule may be administered to a subject daily, weekly, monthly and/or yearly, in single or multiple times per hour/day/week/month/year, depending on need. For example, in one embodiment, an effective amount of the CTLA4Ig molecule may initially be administered once every two weeks for a month, and then once every month thereafter. The administration of the CTLA4Ig molecules of the invention can be via a 30 minute to one or more hour intravenous infusion. Alternatively, single to multiple subcutaneous injections can deliver the required dosage. Typically, a 30 minute intravenous infusion is the administration route utilized during the early phase of treatment. The dose may be repeated 2 and 4 weeks after the initial dose, then every 4 weeks thereafter. It may be administered alone or with disease-modifying drugs other than TNF antagonists. The subcutaneous injection is the typical administration mode utilized during the maintenance phase. For example after a single intravenous infusion as a loading dose (as per body weight categories above), 125 mg administered by subcutaneous injection may be given within a day, followed by 125 mg subcutaneously once a week. Patients who are unable to receive an infusion may initiate weekly injections subcutaneously without an Intravenous loading dose. Patients transitioning from intravenous therapy to subcutaneous administration may administer the first subcutaneous dose instead of the next scheduled intravenous dose.

Abatacept monomer comprises a CTLA4-Ig polypeptide of the following sequence:

(SEQ ID NO: 1)
MHVAQPAVVLASSRGIASFVCEYASPGKATEVRVTVLRQADSQVTEVCAA

TYMMGNELTFLDDSICTGTSSGNQVNLTIQGLRAMDTGLYICKVELMYPP

PYYLGIGNGTQIYVIDPEPCPDSDQEPKSSDKTHTSPPSPAPELLGGSSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGK

The extracellular domain of CTLA4 corresponds to aa. 1-125 of SEQ ID NO:1. CTLA4 functional derivatives comprises variants thereof. CTLA4-Ig molecules can have wild-type or mutant sequences, for example, with respect to the CTLA4 extracellular domain and immunoglobulin constant region sequences. A CTLA4-Ig monomer molecule can comprise an extracellular domain of human CTLA4. In one embodiment, the extracellular domain can comprise the nucleotide sequence of nucleotides 89-463 of SEQ ID NO:1 as disclosed in EP1962886 that code for SEQ ID NO:1. In another embodiment, the extracellular domain can comprise mutant sequences of human CTLA4. In another embodiment, the extracellular domain can comprise nucleotide changes to nucleotides 89-463 of SEQ ID NO: 1 as disclosed in EP1962886 such that conservative amino acid changes are made. In another embodiment, the extracellular domain can comprise a nucleotide sequence that is at least 75%, 80%, 85%, 90%, 95%, 96%, 97%, 98%, or 99% identical to nucleotides 89-463 of SEQ ID NO: 1 as disclosed in EP1962886. In one embodiment, a CTLA4-Ig monomer molecule comprises a modified human IgG1 hinge region (nucleotides 464-508 of SEQ ID NO: 1 as disclosed in EP1962886; amino acids 152-166 of SEQ ID NO:2) wherein the serines at amino acid residues 156, 162, and 165 of SEQ ID NO:1 have been engineered from cysteines present in the wild-type sequence. The CTLA4 variants optionally comprise at least one amino acid modification in a native CTLA4 protein or in SEQ ID NO: 1. In this embodiment, one or more modifications are made at one or more of the following positions (numbering as in SEQ ID NO:1): 29, 30, 31, 33, 35, 49, 51, 53, 59, 61, 63, 64, 93, 95, 97, 98, 102, 103, 104, 105 or 106. In some embodiments, the modification is one or more of the following substitutions: A29E, A29F, A29H, A29K, A29N, A29Q, A29R, T30E, T30H, T30R, T30V, E31D, E31I, E31M, E31T, E31V, R33E, R33F, R33I, R33L, R33M, R33Q, R33T, R33W, R33Y, T35D, T35E, T35F, T35M, T35V, T35Y, A49D, A49E, A49F, A49T, A49W, A49Y, T51D, T51E, T51H, T51L, T51N, T51Q, T51R, T51S, T51V, M53E, M53F, M53H, M53Q, M53W, M53Y, T59H, T59I, T59L, T59N, T59Q, T59V, T59Y, L61A, L61D, L61E, L61F, L61G, L61H, L61I, L61,K, L61M, L61N, L61P, L61Q, L61R, L61S, L61T, L61V, L61W, L61Y, D63E, S64K, S64R, S64Y, K93D, K93E, K93F, K93H, K93N, K93Q, K93R, K93S, K93T, K93V, K93W, K93Y, E95D, E95H, E95L, E95Q, E95Y, M97D, M97F, M97I, M97N, M97V, Y98F, Y98W, Y102F, Y102W, Y103D, Y103E, Y103F, Y103H, Y103N, Y103Q, Y103W, L104F, L104H, L104M, LI 04V, L104Y, G105D, G105E, I106E, and I106Y. Of particular use in some embodiments are CTLA4 variants that have one or more substitutions selected from A29H, T51N, M53Y, L61E, and K93Q, with combinations of particular use including A29H/K93Q, A29H/M53Y, A29H/T5 IN, T51N/K93Q, T51N/M53Y, A29H/L61E/K93Q, A29H/M53Y/K93Q, A29H/M53Y/L61E, A29H/T51N/L61E, M53Y/L61E/K93Q, T51N/L61E/K93Q, T51N/M53Y/L61E, A29H/M53Y/L61E/K93Q, A29H/T51N/L61E/K93Q, A29H/T51N/M53Y/K93Q, A29H/T51N/M53Y/L61E, T51N/M53Y/L61E/K93Q, and A29H/T51N/M53Y/L61E/K93Q.

Any combinations of individual substitutions can be made, of any and all possible combinations, and individual position or substitution can be independently included or excluded from the list of possibilities. In general, as compared to the wild-type or parent CTLA4 (or Fc region), generally the variants of the invention have 1, 2, 3, 4, or 5 amino acid substitutions in the CTLA4 region, although in some cases more substitutions can be used, as long as the desired function is preserved. Similarly, the Fc domain may have substitutions in this manner as well. The CTLA4 variants generally preserve or enhance binding to one or more of the CTLA4 ligands, such as enhanced binding to B7-1 and/or B7-2. The Fc portion are comprised of the Fc region or some portion of the Fc region of an antibody. In certain embodiments, polypeptides are proteins that are fusions of CTLA4 with the Fc region of an antibody. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. By "Fc polypeptide" as used herein is meant a polypeptide that comprises all or part of an Fc region. Fc polypeptides include antibodies, Fc fusions, isolated Fc's, and Fc fragments. CTLA4 proteins may be linked to Fc regions via a linker. The term "linker" is used to denote polypeptides comprising two or more amino acid residues joined by peptide bonds and are used to link one or more antigen binding portions. A variety of linkers may find use in some embodiments described herein to covalently link Fc regions to a fusion partner. "Linker" herein is also referred to as "linker sequence", "spacer", "tethering sequence" or grammatical equivalents thereof. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used. Useful linkers include glycine-serine polymers, including for example (GS)n, where n is an integer of at least one, glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

CTLA4-Ig proteins disclosed herein may comprise a variant CTLA4, a variant Fc region, or both a variant CTLA4 and a variant Fc region. A variant comprises one or more amino acid modifications relative to a parent CTLA4-Ig protein, wherein the amino acid modification(s) provide one or more described properties. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence. Antibody Fc regions contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide normally consists of GlcNAc2Man3GlcNAc, with differing numbers of outer residues. The terms "CTLA4-Ig" or "CTLA4-Ig molecule" or "CTLA4Ig molecule" or "CTLA4-Ig fusion protein" or "CTLA4-Ig protein" are used interchangeably, and refer to a protein molecule that comprises at least a polypeptide having a CTLA4 extracellular domain or portion or derivatives thereof and an immunoglobulin constant region or portion or derivatives thereof. The extracellular domain and the immunoglobulin constant region can be wild-type, or mutant or modified, and mammalian, including human or mouse. The polypeptide can further comprise additional protein domains. A CTLA4-Ig molecule can also refer to multimer forms of the polypeptide, such as dimers, tetramers, and hexamers. A CTLA4-Ig molecule also is capable of binding to CD80 and/or CD86. The term "B7-1" also refers to CD80; the term "B7-2" also refers CD86; and the term "B7" refers to both B7-1 and B7-2 (CD80 and CD86). The term "B7-1-Ig" or "B7-1Ig" refers to CD80-Ig; the term "B7-2-Ig" or "B7-2Ig" refers CD86-Ig.

Mediators of costimulation and inhbitors of costimulation refer to the molecules affecting, positively or negatively, the process of T cell costimulation, as described in (Sharpe, 2009) and (Pilat et al., 2012),In one embodiment, "CTLA4Ig" refers to a protein molecule having the amino acid sequence of residues: (i) 26-383 of SEQ ID NO:2 , (ii) 26-382 of SEQ ID NO:2; (iii) 27-383 of SEQ ID NO:2, or (iv) 27-382 of SEQ ID NO:2, or optionally (v) 25-382 of SEQ ID NO:2, or (vi) 25-383 of SEQ ID NO:2. In monomeric form these proteins can be referred to herein as "SEQ ID NO:2 monomers," or monomers "having a SEQ ID NO:2 sequence". These SEQ ID NO:2 monomers can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4Ig molecules. These monomers, dimers, tetramers and other multimers can be referred to herein as "SEQ ID NO:2 proteins" or proteins "having a SEQ ID NO:2 sequence". The sequence SEQ ID NO:2 is e.g. disclosed in WO/2007/076354 and WO/2002/002638 and consists of:

(SEQ ID NO: 2)
MGVLLTQRTLLSLVLALLFPSMASMAMHVAQPAVVLASSRGIASFVCEYA

SPGKATEVRVTVLRQADSQVTEVCAATYMMGNELTFLDDSICTGTSSGNQ

VNLTIQGLRAMDTGLYICKVELMYPPPYYLGIGNGTQIYVIDPEPCPDSD

QEPKSSDKTHTSPPSPAPELLGGSSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK
SRWQQGNVFSCSVMHEALHNHYTQKSLSLSPGK.

The corresponding nucleotide sequence is disclosed in WO/2002/002638. As utilized herein "Abatacept" preferably refers to SEQ ID NO:1 proteins. As used herein, the term "heart failure" also comprises "congestive heart failure, (CHF)" "chronic heart failure," "acute heart failure", and refer to any condition in which the heart is unable to pump blood at an adequate rate or to do so only in the presence of increased left ventricular filling pressures. When the heart is unable to adequately pump blood to the rest of the body at normal filling left ventricular pressures, blood can back up into the lungs, causing the lungs to become congested with fluid. Typical symptoms of heart failure include shortness of breath (dyspnea), fatigue, weakness, difficulty breathing when lying flat, and swelling of the legs, ankles or abdomen (edema). Causes of heart failure are related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. Heart failure can occur in the presence of a normal (>50%) or a reduced (<50%) left ventricular ejection fraction. There is increased recognition that these two conditions represent two different disease states, rather than a continuum (Borlaug B A, Redfield MM. Circulation. 2011 May 10; 123 (18):2006-13).

Heart failure according to the present invention includes overt and/or advanced heart failure. In overt heart failure, the subject shows symptoms of heart failure as known to the person skilled in the art. HF can be classified into various degrees of severity. According to the NYHA (New York Heart Association) classification, heart failure patients are classified as belonging to NYHA classes I, II, III and IV. A patient having heart failure has already experienced structural and functional changes to his pericardium, myocardium, coronary circulation or cardiac valves. He will not be able to fully restore his health, and is in need of a therapeutical treatment. Patients of NYHA Class I have no obvious symptoms of cardiovascular disease but already have objective evidence of functional impairment. Patients of NYHA class II have slight limitation of physical activity. Patients of NYHA class III show a marked limitation of physical activity. Patients of NYHA class IV are unable to carry out any physical activity without discomfort. They show symptoms of cardiac insufficiency at rest. This functional classification is supplemented by the more recent classification by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy and/or impaired LV function would be designated as stage B. Stage C then denotes patients with current or past symptoms of HF associated with underlying structural heart disease (the bulk of patients with HF), and stage D designates patients with truly refractory HF. The terms "antibody" and "immunoglobulin" can be used interchangeably and are herein used in the broadest sense and encompass various antibodies and antibody mimetics structures, including but not limited to monoclonal antibodies, polyclonal antibodies, multispecific antibodies (e.g., bispecific antibodies), chimeric antibodies, nanobodies, antibody derivatives, antibody fragments, anticalins, DARPins, affibodies, affilins, affimers, affitins, alphabodies, avimers, fynomers, monobodies and other binding domains, so long as they exhibit the desired antigen-binding activity. An "antibody fragment" refers to a molecule other than an intact antibody that comprises a portion of an intact antibody that binds the antigen to which the intact antibody binds.

Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. VH or VL Fvs are also called "Nanobodies".

The term "antibody mimetics" refers to those organic compounds or binding domains that are not antibody derivatives but that can bind specifically an antigen like antibodies do. They include anticalins, DARPins, affibodies, affilins, affimers, affitins, alphabodies, avimers, fynomers, monobodies and others. The term "chimeric" antibody refers to an antibody in which a portion of the heavy and/or light chain is derived from a particular source or species, while the remainder of the heavy and/or light chain is derived from a different source or species.

An antibody of this invention can be any type of immunoglobulin, including IgG, IgM5 IgA, IgD, and/or IgE.

In the context of the present invention, the term "polynucleotide" includes DNA molecules (e.g., cDNA or genomic DNA) and RNA molecules (e.g., mRNA, siRNA, shRNA) and analogs of the DNA or RNA generated using nucleotide analogs. The polynucleotide may be single-stranded or double-stranded. The polynucleotide may be synthesized using oligonucleotide analogs or derivatives (e.g., inosine or phosphorothioate nucleotides). The term polynucleotide and polypeptide also includes derivatives and functional fragments thereof. A "derivative" may be a nucleic acid molecule, as a DNA molecule, coding the polynucleotide as above defined, or a nucleic acid molecule comprising the polynucleotide as above defined, or a polynucleotide of complementary sequence. In the context of the present invention the term "derivatives" also refers to longer or shorter polynucleotides and/or polypeptides having e.g. a percentage of identity of at least 41%, 50%, 60%, 65%, 70% or 75%, more preferably of at least 85%, as an example of at least 90%, and even more preferably of at least 95% or 100% with mentioned sequences or with their complementary sequence or with their DNA or RNA corresponding sequence. The term "derivatives" and the term "polynucleotide" also include modified synthetic oligonucleotides. The term "derivative" may also include nucleotide analogues, i.e. a naturally occurring ribonucleotide or deoxyribonucleotide substituted by a non-naturally occurring nucleotide. The term "derivatives" also includes nucleic acids or polypeptides that may be generated by mutating one or more nucleotide or amino acid in their sequences, equivalents or precursor sequences. The term "derivatives" also includes at least one functional fragment of the polynucleotide.

The protein mentioned in the present invention include also the corresponding protein encoded from a corresponding orthologous or homologous genes, functional mutants, functional derivatives, functional fragments or analogues, isoforms thereof.

The term "analogue" as used herein referring to a protein means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

The term "derivative" as used herein in relation to a protein means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. As used herein, the term "derivatives" also refers to longer or shorter polypeptides having e.g. a percentage of identity of at least 41%, preferably at least 41.5%, 50%, 54.9%, 60%, 61.2%, 64.1%, 65%, 70% or 75%, more preferably of at least 85%, as an example of at least 90%, and even more preferably of at least 95% with the above defined proteins or with an amino acid sequence of the correspondent region encoded from a orthologous or homologous gene. The term "derivative" also includes nucleic acids or polypeptides that may be generated by mutating one or more nucleotide or amino acid in their sequences, equivalents or precursor sequences. The term "derivative" also include functional mutants of the protein.

In the present invention "functional mutants" of the protein are mutants that may be generated by mutating one or more amino acids in their sequences and that maintain their activity e.g. the ability of inhibiting T cell costimulation. Indeed, the protein defined in the invention, if required, can be modified in vitro and/or in vivo, for example by glycosylation, myristoylation, amidation, carboxylation or phosphorylation, and may be obtained, for example, by synthetic or recombinant techniques known in the art.

In the present invention "functional" is intended for example as "maintaining their activity" e.g. the ability of inhibiting T cell costimulation.

As used herein "fragments" refers to polypeptides having preferably a length of at least 10 amino acids, more preferably at least 15, at least 17 amino acids or at least 20 amino acids, even more preferably at least 25 amino acids or at least 37 or 40 amino acids, and more preferably of at least 50, or 100, or 150 or 200 or 250 or 300 or 350 or 400 or 450 or 500 amino acids.

According to the present invention, an "effective amount" of a composition is one that is sufficient to achieve a desired biological effect, in this case an amelioration or the treatment of a cardiac pathology.

It is understood that the effective dosage will be dependent upon the age, sex, health, and weight of the recipient, kind of concurrent treatment, if any, frequency of treatment, and the nature of the effect desired. The provided ranges of effective doses of the inhibitor or molecule of the invention (e.g. from 1 mg/kg to 100 mg/kg, in particular systemically administered) are not intended to limit the invention and represent preferred dose ranges. However, the preferred dosage can be tailored to the individual subject, as is understood and determinable by one of skill in the art, without undue experimentation.

The administration of polynucleotides of the present invention may be carried out by known methods, wherein a nucleic acid is introduced into a desired target cell in vitro or in vivo.

An aspect of the present invention comprises a nucleic acid construct comprised within a delivery vehicle. A delivery vehicle is an entity whereby a nucleotide sequence can be transported from at least one media to another. Delivery vehicles may be generally used for expression of the sequences encoded within the nucleic acid construct and/or for the intracellular delivery of the construct. It is within the scope of the present invention that the delivery vehicle may be a vehicle selected from the group of RNA based vehicles, DNA based vehicles/vectors, lipid based vehicles, virally based vehicles and cell based vehicles. Examples of such delivery vehicles include: biodegradable polymer microspheres, lipid based formulations such as liposome carriers, coating the construct onto colloidal gold particles, lipopolysaccharides, polypeptides, polysaccharides, pegylation of viral vehicles. In one embodiment of the present invention may comprise a virus as a delivery vehicle, where the virus may be selected from: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

Commonly used gene transfer techniques include calcium phosphate, DEAE-dextran, transfection, electroporation and microinjection and viral methods. Another technique for the introduction of DNA into cells is the use of cationic liposomes. Commercially available cationic lipid formulations are e.g. Tfx 50 (Promega) or Lipofectamin 2000 (Life Technologies).

The above pharmaceutical compositions are preferably for systemic, oral, locally, preferably rectally, or topical administration.

The compositions of the present invention may be in form of a solution, e.g. an injectable solution, a cream, ointment, tablet, suspension or the like. The composition may be administered in any suitable way, e.g. by injection, particularly by intraocular injection, by oral, topical, nasal, rectal application etc. The carrier may be any suitable pharmaceutical carrier. Preferably, a carrier is used, which is capable of increasing the efficacy of the polynucleotide to enter the target-cells. Suitable examples of such carriers are liposomes, particularly cationic liposomes.

The expression vector of the invention can be any suitable recombinant expression vector, and can be used to transform or transfect any suitable host. Suitable vectors include those designed for propagation and expansion or for expression or both, such as plasmids and viruses. The recombinant expression vectors of the invention can be prepared using standard recombinant DNA techniques. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes. The recombinant expression vector can comprise a native or normative promoter operably linked to the nucleotide sequence encoding the inhibitor (including functional portions and functional variants thereof), or to the nucleotide sequence which is complementary to or which hybridizes to the nucleotide sequence encoding the imhibitor. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter and a promoter found in the long-terminal repeat of the murine stem cell virus. The inventive recombinant expression vectors can be designed for either transient expression, for stable expression, or for both. Also, the recombinant expression vectors can be made for constitutive expression or for inducible expression.

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. Pharmaceutical compositions suitable for oral administration can be presented in discrete units, such as capsules, cachets, lozenges, or tables, each containing a predetermined amount of the inhibitor of this invention; as a powder or granules; as a solution or a suspension in an aqueous or non-aqueous liquid; or as an oil-in- water or water-in-oil emulsion. Oral delivery can be performed by complexing an inhibitor of the present invention to a carrier capable of withstanding degradation by digestive enzymes in the gut of an animal.

Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia. Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 0.1 µg to about 10 grams of the composition of this invention. Typically the patient doses for parenteral administration of the compounds described herein range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline. Pharmaceutical compositions suitable for rectal administration are preferably presented as unit dose suppositories. These can be prepared by admixing the composition with one or more conventional solid carriers, such as for example, cocoa butter and then shaping the resulting mixture. Pharmaceutical compositions of this invention suitable for topical application to the skin preferably take the form of an ointment, cream, lotion, paste, gel, spray, aerosol, or oil. Carriers that can be used include, but are not limited to, petroleum jelly,—lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin. Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example,—Pharmaceutical Research 3:318 (1986)) and typically take the form of an optionally buffered aqueous solution of the composition of this invention. Furthermore, the compositions of this invention can be administered orally, intranasally, parenterally (e.g., intravenously), by intramuscular injection, by intraperitoneal injection, transdermally, extracorporeally, topically or the like. The exact amount of the required nucleic acid or vector as defined above will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein. In the above compositions further materials as well as processing techniques and the like may be set out in Part 5 of Remington's Pharmaceutical Sciences, 20th Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in Remington's Pharmaceutical Sciences. Furthermore, pharmaceutical formulations can be prepared using a process, which is generally known in the pharmaceutical art. The pharmaceutical composition for use according to the invention may further comprise an effective amount of at least another therapeutic agent. Sai therapeutic agent may be one or more of: b-blockers, diuretics, aldosterone antagonists, ACE inhibitors, Angiotensin Receptor Blockers, diuretics, digitalis, phosphodiesterase inhibitors, hydralazine and isosorbide dinitrate, or administration of mechanical support. In the present invention, when the molecule of the invention is administered with another therapeutic agent, it may be administered simultaneously or sequentially.

T cell activation can be measured by methods not limited to the following: detection and/or quantitation of protein and/or mRNA of cell surface markers such as CD69, CD25, HLA-DR, CD62L, CD 154 and/or the production of IL-2, calcium mobilization, ZAP- 70 phosphorylation, LAT phosphorylation, Lck phosphorylation; NF-[kappa]B activation, MEK activation, NFAT activation, Ap-I activation; T cell proliferation and cytotoxicity (the latter only in the case of $CD8^+$ T cells) (defined as the ability to kill target cells). Changes in the amount of the above molecules at protein protein and/or mRNA level can be detected, whereby an increase or decrease in their amount can identify an increase or decrease, respectively in the activation of a T cell over time.

In a preferred embodiment, the vector according to the invention is an expression vector selected from the group consisting of: plasmids, viral particles and phages.

Preferably, said host cell is selected from the group consisting of: bacterial cells, fungal cells, insect cells, animal cells, plant cells, preferably being an animal cell, more preferably a human cell. As used herein, the term "genetically engineered host cell" relates to host cells which have been transduced, transformed or transfected with the polynucleotide or with the vector described previously. As representative examples of appropriate host cells, one can cite bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell.

In a preferred embodiment, the inhibitor as above defined is combined with at least one therapeutic agent, preferably at least one of: b-blockers, diuretics, aldosterone antagonists, ACE inhibitors, Angiotensin Receptor Blockers, diuretics, digitalis, phosphodiesterase inhibitors, hydralazine and isosorbide dinitrate, mechanical support.

In the invention, the subject (or patient) is a mammalian, preferably a human.

The invention will be now illustrated by means of non-limiting examples referring to the following figures.

Figure 1B:
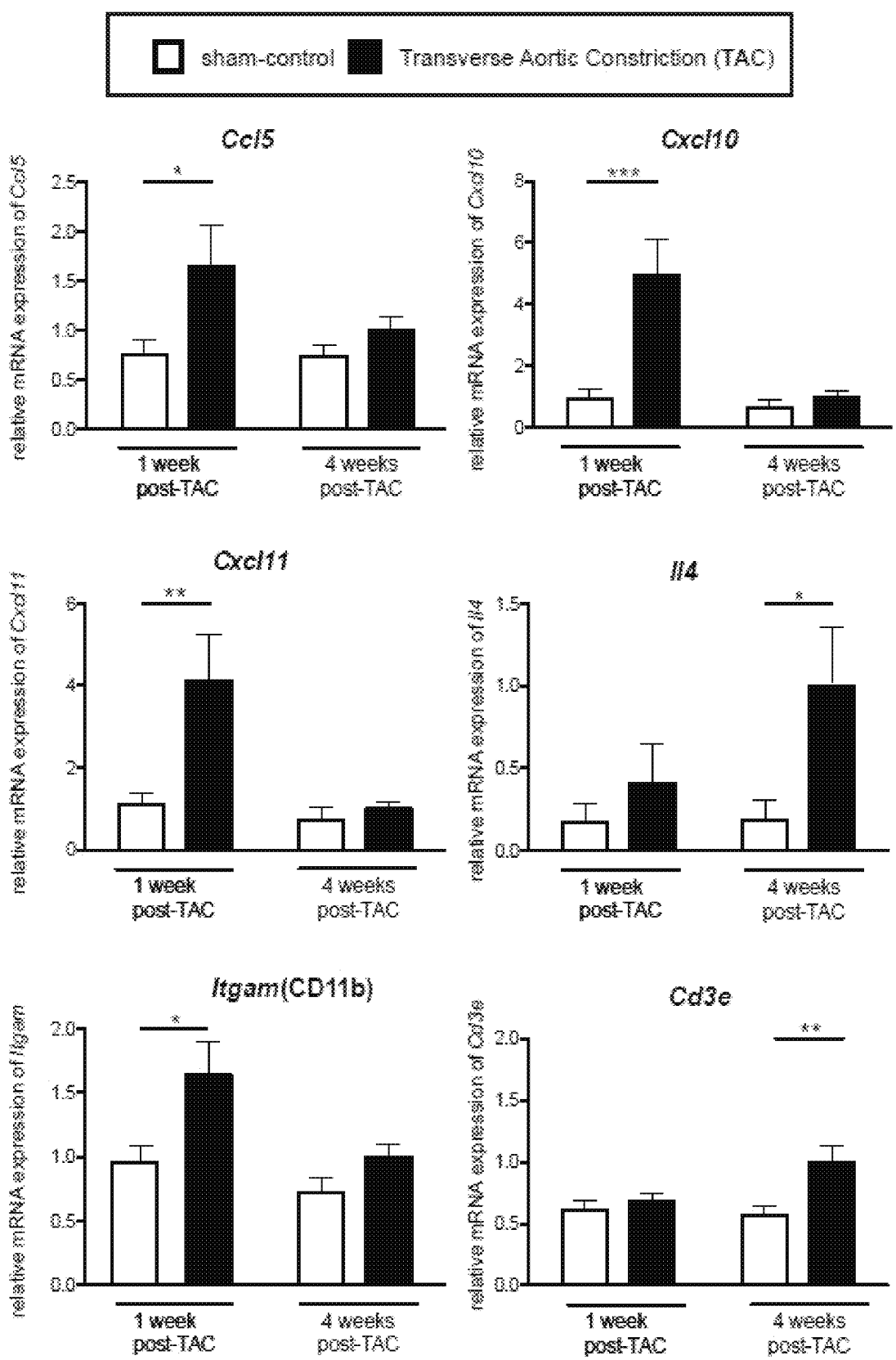

FIGS. 1A-1B. Characterization of the inflammatory signature in hypertrophic left ventricle of mice. Gene expression analysis (TaqMan real-time qPCR) of mediators of inflammation within the left ventricle of C57BL6/J mice. Relative mRNA expression in sham-operated control mice (white bars) and TAC-operated mice (black bars) at 1 and 4 weeks after surgery, internally normalized to 18s rRNA expression. Tnfa, Il6, Tgfb1, Ccl2, Ccl4, Ccl5, Cxcl10, Cxcl11 and the innate cell marker Itgam (CD11b) were significantly increased in the TAC group compared to sham, 1 week after TAC. Four weeks after the operation, Il4 and the T cell marker Cd3e were significantly increased. Values are mean±SEM (n=7-9). Two-way ANOVA, Bonferroni post-test: *, p-value<0.05; , p-value<0.01; *, p-value<0.001.

Figure 2:
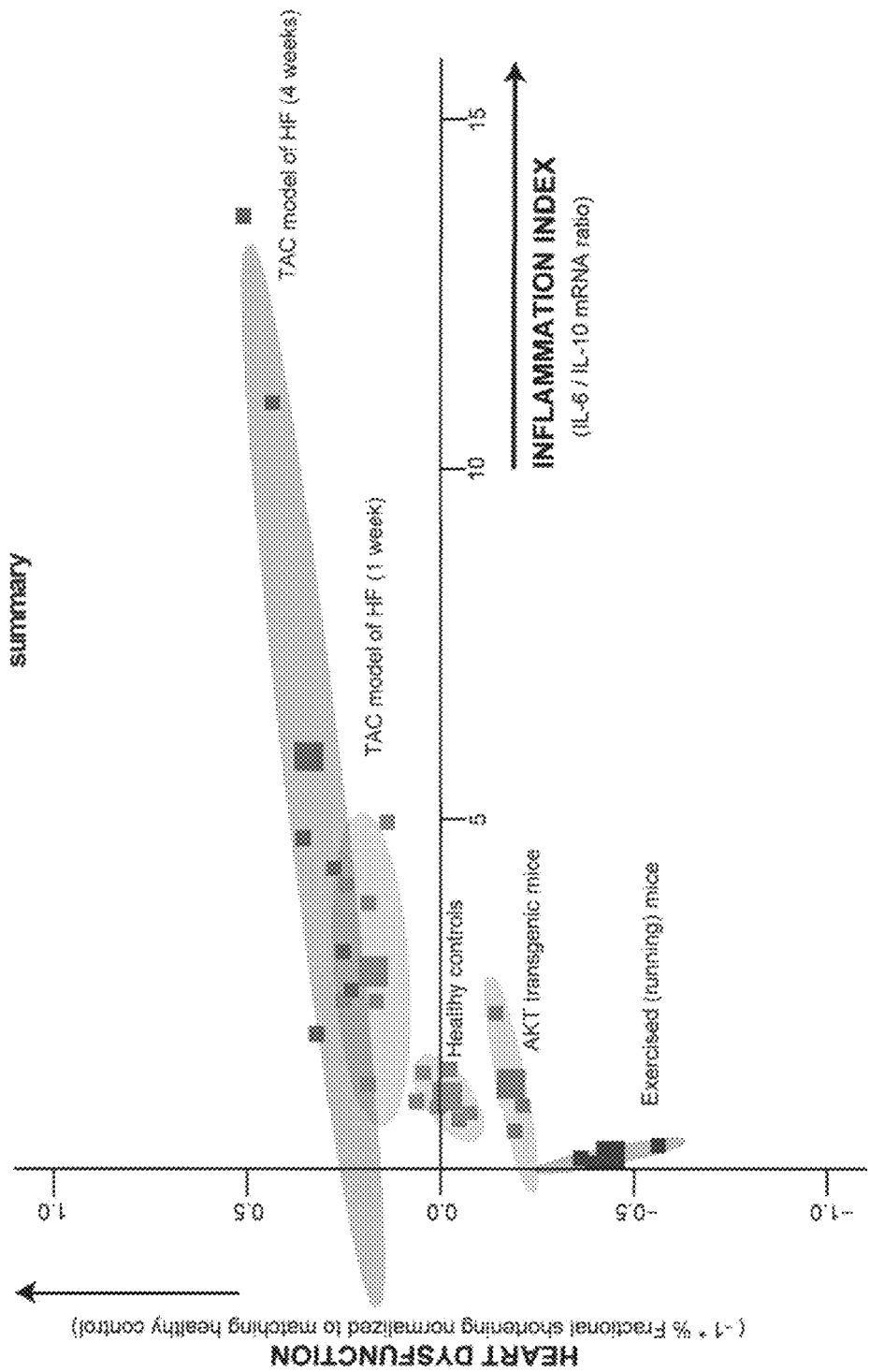

FIG. 2. The association between inflammation and heart dysfunction. Heart dysfunction index (HDI) plotted on the y axis, calculated as (−1)×(% fractional shortening), for all mouse models analyzed in this study (normalized to their matching control groups) versus an inflammation index on the x axis, calculated as mRNA level of the pro-inflammatory cytokine IL-6 divided by mRNA level of the anti-inflammatory cytokine IL-10. Each point represents data from one mouse. Larger points indicate the mean of each group, whereas the shaded ellipses represent one standard deviation from the mean. HDI values were normalized to avoid strain background-specific variations. Healthy refers to sham-operated control (PBS-treated) animals. TAC model of HF refers to TAC-operated control (PBS-treated) mice. The normalization of the HDI for each mouse was calculated with the following formula: [[HDI of sample−mean HDI of matching control]/mean HDI of matching control]. The following groups were used as matching controls for normalization: for TAC-operated mice at 1 or 4 weeks post-operation: sham-operated mice prior to operation (basal reading); for healthy mice (sham-operated): sham operated prior to operation (basal reading); for Akt transgenic: WT control; for running mice: congenic sedentary mice.

Figure 3A:
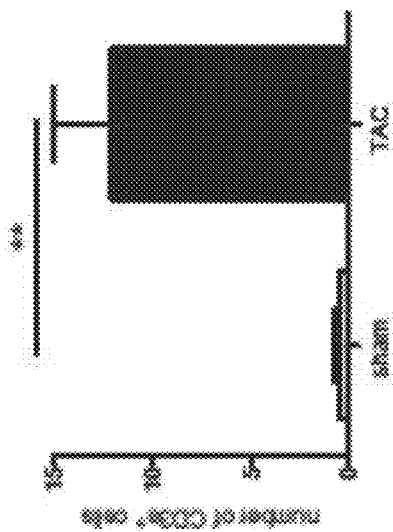
Figure 3B:
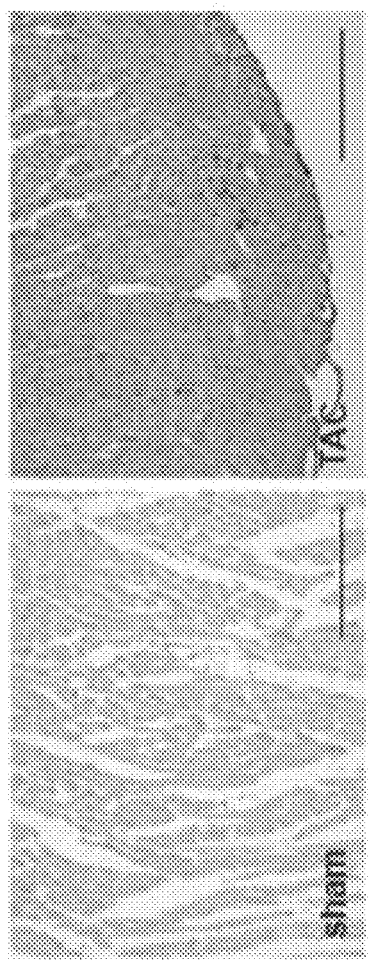
Figure 3C:
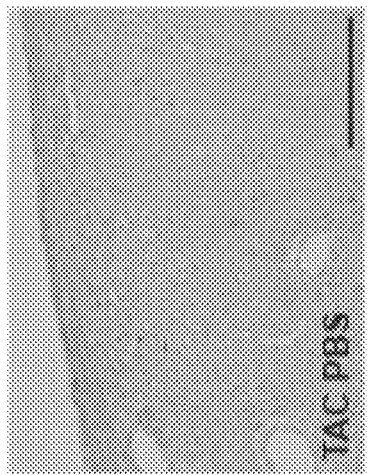
Figure 3D:
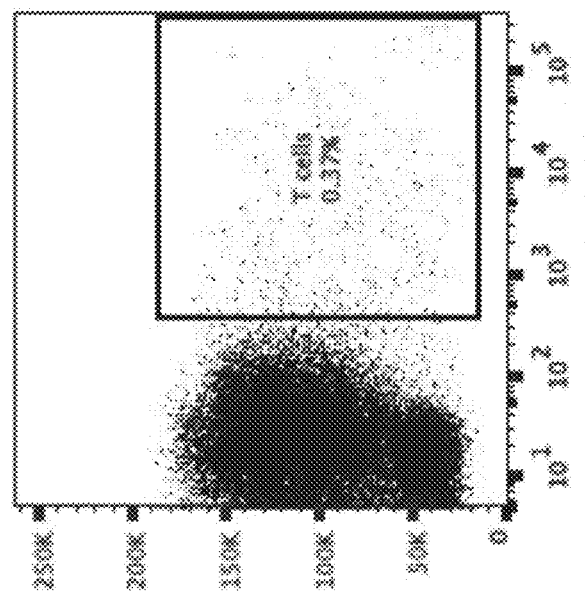
Figure 3E:
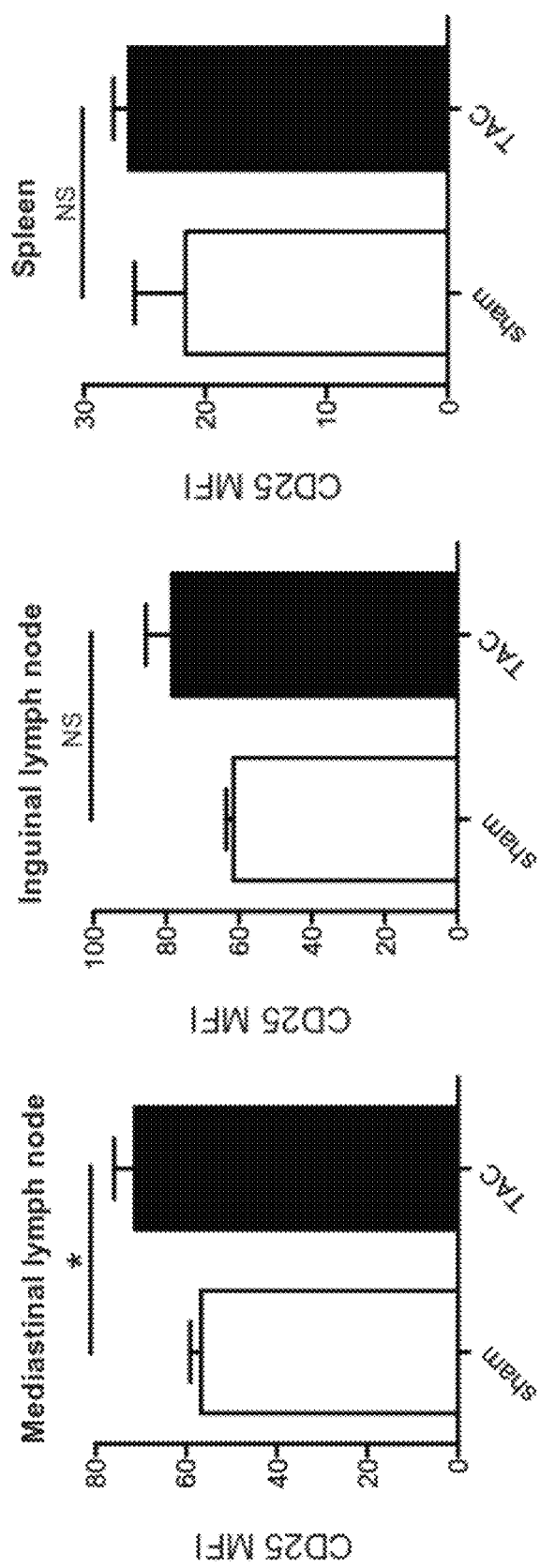
Figure 3G:
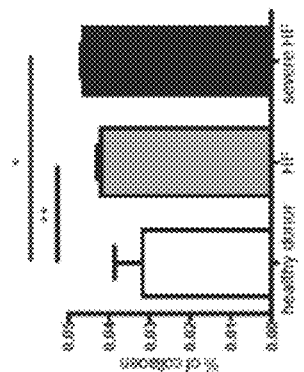
Figure 3I:
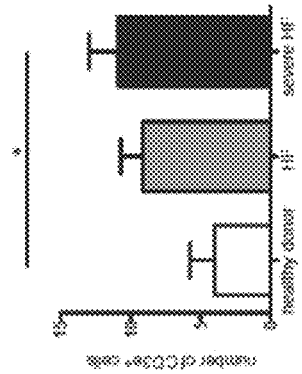
Figure 3F:
Figure 3H:
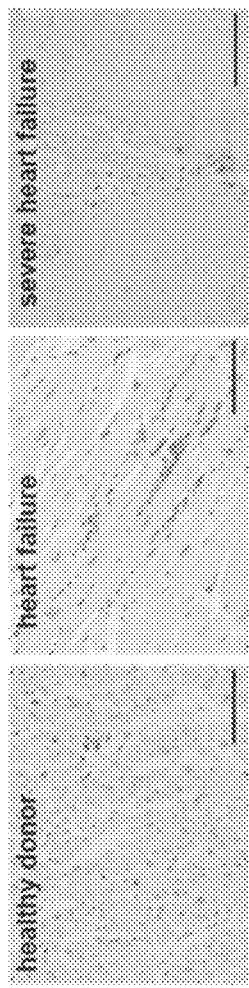
Figure 3K:
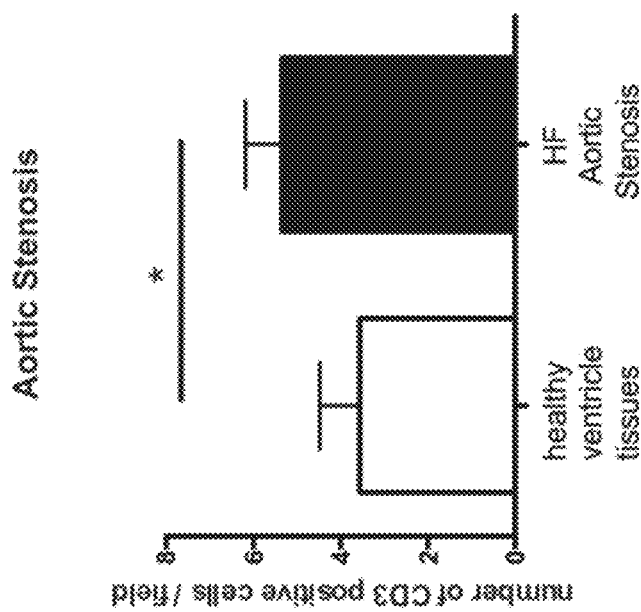
Figure 3J:
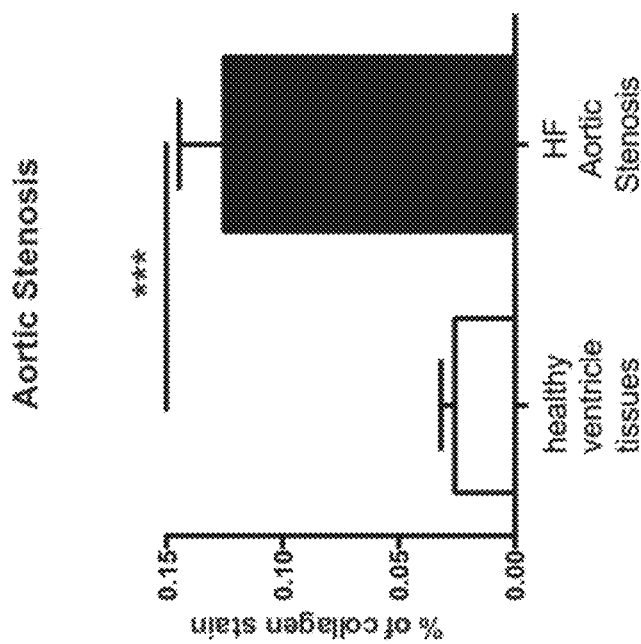

FIGS. 3A-3K. T cell infiltrate in failing left ventricle. (FIG. 3A) Representative immunohistochemical (IHC) staining of left ventricles for the T cell marker CD3e (brown coloration) in sham and TAC mice at 4 weeks. Original magnification 10×; bars=200 µm. (FIG. 3B) Summary of IHC analysis. Values are mean±SEM (n=6). Unpaired t-test: **, p-value<0.01. (FIG. 3C) Staining for the T cell marker CD3e (brown coloration) in TAC-operated mice, 1 week post-operation. Original magnification 10×; bar=200 µm (FIG. 3D) Representative FACS analysis of CD3e+ cells, enriched on a Lympholyte-M gradient from a cardiac cell suspension from mice 1 week after TAC. (FIG. 3E) Mediastinal (heart-draining) lymph nodes, inguinal lymph nodes and spleens were collected 2 days after TAC or sham-operation, stained and analyzed by flow cytometry. The mean fluorescence intensities of CD25 on $CD3e^+$ cells are plotted as mean±SEM; sham (white bars), TAC (black bars) (n=4). Unpaired t-test *, p-value<0.05. (FIG. 3F) Representative Azan's trichrome staining of cardiac biopsies from healthy ventricle tissue donors (n=3), from patients with dilated cardiomyopathy due to a mutation in lamin A/C, prior to placement of a Left Ventricular Assist Device (HF LVAD 1M) (n=4), and from patients with severe dilated cardiomyopathy due to a mutation in lamin A/C and a mutation in titin, prior to placement of a Left Ventricular Assist Device (HF LVAD 2M) (n=2). Blue (darker) areas indicate collagen deposition (original magnification, 20×; bar=100 µm). (FIG. 3G) Statistical analysis of collagen deposition in identical regions of interest. Values are mean±SEM. Fisher's exact test for the presence versus absence of fibrosis: *, p-value<0.05; **, p-value<0.01. The amount of collagen was also positively associated with the degree of HF (one-way ANOVA with post-test for linear trend: p<0.001). (FIG. 3H) Representative staining for the T cell marker CD3e (brown coloration; i.e. the brown/darker spots in right-hand panel "severe heart failure") on the same samples as in (FIG. 3F). (FIG. 3I) Statistical analysis of CD3e IHC. Values are mean±SEM. One-way ANOVA with Dunn's post-test: *, p-value<0.05. (FIG. 3J) Statistical analysis of collagen deposition, in identical regions of interest, in cardiac biopsies from healthy ventricle tissues (n=3) and patients with HF due to aortic stenosis (n=2) stained with Azan's trichrome. Values are mean±SEM. Healthy ventricle tissues (white bar), HF with aortic stenosis (black bars). Fisher's exact test for the presence versus absence of fibrosis: ***, p-value<0.001. (FIG. 3K) Statistical analysis of CD3e IHC analysis on the same samples as in (FIG. 3J). Healthy ventricle tissues (white bar), HF due to aortic stenosis (black bars). Values are mean±SEM. Mann-Whitney test; *, p-value<0.05.

FIGS. 4A-4H. Abatacept blunts the progression of cardiac dysfunction in pressure-overloaded mice. Mice underwent TAC or sham operation; 2 days post-operation, the mice were treated with three intraperitoneal injections per week of 200 µg of abatacept or PBS, for 4 weeks. (FIG. 4A) Fractional shortening (% FS), (FIG. 4B) ejection fraction (% EF), (FIG. 4C) left ventricle internal dimension in diastole (LVIDd), and (FIG. 4D) left ventricle internal dimension in systole (LVIDs) in TAC- and sham-operated mice at baseline and at time points 1, 3, and 4 weeks after operation, with and without abatacept administration. Data show the mean % FS, % EF, LVIDd, and LVIDs for each experimental group at all time-points±SEM (n=7-9). Two-way ANOVA with Bonferroni post-test: p-values shown in the panel. Abatacept ameliorates pressure overload-induced cardiac fibrosis in mice. (FIG. 4E) Representative macroscopic images of the heart of untreated, PBS-treated, and abatacept-injected mice 4 weeks post-sham- or TAC (scale bar=2 mm). (FIG. 4F) Cardiac sections of untreated, PBS-treated or abatacept-treated, TAC- or sham-operated mice, at 4 weeks post-operation were stained with Azan's trichrome (n=2). Five identical regions of interest (ROIs) were applied to all samples. The collagen staining intensity was quantified by image acquisition software; plot points indicate the % of collagen pixels in each ROI. Red bars indicate the mean % collagen in each experimental group. ROIs with a collagen signal higher than zero were considered fibrotic. Fisher's exact tests for the presence or absence of fibrosis were applied to sham versus TAC-operated groups for each treatment category. The dotted red line separates fibrotic from non-fibrotic ROIs. *, p-value<0.05. (FIGS. 4G-4H) Mice underwent TAC, 2 weeks post-operation, the mice were treated with three intraperitoneal injections per week of 200 µg of abatacept or PBS, for 2 weeks. (FIG. 4G) Fractional shortening (% FS) and (FIG. 4H) ejection fraction (% EF) were measured at baseline and at 2 and 4 weeks after operation. Data show mean of % FS and % EF for each experimental group at all time-points±SEM (n=7). Two-way ANOVA with Bonferroni post-test: ***, p-value<0.001.

FIGS. 5A-5F. Abatacept administration suppresses the immune response in TAC-operated mice. (FIG. 5A) Mediastinal (heart-draining), inguinal lymph nodes and spleens were collected 1 week after TAC or sham-operation, stained and analyzed by flow cytometry. Percentage of CD25+ out of CD3e+ cells are plotted as mean±SEM; sham (white bars), TAC abatacept (grey bars) and TAC PBS (black bars) (n=3-4). One-way ANOVA with Tukey's post-test: *, p-value<0.05; , p-value<0.01, *, p-value<0.001. (FIG. 5B) Statistical analysis of immunohistochemical staining of left ventricles for the T cell marker CD3e in TAC mice at 4 weeks post-operation, treated with abatacept or PBS, and representative images of the staining (brown coloration; original magnification 40×; scale bar=50 µm). Number of CD3e+ cells is plotted as mean±SEM; TAC abatacept (white bars); TAC PBS (black bars). Unpaired t-test; *, p-value<0.00 (n=2). (FIG. 5C) Statistical analysis of immunohistochemical staining of left ventricles for the macrophage marker AIF-1 in TAC mice at 1 week post-operation, treated with abatacept or PBS, and representative images of the staining (brown coloration; original magnification 20×; scale bar=100 µm). AIF-1 density plotted as mean±SEM; TAC abatacept (white bars); TAC PBS (black bars). Unpaired t-test; **, p-value<0.001 (n=2). (FIG. 5D) Gene expression analysis (TaqMan real-time qPCR) of the left ventricle of C57BL6/J mice, 1 week after TAC or sham operation, with abatacept or PBS treatment. Bars show relative mean Il6 and Il10 expression, internally normalized to 18s rRNA expression. Values are mean±SEM (sham n=5; TAC n=8). One-way ANOVA, Dunn's post-test: *, p-value<0.05; n.s., not significant. (FIGS. 5E-5F) Cardiac single cell suspensions of TAC operated mice, 1 week after the operation, were stained and analyzed by flow cytometry. Percentage of F4-80+ Ly6C+ out of CD11b+ CD45+ live cells (FIG. 5E) and F4-80+ Ly6C– out of CD11b+ CD45+ live cells (FIG. 5F) are plotted as mean±SEM; TAC abatacept (black circles); TAC PBS (black squares). Unpaired t-test; *, p-value<0.05; **, p-value<0.01 (n=4, 3).

Figure 6A:
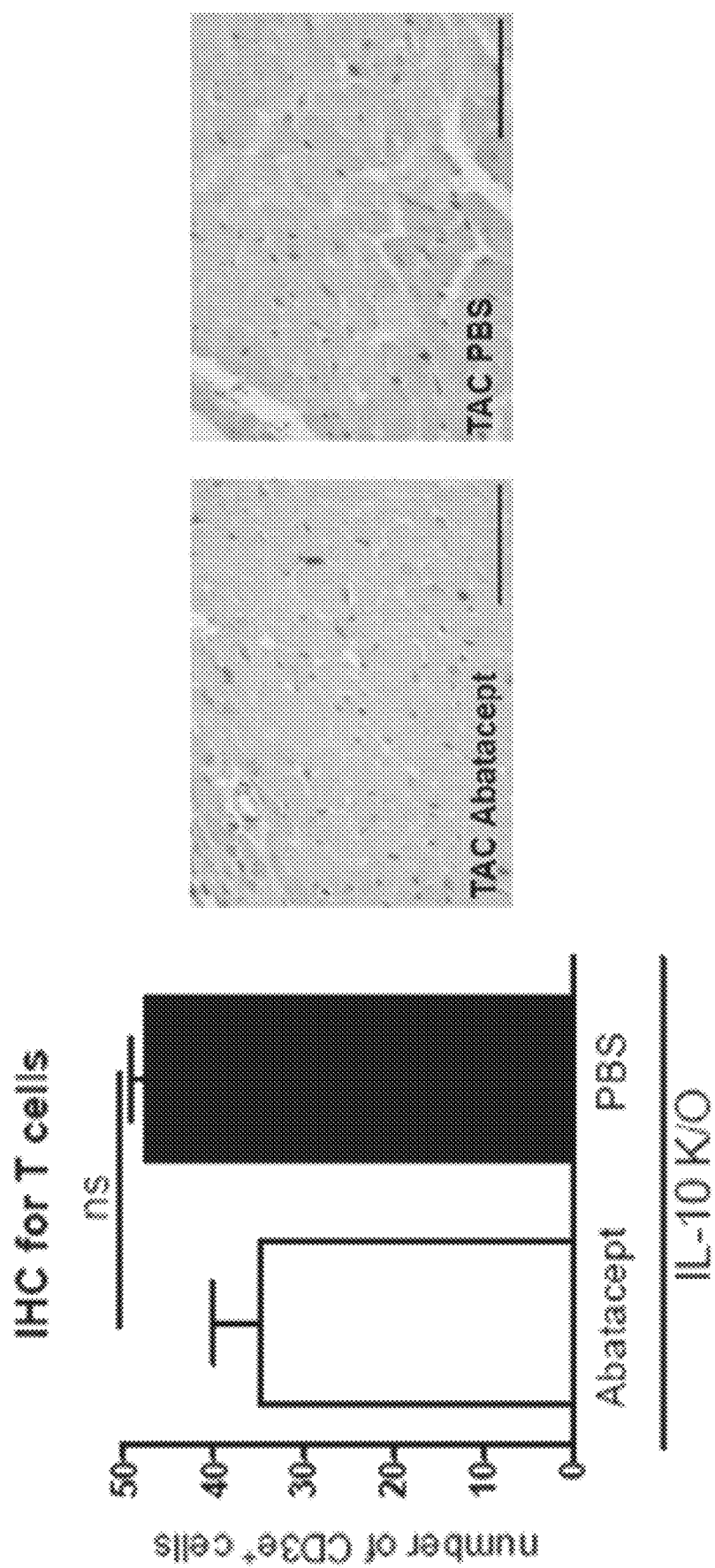
Figures 6D, 6E:
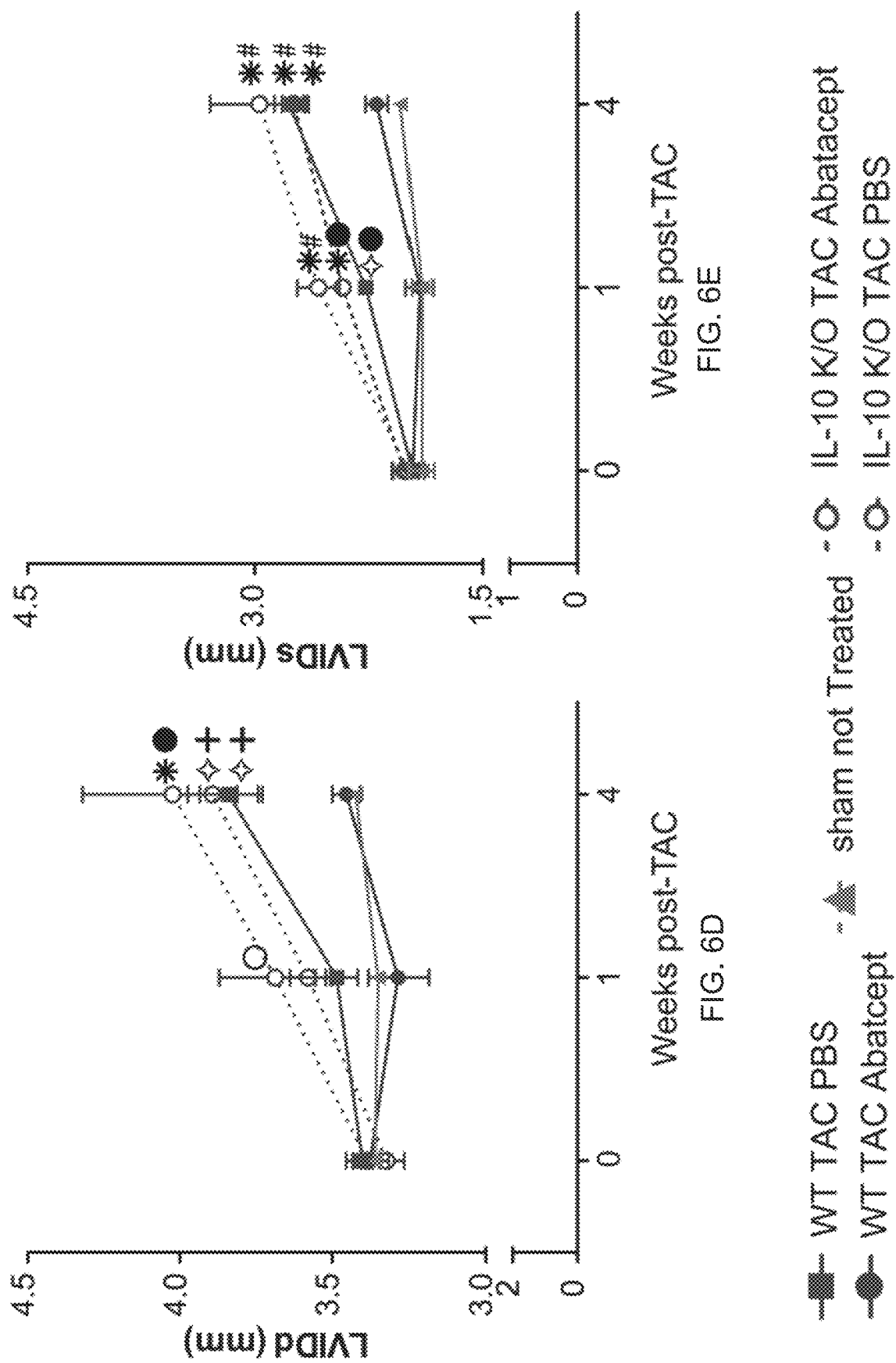

FIGS. 6A-6H. Abatacept attenuates HF through the action of IL-10. (FIG. 6A)

Immunohistochemical staining of left ventricles for the T cell marker CD3e in TAC-operated IL-10 K/O mice treated with abatacept or PBS, at 4 weeks post-operation. Values show mean±SEM (n=2). Unpaired t-test; not significant (ns). Representative staining for the T cell marker CD3e (brown coloration; image acquisition with 40× magnification; scale bar=50 µm). (FIGS. 6B-6E) Heart functionality is not preserved in IL-10 K/O TAC mice after abatacept treatment. Mice underwent TAC or sham operation; 2 days post-operation, the mice were treated with three intraperitoneal injections per week of 200 µg of abatacept or PBS, for 4 weeks. (FIG. 6B) Fractional shortening (% FS). (FIG. 6C) Ejection fraction (% EF). (FIG. 6D) Left ventricle internal dimension in diastole (LVIDd). (FIG. 6E) Left ventricle internal dimension in systole (LVIDs). Data show mean±SEM (n=5-9). Two-way ANOVA with Bonferroni post-test; ○, p-value<0.05 versus TAC WT abatacept; ✧, p-value<0.01 versus TAC WT abatacept; ✱, p-value<0.001 versus TAC WT abatacept; +, p-value<0.05 versus sham not-treated; ●, p-value<0.01 versus sham not-treated; #, p-value<0.001 versus sham not-treated; §, p-value<0.01 versus TAC WT PBS. (FIG. 6F) Abatacept treatment in the presence but not in the absence of IL-10 reduces cardiomyocyte apoptosis in TAC-operated mice.

TUNEL assay staining in slides for the assessment of cardiomyocyte apoptosis was performed on hearts of treated mice 4 weeks after TAC operation, in both wild type and IL10K/O mice. Bars show mean±SEM of TUNEL-positive cells (n=2); white bars, abatacept-treated TAC-operated mice; black bars, PBS-treated TAC-operated mice. Two-way ANOVA with Bonferroni post-test; *, p-value<0.05. (FIGS. 6G-6H) Wild-type B cell but not T cell transfer in IL-10KO TAC-operated mice restores abatacept therapeutic effects. IL-10KO mice received wild-type T or B cells. Subsequently, they underwent TAC or sham operation; 2 days post-operation, the mice were treated with three intraperitoneal injections per week of 200 µg of abatacept or PBS, for 1 week. (FIG. 6G) Fractional shortening (% FS) and (FIG. 6H) ejection fraction (% EF) were measured at baseline and at 1 week after operation. Data show the mean % FS and % EF for each experimental group at all time-points±SEM (n=3-7). Two-way ANOVA with Bonferroni post-test, *, statistics for IL10 KO TAC abatacept; +, WT B cells; #, statistics for WT TAC abatacept; §, statistics for sham not treated.

Figure 7A:
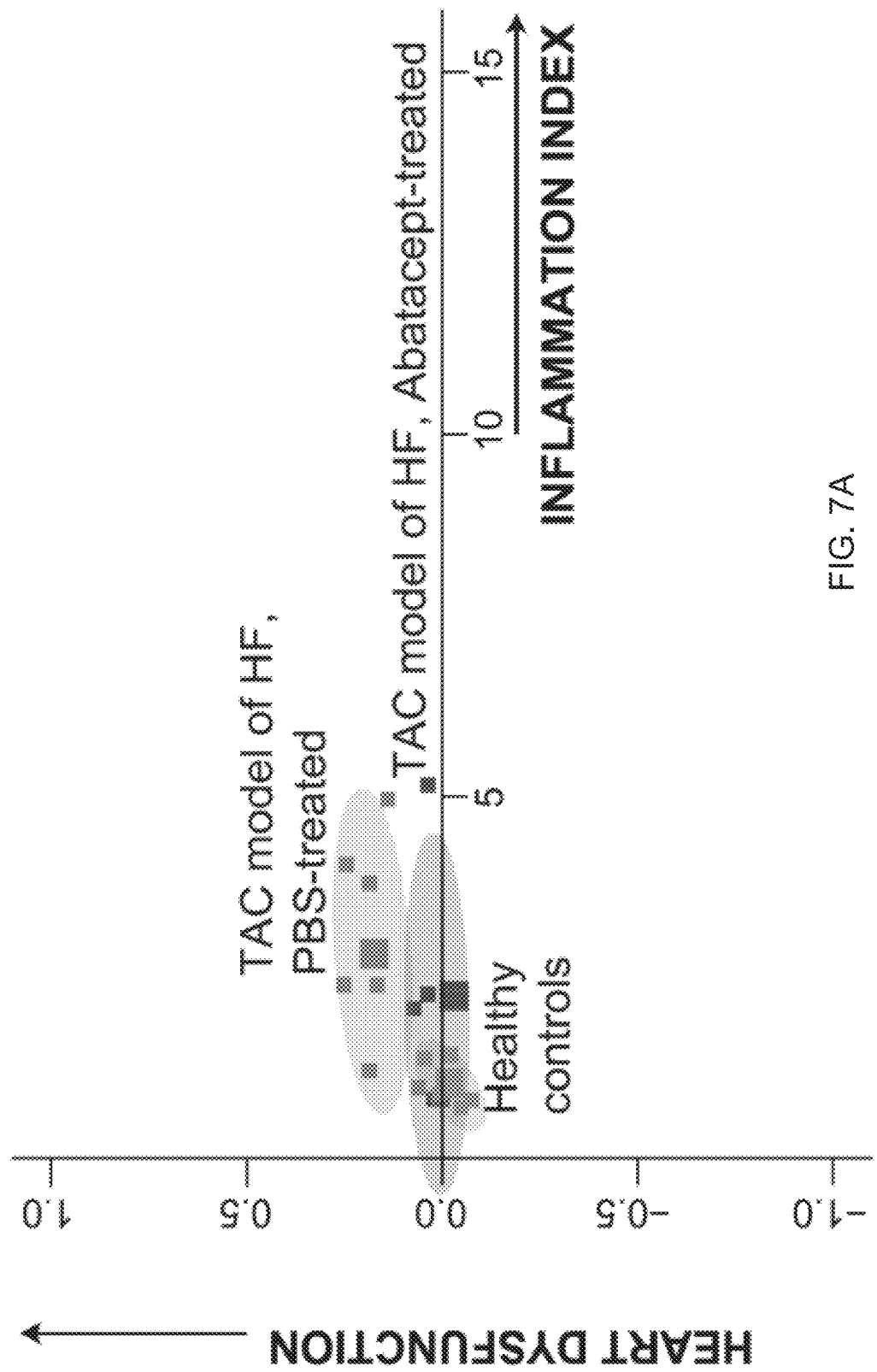
Figure 7B:
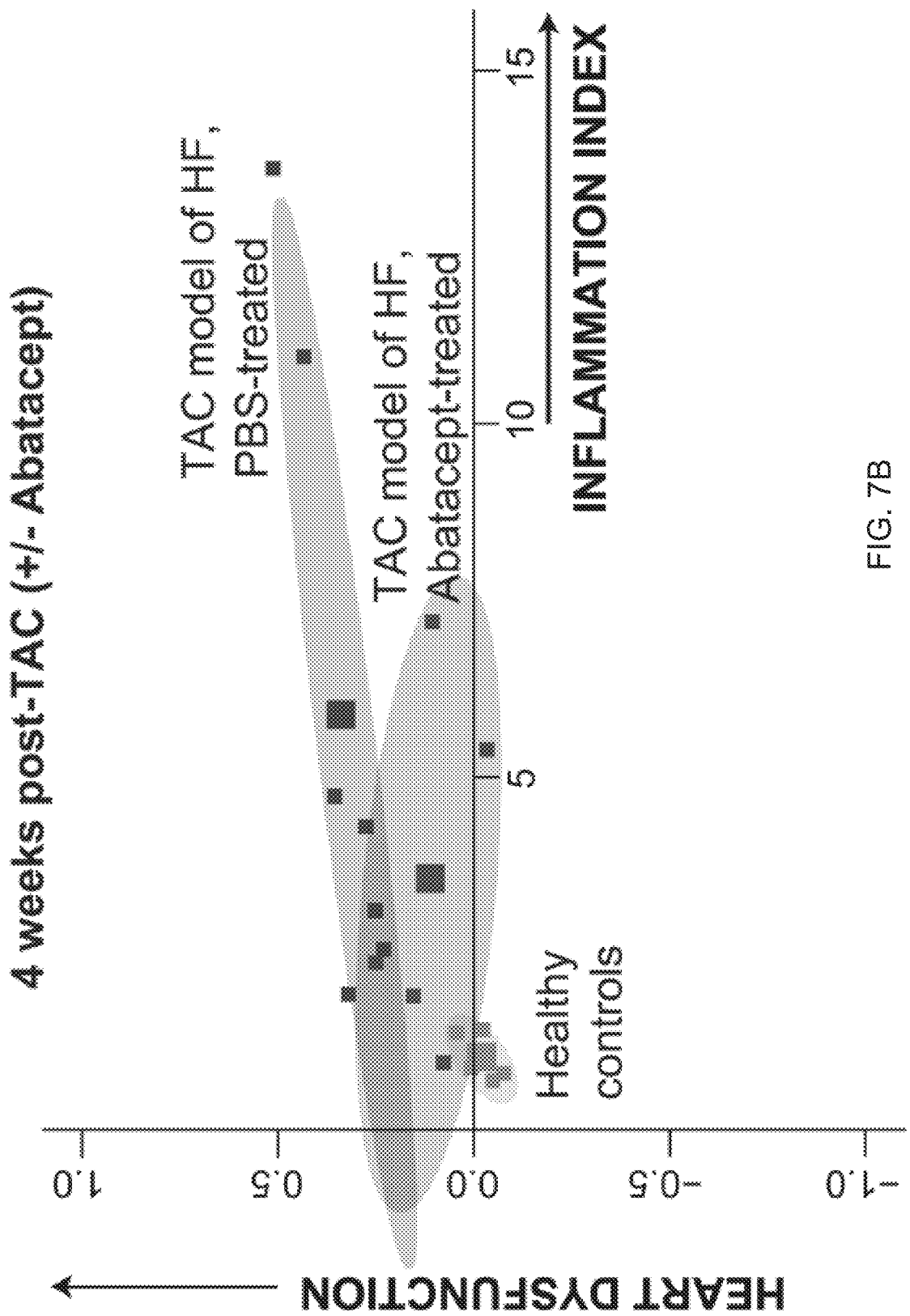
Figure 7C:
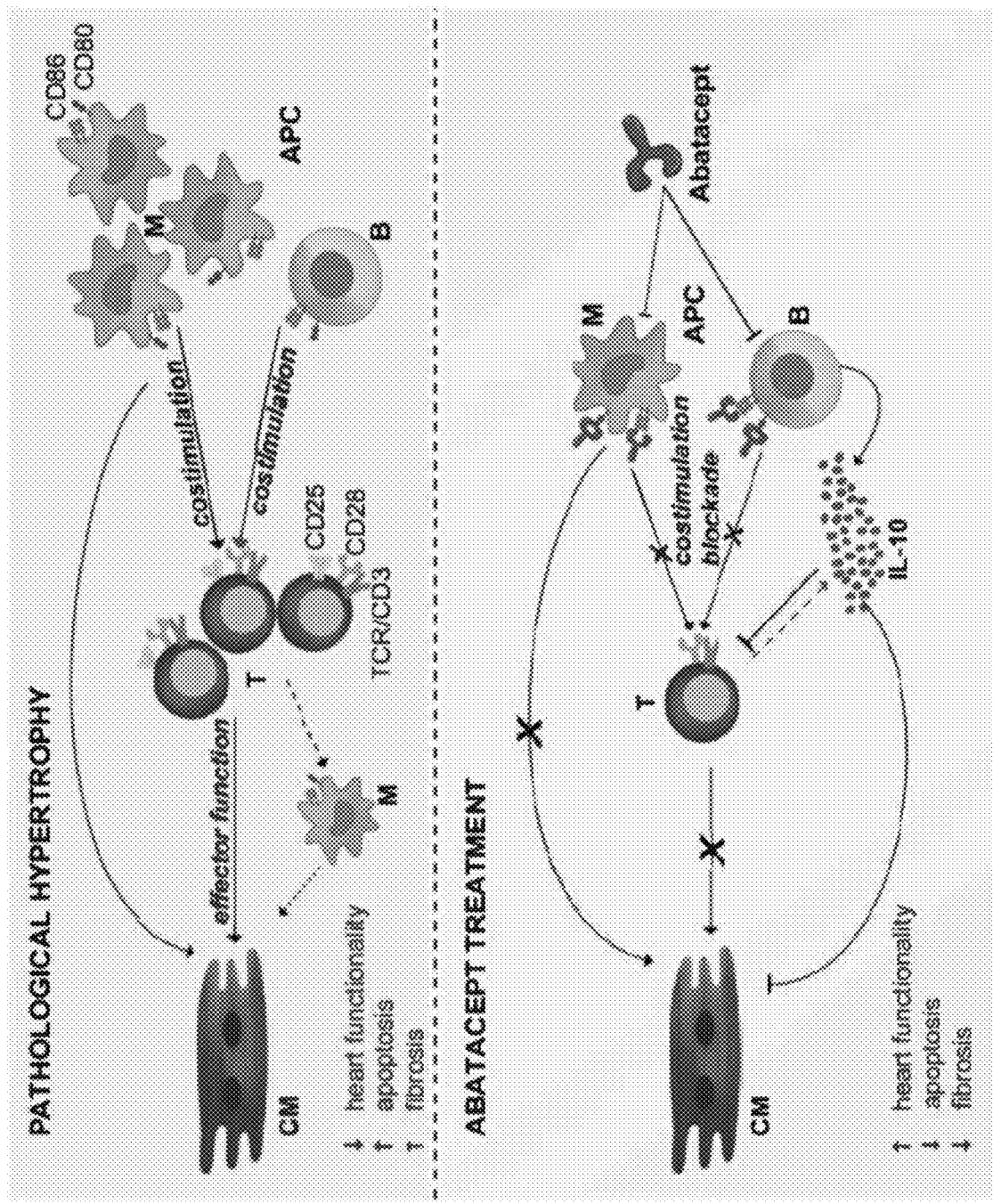

FIGS. 7A-7C. Abatacept blunts cardiac dysfunction by suppressing the immune response (FIG. 7A, 7B) Heart dysfunction index (HDI) (y axis) versus an index of inflammation (x axis), calculated as for FIG. 2. Each point represents data from one mouse. Large points represent the mean of each group, whereas the shaded ellipses represent one standard deviation from the mean. The following groups were used as matching controls for the experimental sets: for TAC-operated abatacept- or PBS-treated mice at 1 week (FIG. 7A) or 4 weeks (FIG. 7B) post-operation: sham-operated abatacept or PBS-treated mice, prior to operation (basal reading); for healthy (sham-operated PBS-treated): sham operated PBS-treated prior to operation (basal reading). (FIG. 7C) Schematic cartoon of the mechanism of action of abatacept in heart failure, CM: Cardiomyocyte, T: T cell, MΦ: Macrophage; APC: Antigen Presenting Cell. In pathological hypertrophy, T cells are activated (through their TCR) and receive costimulation via CD28 from CD80/CD86-expressing antigen presenting cells (macrophages, B cells, dendritic cells). The full activation of T cells, identified by high levels of CD25, enhances the chronicity of the cardiac inflammatory response. This also involves the proinflammatory action of cardiac macrophages. As a result, there is increased cardiomyocyte apoptosis, fibrosis and reduced heart functionality. During abatacept treatment, the drug blocks CD80/CD86-mediated costimulation by macrophages and B cells, leading to inhibition of T cell activation, proliferation and/or infiltration. The effects on macrophages (which may be both direct and indirect) lead to lower maturation and infiltration. Direct effects on B cells lead to production of anti-inflammatory cytokine IL-10, which may also be produced to a lesser extent by T cells. As a consequence of the effect on T cells, B cells and macrophages, the progression of cardiac pathology is blocked, even if the drug is administered at a late stage. The protective effect is dependent on IL-10 presence.

FIGS. 8A-8D. Immune mediators are absent in models of physiological hypertrophy (FIGS. 8A-8B) Gene expression analysis of mediators of inflammation in the left ventricle of exercise-trained mice (running) compared to sedentary mice (sedentary). Bars show relative mean mRNA expression, internally normalized to 18s rRNA expression. The expression of Tnfa, Il6, Ccl4, Ccl5, Cxcl10, Cxcl11, Il4, Itgam (CD11b), or Cd3e did not change significantly, whilst Ccl2 significantly decreased in the trained mice group. Values are mean±SEM (n=3). Unpaired t-test: *, p-value<0.05. (FIGS. 8C-8D) Gene expression analysis of inflammatory mediators by TaqMan real-time qPCR in the left ventricle of 8-week-old Akt transgenic mice (Akt-Tg, white) (n=6) compared to wild-type mice (WT, black) (n=7). Bars show relative mean mRNA expression internally normalized to 18s rRNA expression. The relative expression of Tnfa, Il6, Il1b, Tgfb1, Ccl2, Cxcl11, and the innate cell marker Itgam (CD11b) did not increase, whilst Ccl4, Ccl5, Cxcl10, Il4, and Cd3e increased significantly. Values are indicated as mean±SEM. Mann-Whitney test: *, p-value<0.05; **, p-value<0.01.

FIGS. 9A-9F. The progression of cardiac hypertrophy in the heart is limited by abatacept. (FIG. 9A) Heart weight body weight (mg/g), (FIG. 9B) left ventricle body weight (mg/g), (FIG. 9C) heart weight tibia length (mg/cm) ratios in TAC-operated mice treated with abatacept or PBS, 4 weeks post operation. Values are indicated as mean±SEM (n=5-7). Unpaired t-test: *, p-value<0.05. Relative gene expression by real-time qPCR internally normalized to 18S for genes expressing (FIG. 9D) β-myosin (Mhy7), (FIG. 9E) brain natriuretic peptide (Nppb) and (FIG. 9F) atrial natriuretic factor (Nppa) in the same mice. Values are mean±SEM (n=5-8). Two-way ANOVA with Bonferroni post-test; *, p-value<0.05; **, p-value<0.01.

FIGS. 10A-10H. Heart functionality is unchanged in non-operated mice after abatacept or human IgG isotype treatment. (FIG. 10A) Fractional shortening (% FS) and (FIG. 10B) ejection fraction (% EF) in non-operated mice treated with abatacept or human IgG isotype control, or sham-operated, non-treated mice (included for comparison). Values are mean±SEM (n=3-5). Two-way ANOVA with Bonferroni post-test; no significant differences observed. (FIG. 10C) Fractional shortening (% FS), (FIG. 10D) ejection fraction (% EF), (FIG. 10E) left ventricle internal dimension in systole (LVIDs) and (FIG. 10F) left ventricle internal dimension in diastole (LVIDd) in TAC-operated mice treated with abatacept, PBS or human IgG isotype control for 1 week starting 2 days after operation. Values are mean±SEM (n=6-9). Two-way ANOVA with Bonferroni post-test; *, p value<0.05; , p value<0.01; *, p value<0.001. (FIG. 10G) left ventricle internal dimension in systole (LVIDs) and (FIG. 10H) left ventricle internal dimension in diastole (LVIDd) in TAC-operated mice treated with abatacept or PBS for 2 weeks starting 2 weeks after operation. Values are mean±SEM (n=7-9). Two-way ANOVA with Bonferroni post-test; *, p value<0.05.

FIGS. 11A-11B. Abatacept attenuates T cell responses in vitro and induces IL-10 production. (FIG. 11A) Total splenocytes of 8 week-old C57BL/6J mice activated with anti-CD3 and cultured with 20 µg/ml abatacept or IgG isotype control for 72 hours were analyzed by FACS for CD3e expression. Bars show mean±SEM of 4 independent experiments (n=4). One way-ANOVA repeated measures test with Tukey's post-test; *, p-value<0.05; ***, p-value<0.001. (FIG. 11B) Total splenocytes were then analyzed for IL-10 production. Specific population frequencies were analyzed among the IL-10-expressing splenocytes (CD19+ B cells, CD11c+ dendritic cells, CD11b+ monocytes and myeloid-derived cells, F4/80+ macrophages, CD3e+ T cells, and CD3e+ Foxp3+ Treg cells). Bars show mean±SEM of 3 independent experiments (n=3).

FIG. 12. Presence of regulatory T cells in TAC- and sham-operated mice. Gene expression analysis by real-time TaqMan qPCR for the regulatory T cell marker Foxp3 in the left ventricle of C57BL6/J mice, 1, 4, and 8 weeks after TAC or sham operation. Bars show mRNA expression internally normalized to 18s rRNA expression. Values show mean±SEM (n=7-9). Two-way ANOVA with Bonferroni post-test; *, p-value<0.05.

Figure 13:
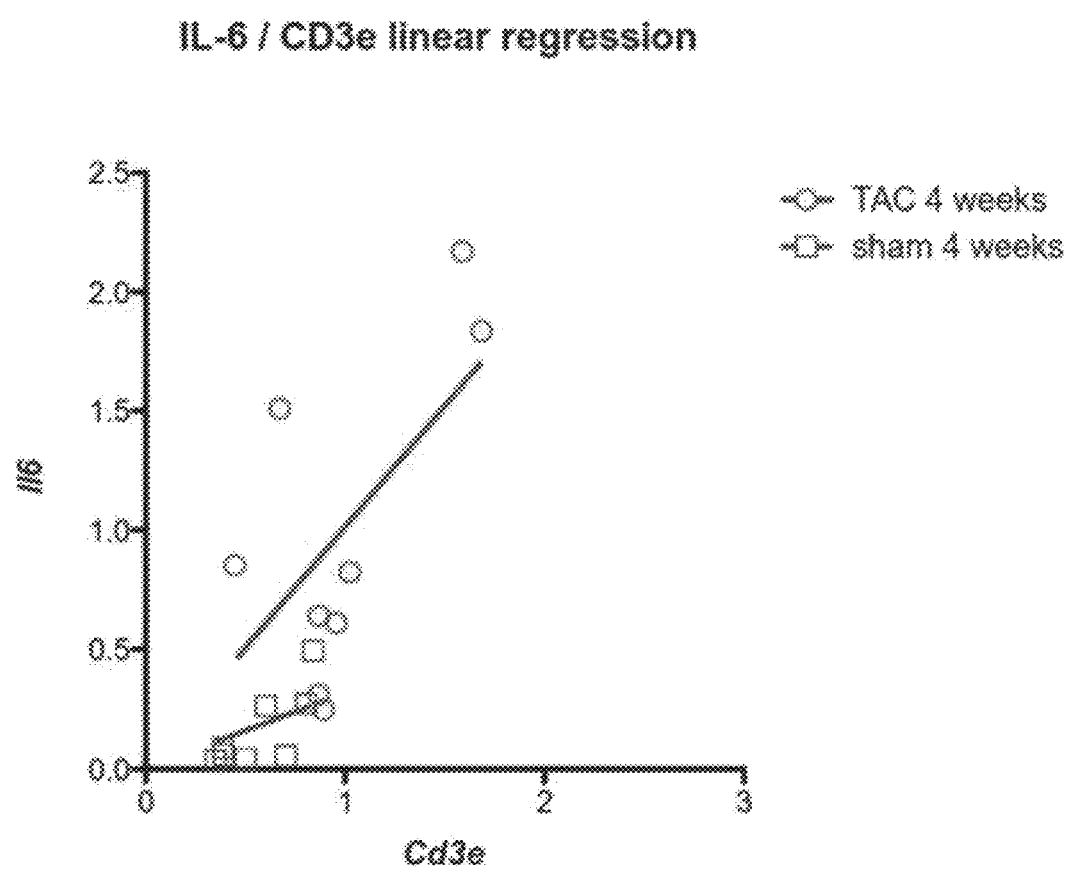

FIG. 13. Linear regression of IL-6 and CD3e mRNA expression in left ventricles of TAC and sham-operated mice. circles and corresponding regression line: Linear regression between Cd3e and Il6 expression in left ventricle of C57BL6/J TAC-operated mice 4 weeks after operation (n=9). Linear regression test; p value=0.0002. squares and corresponding regression line: Linear regression between Cd3e and Il6 expression in left ventricle of C57BL6/J sham-operated mice 4 weeks after operation (n=7). Linear regression test; p value=0.0037.

Figure 14:
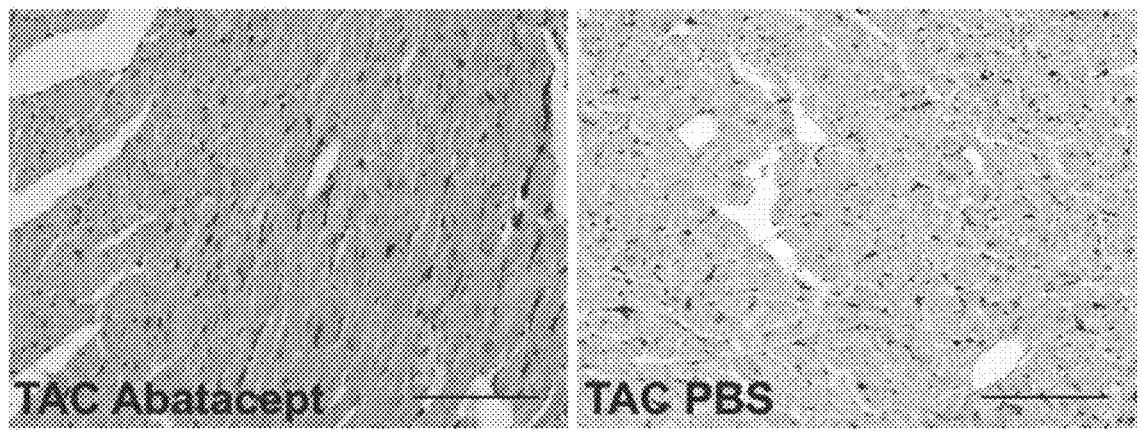
Figure 14:
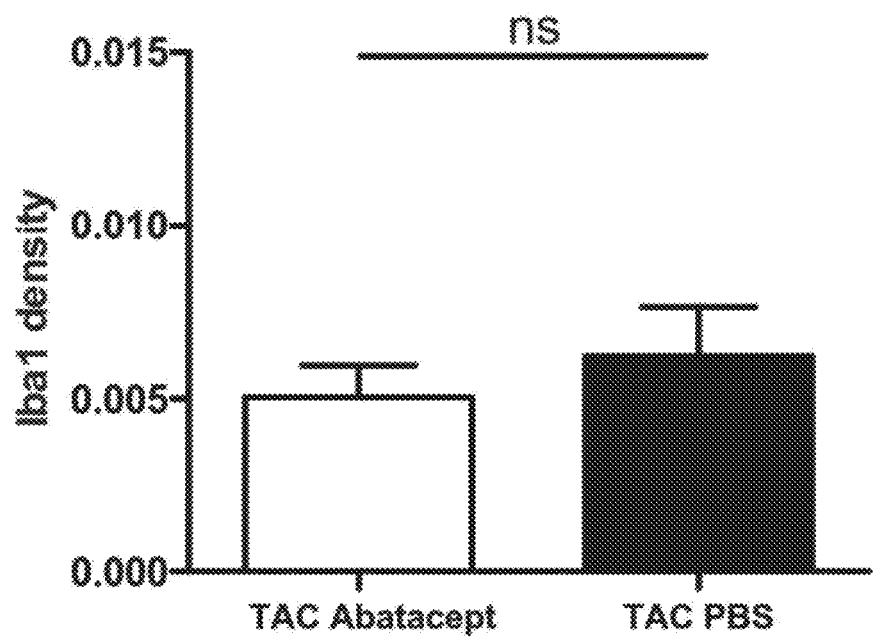
Figure 15A:
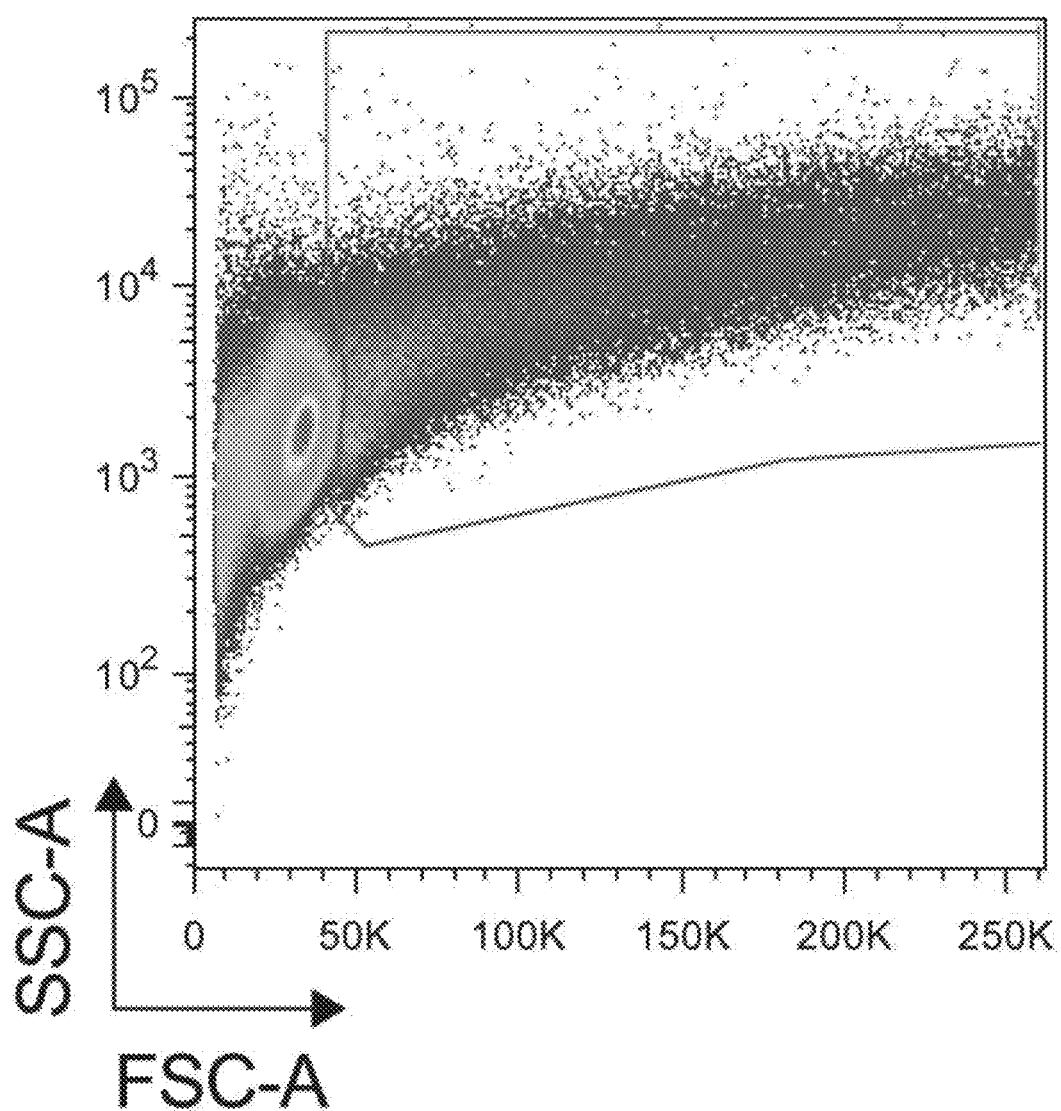
Figure 15B:
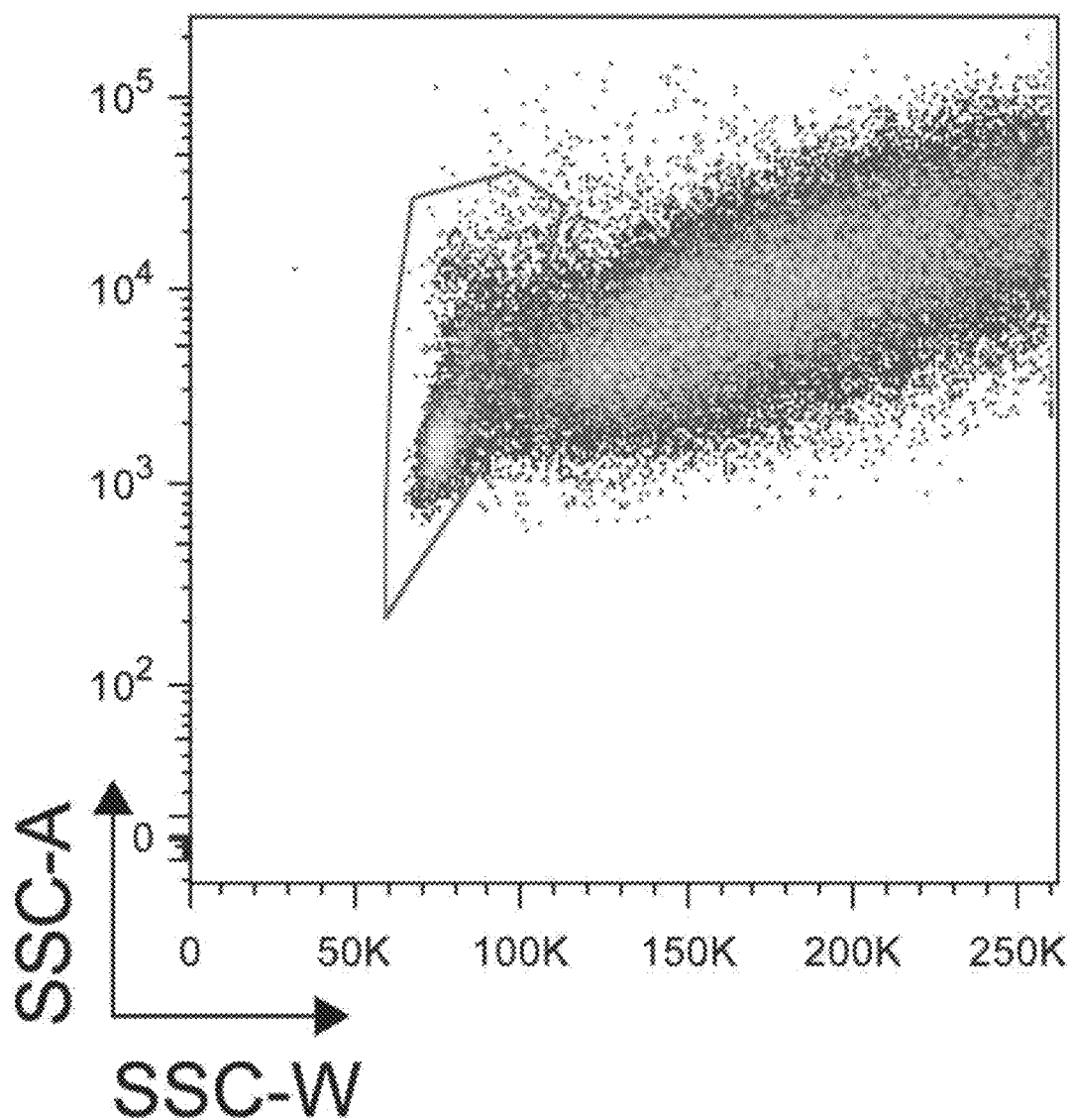
Figure 15C:
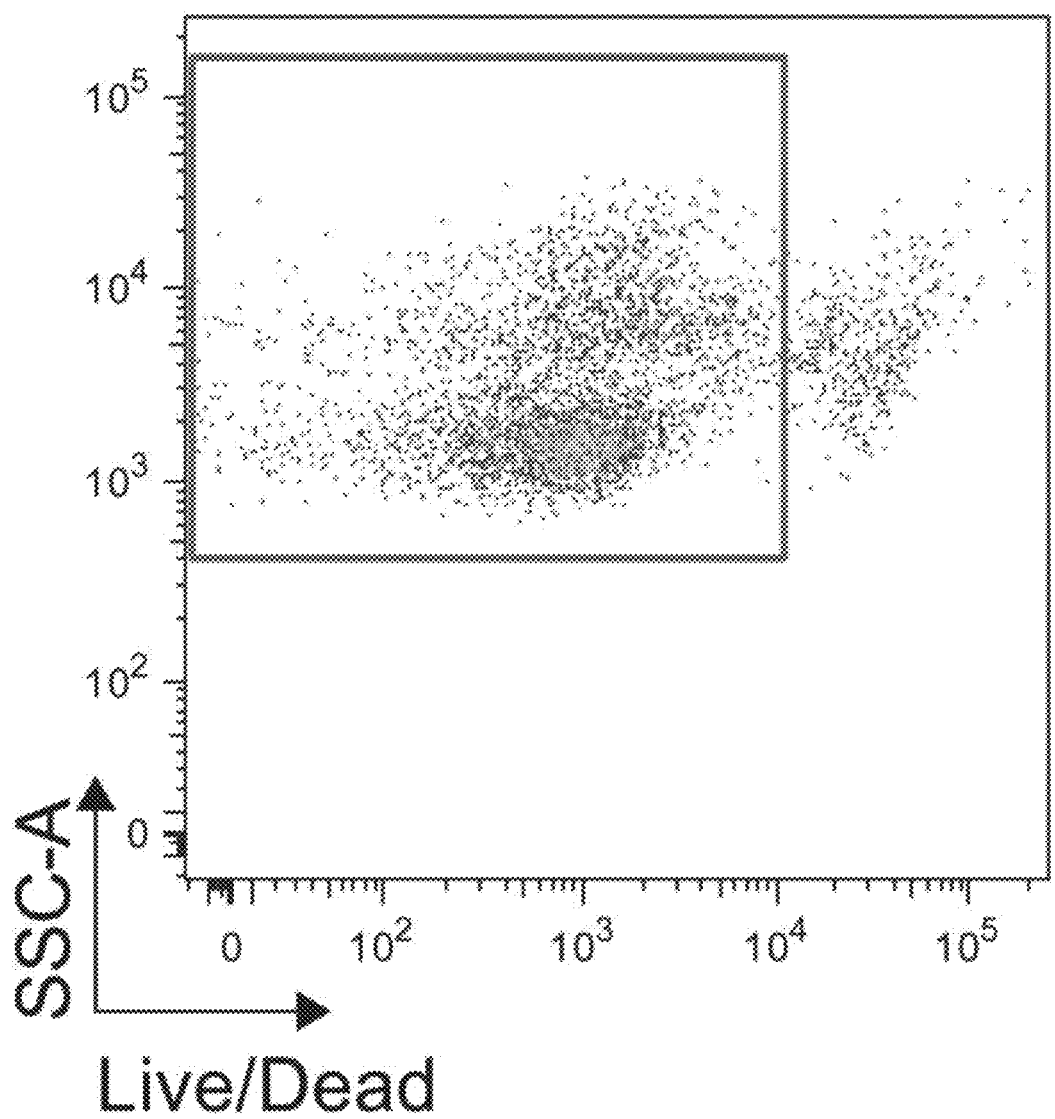
Figure 15D:
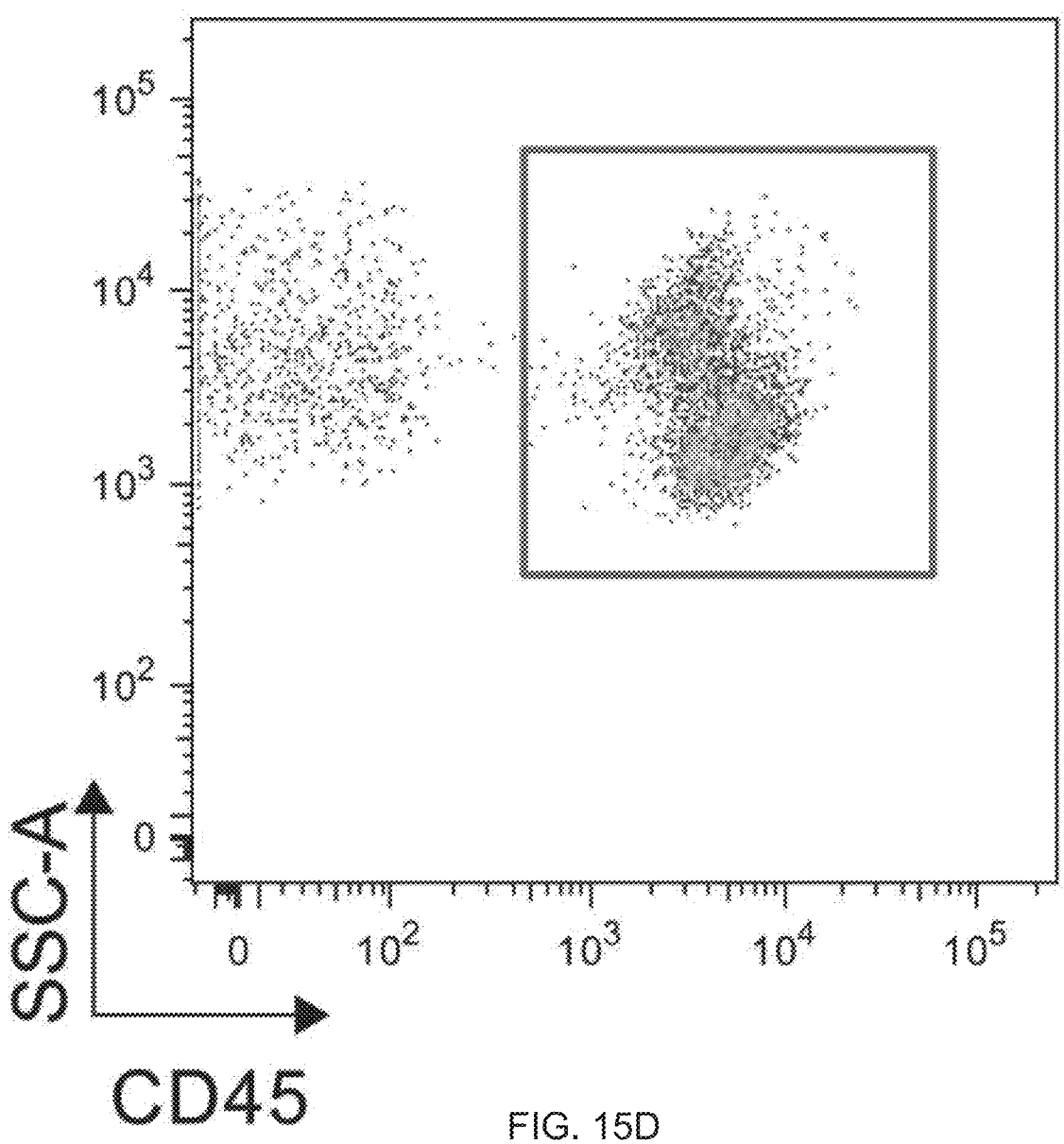
Figure 15E:
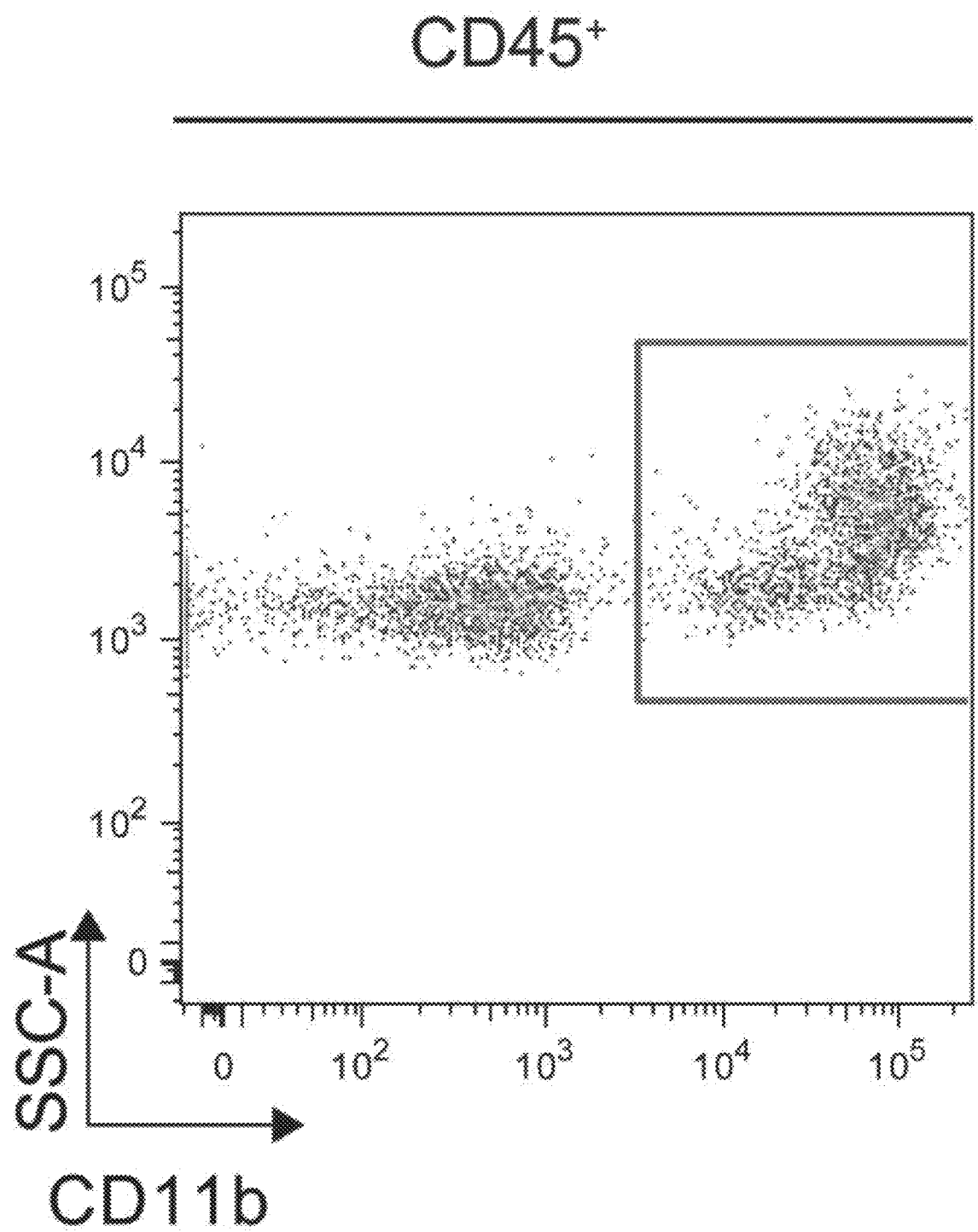
Figure 15F:
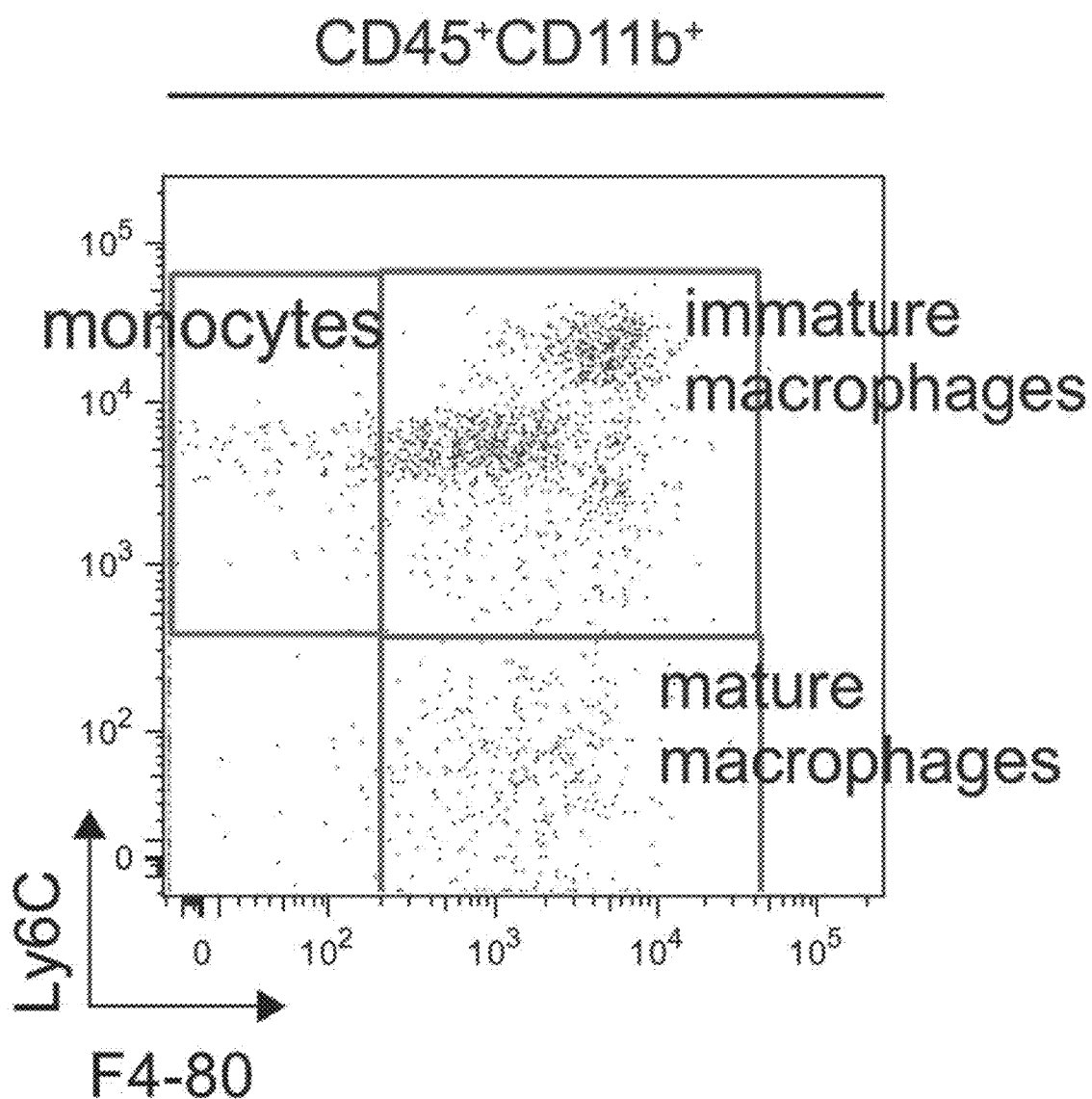

FIG. 14. Representative images and statistical analysis of AIF-1 immunohistochemical staining (brown coloration; original magnification 20×; scale bar=100 μm) in left ventricles of TAC mice at 4 weeks post-operation, treated with abatacept or PBS. AIF-1 density plotted as mean±SEM; TAC abatacept (white bars); TAC PBS (black bars). Unpaired t-test. (n=2).

FIGS. 15A-15F. Gating strategy for flow cytometry analysis of cardiac single cell suspensions from TAC operated mice 1 week after operation, corresponding to data in FIGS. 5E, 5F. Cells were gated based on forward and side scatter, doublets were excluded and live single cells were gated. CD45 and CD11b-expressing cells were selected and identified on the basis of Ly6C and F4-80 expression: Ly6C$^+$ F4-80$^-$ monocytes, Ly6C$^+$ F4-80$^+$ immature macrophages and Ly6C$^-$ F4-80$^+$ mature macrophages.

Figure 16:
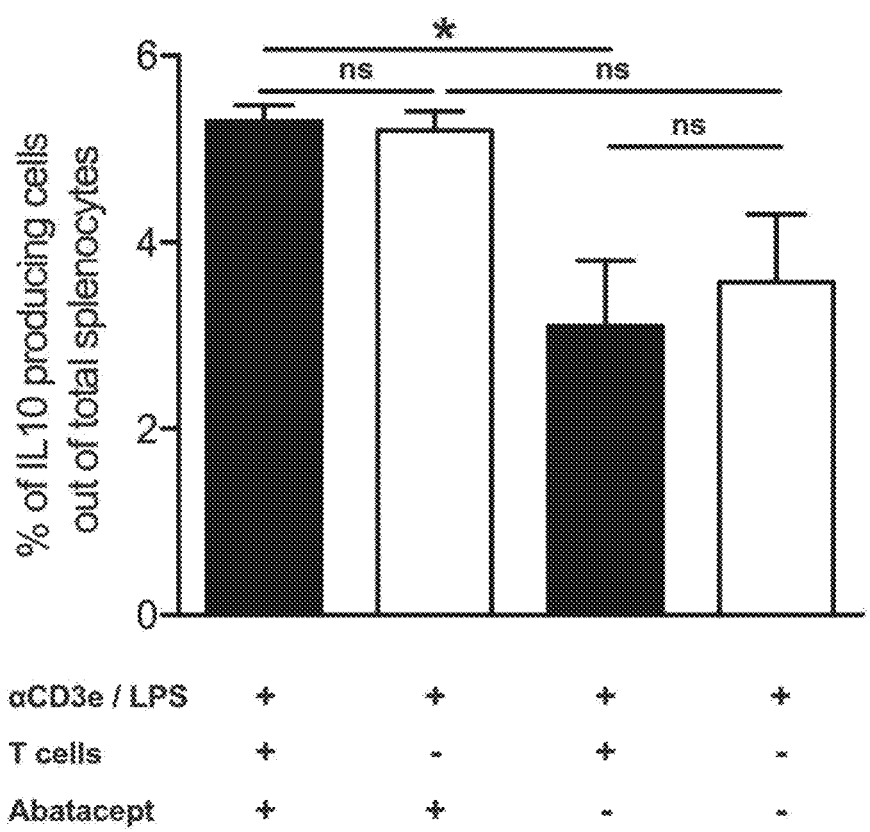

FIG. 16. Total splenocytes or T cell-depleted splenocytes of 8 week-old C57BL/6J mice were activated with 2 μg/ml anti-CD3 and 5 μg/ml of LPS. After 48 hours in culture with or without 20 μg/ml abatacept were analyzed by flow cytometry for IL-10 production. Bars show mean±SEM of 3 independent experiments (n=3) of the percentage of IL10 producing cells out of total splenocytes. One way-ANOVA repeated measures test with Tukey's post-test; *, p-value<0.05.

EXAMPLES

Materials and Methods

Animals: All procedures were performed in compliance with national and EU legislation, and institutional regulations.

Transverse aortic constriction (TAC): Procedures where performed according to (Condorelli et al., 2001). TAC was performed on 8-10-week-old male C57BL/6J mice (Charles River, France) and on 8-10-week-old male C57BL/6J IL-10-/- mice (Jackson Laboratories, US). All animals were screened prior to operation via echocardiography to establish their baseline. Mice were anaesthetized by intraperitoneal injection of a mixture ketamine (100 mg/kg) and xilazine (10 mg/kg). The chest cavity was opened by a small incision at the level of the first intercostal space. After isolation of the aortic arch, a 8-0 Prolene suture was placed around the aorta and a 27G needle was laced in between. The needle was immediately removed to produce an aorta with a stenotic lumen. The chest cavity was then closed with one 6-0 nylon suture and all layers of muscle and skin closed with 6-0 continuous absorbable and nylon sutures, respectively. A sham group, undergoing surgery without aortic banding, was used as control.

Echocardiography: A Vevo 2100 high-resolution in vivo imaging system (VisualSonics Fujifilm) with a MS550S probe "high frame" scanhead was used for echocardiographic analysis. Mice were anesthetized with 1.0% isoflurane for M-mode imaging. Pressure gradients (60 to 90 mm Hg), an index of biomechanical stress, were determined by echo Doppler on all animals that underwent TAC surgery.

Abatacept treatment: Starting on day 2 or 2 weeks of TAC/sham surgery, mice were intraperitonally injected with either 100 μl PBS or 200 μg CTLA-4 Ig (Abatacept) in 100 μl of PBS, three times a week for 4 weeks.

Abatacept is a human CTLA-4-Ig fusion, though due to the high (75%) similarity between human and mouse CTLA-4, it also functions in mouse. Abatacept generally has in vivo efficacy in mouse (in various pathological contexts) using doses in the range of, e.g., 100-400 μg/mouse. It may be administered every 2 days. 200 μg/mouse every 2 days is (at about 8 mg/kg) similar to the human dose used in Rheumatoid Arthritis patients (8-10 mg/kg). This dose is therefore "translationally relevant", and has been used herein.

Adoptive transfer of wild-type T and B cells in IL10 KO mice: Wild-type B and T cells were isolated from C57BL6/J male mice respectively with B Cell Isolation Kit and Pan T Cell Isolation Kit II (Miltenyi Biotec) on an AutoMACS. Purity was assessed by staining with anti-mouse CD3ε (145-2C11, BioLegend) or anti-mouse CD19 (eBio1D3, eBioscience), and analyzed by flow cytometry. C57BL6/J IL-10 KO male mice, prior to basal echocardiography screening, were injected intravenously with $2 \cdot 10^6$ WT T or B cells. Mice underwent TAC surgery and were injected with abatacept starting on day 2 after surgery.

Human biopsies: The severe cardiomyopathy patient samples (HF LVAD) were obtained from patients suffering from lamin A/C mutations, causing dilated cardiomyopathy and heart failure (HF LVAD 1M). A subset of these carried a second mutation in titin (HF LVAD 2M), leading to a more severe dilated cardiomyopathy. All samples were obtained after informed consent according to the study protocols approved by the hospital's ethics committee, as described elsewhere (Roncarati et al., 2013). Aortic stenosis ventricular samples were also obtained after informed consent according to the study protocols approved by the hospital's ethics committee.

Quantitative RT-PCR analysis: Left ventricles were snap frozen in liquid nitrogen after collection and stored at −80° C. Tissues were homogenized in 1 ml of PureZol RNA isolation reagent (Biorad) with GentleMACS and GentleMACS M Tubes (Miltenyi Biotec). After isolation of the aqueous phase with chloroform, RNA was extracted using RNeasy Mini Kit (Qiagen). The same amount of RNA was retrotranscribed with the High Capacity cDNA Reverse Transcription kit (Applied Biosystems). Real-time qPCR reactions were performed using TaqMan Probes and TaqMan Universal Master Mix on a REALTIME AB 7900HT cycler (all Applied Biosystems). The following TaqMan gene expression assays were used: Rn18S (Mm03928990_g1) as internal control, Cd3e (Mm005996484_g1), Foxp3 (Mm00475162_g1), Itgam (Mm00434455_m1), Tnfα (Mm00443260_g1), Il4 (Mm00445259_m1), Il-17 (Mm00439618_m1), Ifng (Mm01168134_m1), Tgfb1 (Mm01227699_m1), Il-10 (Mm00439614_m1), Il-6 (Mm00446190_m1), IL-1b (Mm00434228_m1), Ccl2 (Mm00441242_m1), Ccl4 (Mm00443111_m1), Ccl5 (Mm01302427_m1), Cxcl10 (Mm00445235_m1), Cxcl11 (Mm00444662_m1). Expression of genes encoding for Brain Natriuretic Peptide (Nppb), Atrial Natriuretic Factor (Nppa), and Myosin heavy chain β (Myh7) expression was tested with primers (IDT) using Sybr Select Master Mix (Applied Biosystems) on a ViiA7 (Applied Biosystems) instrument. The sequences are listed in table 3.

Transgenic Akt (Akt Tg) mice: Male Akt Tg mice, which constitutively overexpress the active E40K Akt mutant (Akt-E40K), as previously described (Condorelli et al., 2002) were used at 8 weeks of age.

Exercise-trained mice: BKS.Cg-m +/+ Lepdb/+db mice are heterozygous for the leptin receptor mutation but display a wild-type metabolic phenotype when fed on a normal diet. We utilized 8-week-old male mice that were arbitrarily assigned to one of two groups: sedentary and exercise trained 80 minutes/day, 5 days/wk, for 8 weeks, as previously described (Stolen et al., 2009). Due to the difference in genetic background (BKS), all analyses of these mice were performed comparing them to their matching controls, so as to avoid genetic background-specific effects.

Immunohistochemical analysis: mouse heart samples were fixed in 4% formalin at 4° C., paraffin-embedded and sectioned at 4 μm. The slides were stained with Azan's trichrome for collagen (BioOptica). Slide images were digitalized and five fields for mouse sections and ten fields for human biopsies analyzed to quantify fibrosis, with an image analysis program (ImageJ). Cardiac fibrosis was assessed by measuring the Azan's trichrome-stained area as a percentage of total myocardial area. For immunohistochemistry analysis sample sections on slides were deparaffinized and hydrated through a descending scale of alcohols. Antigen retrieval was performed using DIVA (Biocare Medical) for mouse samples and W-Cap (Biocare Medical) for human samples. Sections were cooled and then washed with PBS (Lonza) containing 0.05% Tween 20 (Sigma). Endogenous peroxidase was blocked by incubation with Peroxidase I (Biocare Medical) for 20 min at room temperature (RT) and nonspecific sites were blocked with Rodent Block and Background Sniper (Biocare Medical) for mouse and human samples respectively 20 min at RT. The sections were then incubated for 1 h at RT with rat anti-human CD3 (Serotec) diluted 1:1000 or AIF-1 (Wako) diluted 1:250 or polyclonal rabbit anti-human CD3 (Dako) diluted 1:50, washed, and incubated for 30 min at RT with rat-on-mouse HRP polymer (Biocare Medical) or with Mach1 HRP polymer (Biocare Medical) or with Envision+System anti-rabbit HRP (Dako). Finally, sections were incubated with DAB (Biocare Medical), counterstained with hematoxylin, dehydrated through an ascending scale of alcohols and xylene, and mounted with coverslips using Eukitt (Fluka). All samples were observed and photographed with a microscope Olympus BX53 with a digital camera.

TUNEL assay on mouse heart samples: Sample sections on slides were deparaffinized and hydrated through a descending scale of alcohols and TUNEL assay was performed (Click-it plus TUNEL assay C10617,Life technology).

In vitro stimulation of splenocytes with Abatacept: Total splenocytes were purified from spleens of 8-week-old male C57BL/6J mice. T cells were depleted using magnetic beads on an AutoMACS (Miltenyi Biotec). Total splenocytes or T cell-depleted splenocytes were stimulated with 2 μg/ml of anti-CD3 and cultured with 20 μg/ml abatacept or IgG istotype cnotrol. After 72 hours of culture, Brefeldin A (eBioscience) was added during the last 4 hours of culture and splenocytes were prepared for FACS analysis.

Flow cytometry: Single cell suspensions from spleens and lymph nodes were obtained via passing through 70 μm cell strainers in cold PBS−/−. Hearts were collected and digested with Liberase TM (Roche). Erythrocytes were removed with lysis buffer (BD Biosciences) from spleen and heart cell suspensions. Cells were stained with Live/dead Aqua Fluorescent Reactive Dye (Life Techonologies), anti-mouse CD3ε PerCP (145-2C11, BioLegend), anti-mouse CD19 eFluor450 (eBio 1D3, eBioscience), anti-mouse CD11b Pacific Blue (M1/70, Biolegend), CD11 c APC (Bu15, eBioscience), F4/80 Alexa488 (CI:A3-1, Serotec) in FIG. 11a, F4/80 (BM8, eBioscience) in FIG. 6d,e and 15, IL-10 PE (JES5-16E3, eBioscience), FoxP3 Alexa488 (FJK-165, eBioscience), Ly6C (HK1.4, eBioscience) or anti-CD86 Pacific Blue (GL-1, Biolegend), anti-CD80 FITC (16-10A1, BD Pharmigen) or anti-CD25 PE (PC61.5, eBioscience). An eBioscience intracellular staining kit was used were applicable. Samples were acquired on a FACS Canto II (BD) and analyzed with FlowJo10.

Statistics: Statistical analysis was performed in GraphPad Prism. All data sets were tested for normal distribution with normality tests before proceeding with parametric or nonparametric analysis. Grubb's test was performed in order to exclude spurious outliers.

Statistical significance was tested using unpaired t-test, one-way ANOVA with Tukey post-test and two-way ANOVA with Bonferroni post-test for data sets with normal distributions. Statistical significance was tested with Mann-Whitney test and one-way ANOVA with Dunn's post-test for data sets without a normal distribution. Fisher's exact tests were used in the analysis of collagen deposition, testing for the presence or absence of collagen stain. The standard deviation plot in FIG. 2 and FIG. 7A,B was calculated using a custom script in R.

Results

Example 1

Analysis of Soluble and Cellular Immune Mediators is Consistent with an M1-Type Immune Response that Switches to a Th2-Type Response with the Progression to Heart Failure We subjected mice to transverse aortic constriction (TAC), the standard model for pathological cardiac hypertrophy, and assessed the presence of soluble and cellular immune mediators within the myocardium via qPCR at 1 and 4 weeks after TAC surgery (FIG. 1). Cardiac functionality was monitored via regular transthoracic echocardiography (Table 1). At 1 week post-TAC, we found a significant upregulation of Tnfa and Il6, as previously described (Souders et al., 2012) (Kuang et al., 2013). Cells of the immune system are recruited to and/or retained at their sites of action via chemokines. We found a significant early expression of Ccl2 and Cxcl11 (Xia et al., 2009) as well as Ccl4, Ccl5 and Cxcl10 (FIG. 1), the majority of which are markers of a type 1 (M1/Th1)-polarized inflammatory response (Mantovani et al., 2004). Itgam (CD11b), a hallmark of the presence of innate immune cells, such as macrophages or monocytes, was also upregulated 1 week post-TAC, suggesting that type 1-polarized innate immune cells are recruited to the stressed myocardium early on.

We observed significant upregulation of the T cell-specific marker Cd3e at 4 weeks post-operation, suggesting that T cells expand or are recruited to the stressed left ventricle at this later time point. Concurrent upregulation of Il4, a hallmark of type 2 (M2/Th2)-polarized responses, suggests a gradual shift from an M1 to an M2/Th2 response as the myocardium progresses toward HF. Indeed, Th2-polarized T cells have been reported to promote fibrosis in other pathological conditions (Wynn, 2004). Transcripts of cytokines that characterize Th1 and Th17 responses, such as Ifng and Il17, or of the anti-inflammatory cytokine Il10 were not significantly altered at any time point.

Example 2

The Onset of Inflammation is Correlated with T Cell Infiltration

As we had generated data on Cd3e expression (indicative of T cell presence) and il6 expression (indicative of inflammation), we asked whether the onset of inflammation correlated with T cell infiltration and/or proliferation. Assuming a linear regression model, we first examined the correlation between Cd3e and il6 in samples derived from TAC-operated mice, 4 weeks post-operation. The results (FIG. 13, circles and corresponding regression line) show a significant positive slope, suggesting that such a correlation exists. A likely interpretation would be that inflammation drives the infiltration and/or proliferation of T cells into the myocardium. Repeating the analysis for sham-operated animals (FIG. 13, squares and corresponding regression line) also yielded a significant positive slope, however with lower mean il6 and cd3e values. This suggests that, even in the absence of the aortic constriction, the limited (but nonetheless present) inflammation generated by the sham operation (which does involve surgery, albeit without permanent constriction) may be leading to a limited infiltration/proliferation of T cells, even if this is significantly lower than in TAC (as shown in FIG. 1).

Example 3

Figure 8A:
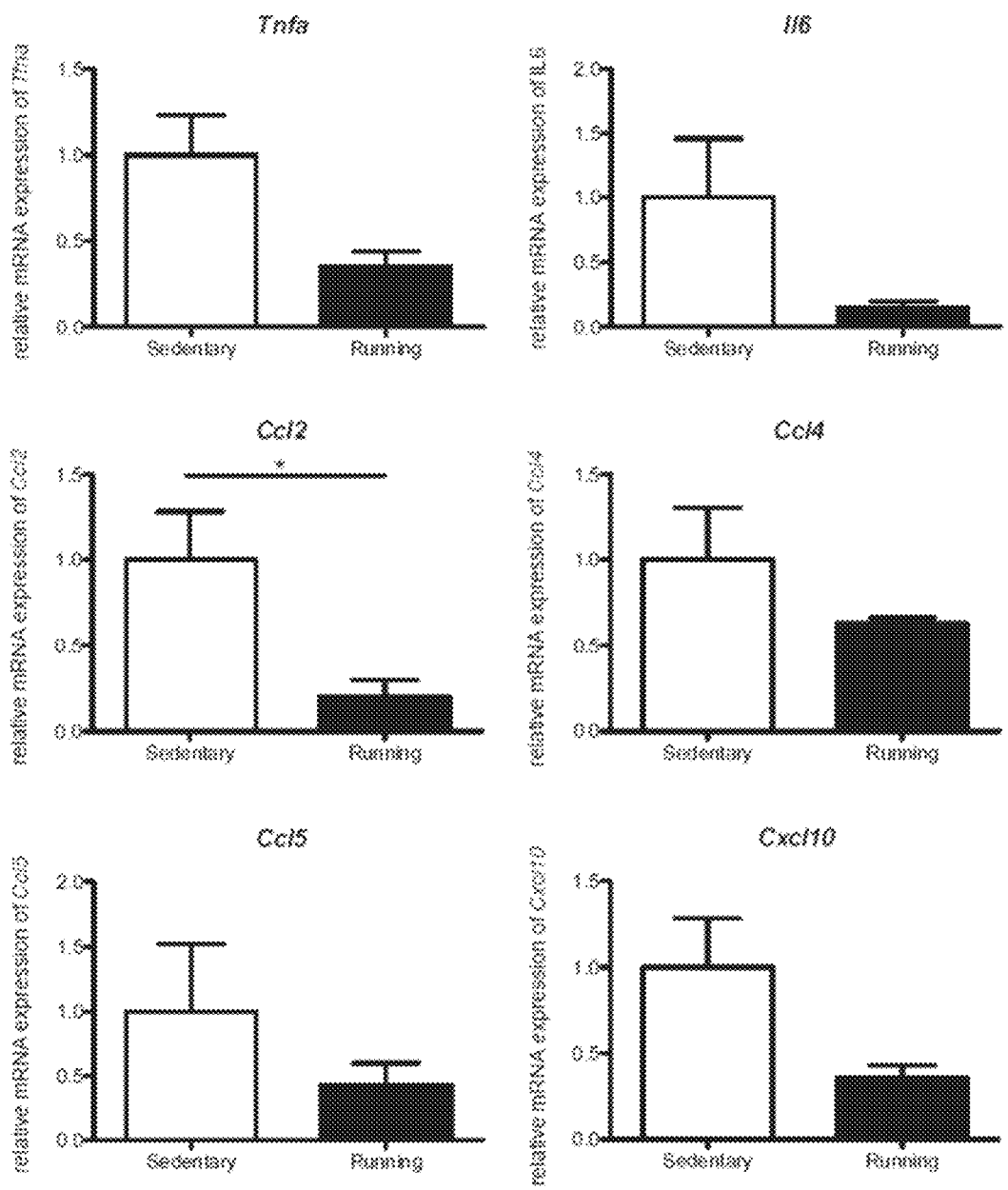

The Immune Response Mediator Profile Distinguishes Pathological From Physiological Cardiac Hypertrophy The above show that pathological cardiac hypertrophy, which leads to fibrosis and HF, is associated with inflammation. Yet non-pathological forms of cardiac hypertrophy also exist, which do not lead to fibrosis or cardiac dysfunction. The most physiologically relevant model for these is exercise training. Mice subjected to a running program show "physiological" hypertrophy in which the increase in cardiomyocyte size is accompanied by an increased functionality of the cells and absence of fibrosis (Perrino et al., 2006) (Kemi et al., 2008). We thus asked whether the immune mediators that we identified in the TAC model of HF were also present in exercise-trained mice. We found no significant upregulation of immune response mediator transcripts in these mice (FIG. 8A). This finding strongly suggests that, unlike pathological hypertrophy, physiological hypertrophy features a complete absence not only of fibrosis, but also of an innate and adaptive immune response.

Figure 8B:
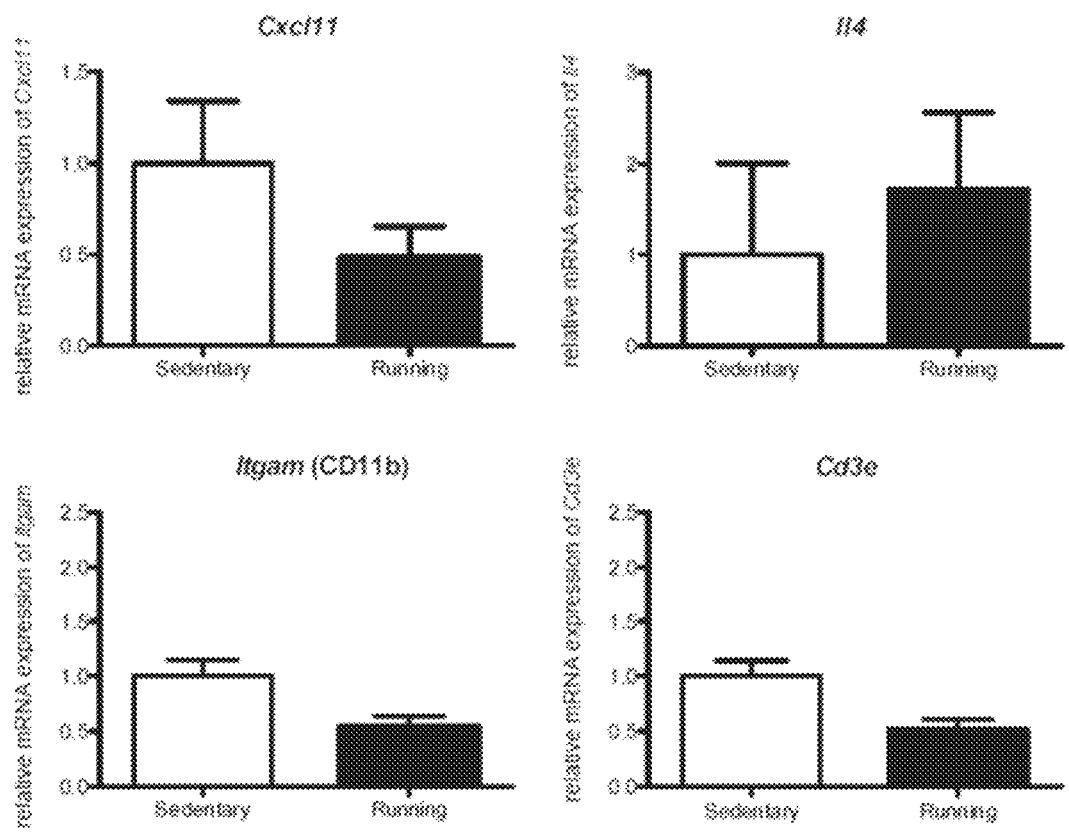
Figure 8C:
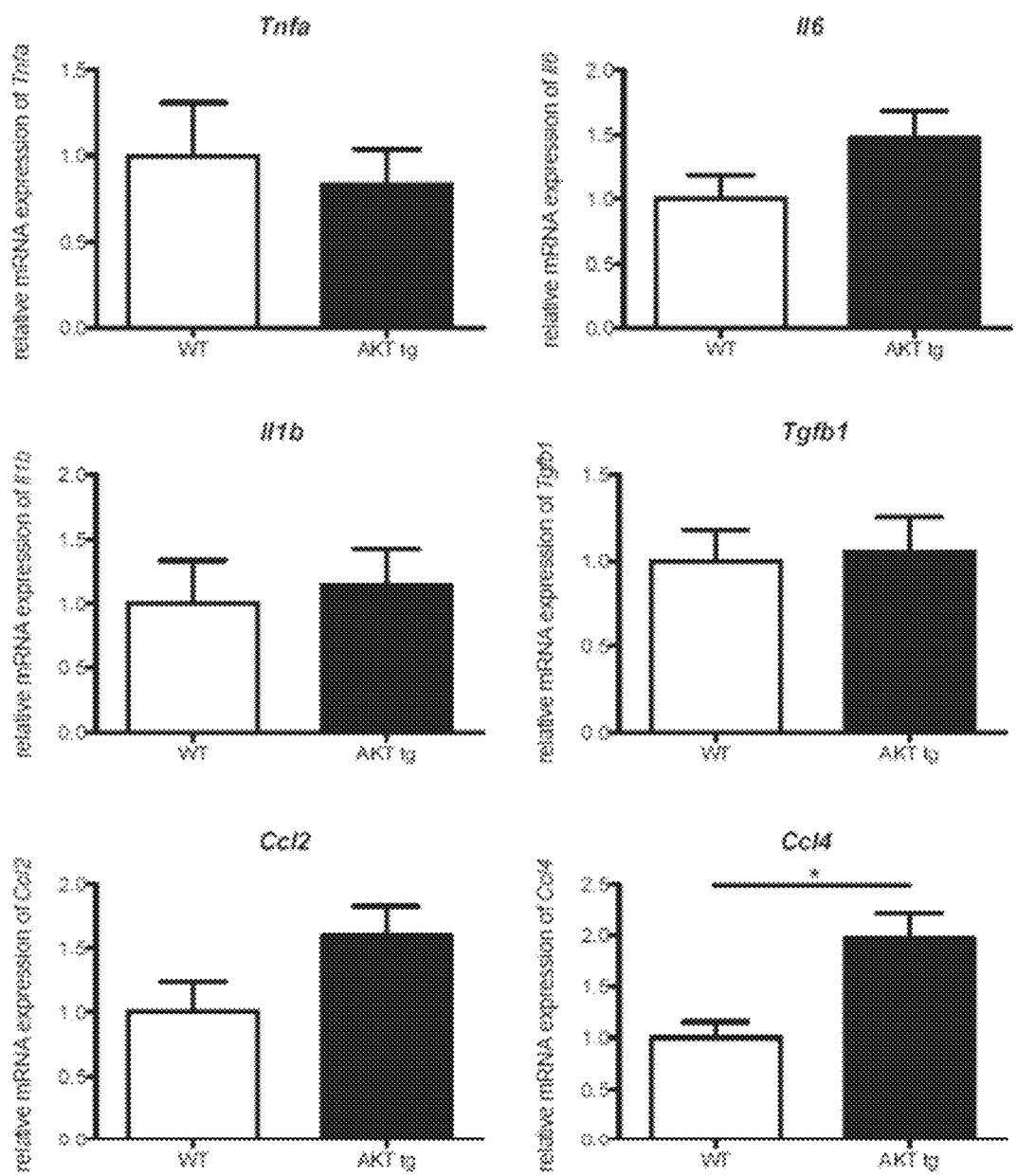
Figure 8D:
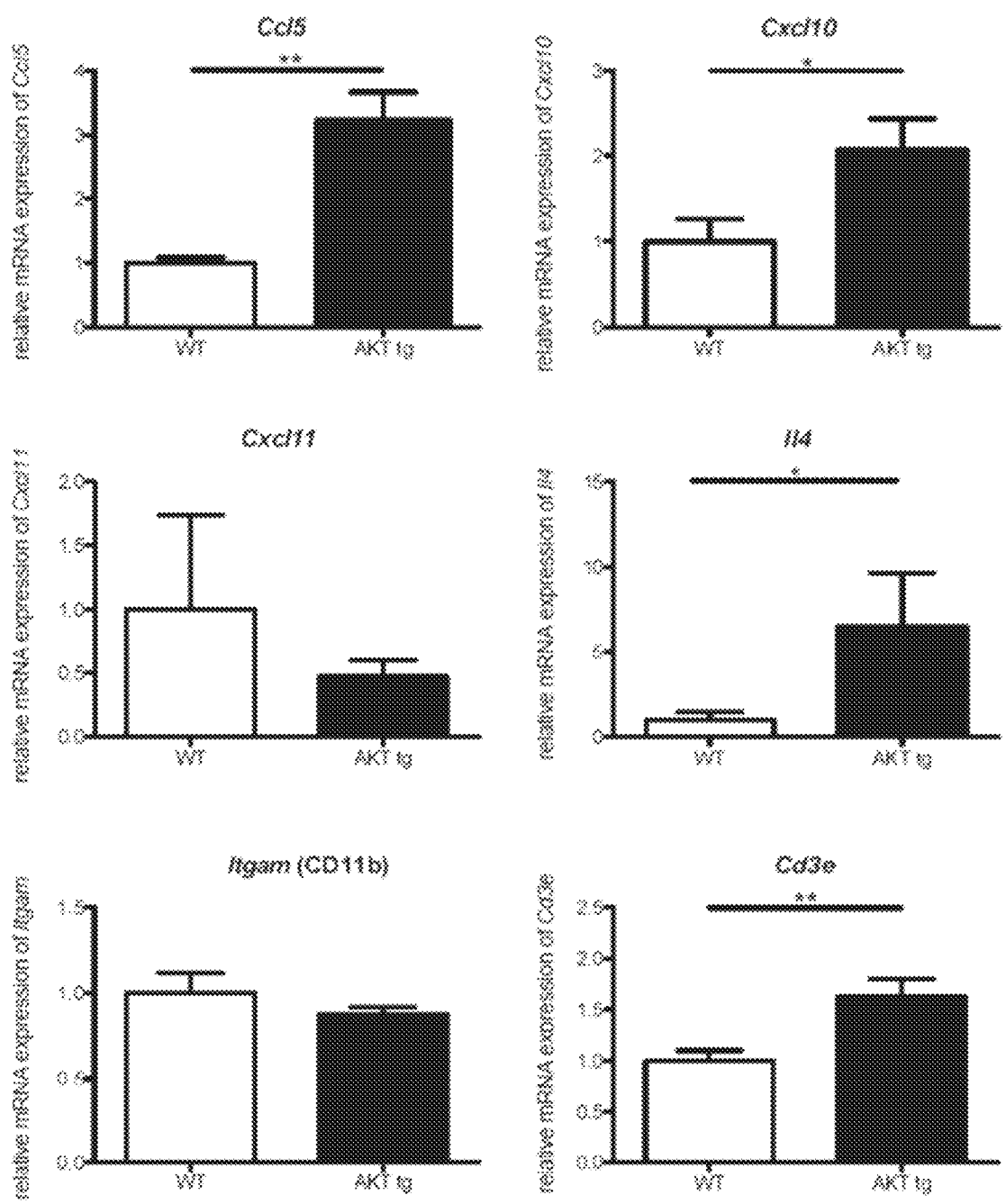

To better visualize these differences, we plotted an index of heart dysfunction (loss in percent fractional shortening, i.e., the decrease in pumping volume of the ventricle) against an index of inflammation (i.e., the ratio of transcript expression of the pro-inflammatory cytokine IL-6 to the anti-inflammatory cytokine IL-10) (FIG. 2). The resulting dot plot, where each dot represents one animal and the ellipses represent one standard deviation for both variables, illustrates clearly the link between inflammation and impaired heart function. Whilst both exercise-trained mice (FIG. 2: Exercised (running) mice) and TAC-operated mice (FIG. 2: TAC model of HF) are characterized by cardiac hypertrophy, the pathologically-hypertrophic TAC-operated mice had increased indices of inflammation (values shifted towards the right compared to healthy controls) and increased heart dysfunction (values shifted towards the top compared to healthy controls). On the other hand, exercised mice had an inflammation index similar to that of healthy controls but an improved heart function (downward shift on the y axis). A more "artificial", non-pathological hypertrophy model, induced by cardiac-specific overexpression of the constitutively active E40K mutant of the serine-threonine kinase Akt in the heart (Condorelli et al., 2002), displayed an incomplete array of pro-inflammatory mediators present in the left ventricle of 8-week old Akt transgenic mice (FIG. 8B). Hence these mice occupied an intermediate state in the heart dysfunction versus inflammation dot plot, i.e., one in-between the two extremes of TAC- and running-induced hypertrophies. Thus, our results support a positive association between inflammation and the pathological nature of cardiac hypertrophy.

Example 4

T Cells are Present in the Stressed Myocardium in Mice and Humans

The above findings encourage the notion that inhibition of inflammation could be a promising strategy against HF. This approach has been attempted before, but the targets identified resulted to be inadequate for this end (Yndestad et al., 2006) (Hofmann and Frantz, 2013). T cells are required for the maintenance of long-term immune responses (Loke et al., 2007) and thus could represent a better therapeutic target. Driven by the finding of T cell-specific Cd3e mRNA upregulation in TAC mice at 4 weeks post-TAC, we further investigated the presence of T cells in pathological hypertrophy. By examining the left ventricles of mice by immunohistochemistry (IHC) with anti-CD3e (FIG. 3A), we found that T cells were visibly and significantly more abundant in TAC versus sham mice at 4 weeks (FIG. 3B), confirming the mRNA data. During the time course of the pathology, T cells presumably react in an antigen-specific manner, involving few specific clones that subsequently expand in number. Thus we hypothesized that T cells should also be detectable at an early stage of disease development. We performed the IHC analysis on mice at 1 week post-TAC, and indeed we were able to detect T cells (FIG. 3C). We also performed lymphocyte-enriching gradient purification on cardiac suspensions derived from hearts of mice at 1 week post-TAC, and observed that the resultant cell populations did include CD3e-expressing cells when examined by flow cytometry (FIG. 3D). Therefore, T cells were present in the hypertrophic myocardium even at an early stage of the pathology. Previous studies in the TAC model have identified that cardiac dysfunction can be detected as early as 2 days post-TAC. T cell activation is often initiated at the lymph nodes that drain the site of inflammation. We thus examined via flow cytometry whether, at 2 days post-TAC, T cells were activated in the heart-draining (mediastinal) lymph nodes. We also examined non-draining (inguinal) lymph nodes as well as spleens of the same animals. We found that, at day 2, a significant upregulation of the activation marker CD25 could be seen among CD3+ T cells in the heart-draining lymph nodes, though not in the more distal, non-draining lymphoid compartments (FIG. 3e). The early presence of T cells, and identification of T cell presence in the ailing myocardium, thus creates an opportunity for attempting a manipulation of their function for therapeutic purposes.

In order to confirm the clinical relevance of our findings in the human setting, we examined T cell abundance in cardiac tissue derived from heart failure patients suffering from primary cardiomyopathy, which shares pathological traits with our experimental mouse model. We examined tissue from patients carrying lamin A/C mutations, which lead to dilated cardiomyopathy and heart failure. A subset of these carried a second mutation in titin, leading to a more severe dilated cardiomyopathy. We chose these patients as their cardiomyopathy is caused by a non-immunological cause, unlike inflammatory, autoimmune or viral cardiomyopathies. Thus detection of T cells in the left ventricle of these patients would suggest that presence of T cells is correlated not only with cardiomyopathies initiated by excessive immune responses, but also with cardiomyopathies triggered by non-immune causes. The cardiac samples were obtained during surgery for the placement of a Left Ventricular Assist Device (LVAD), attesting to the advanced stage of their cardiac dysfunction. Azan's trichrome analysis for collagen (FIG. 3G) confirmed presence of fibrosis in these specimens (FIG. 3F). Analysis of T cell abundance via CD3e IHC (FIG. 3I) in the same samples revealed the presence of infiltrating T cells, like in the hearts of mice at 4 weeks post-TAC, (FIG. 3B). In addition to the above LVAD HF patient samples, we also examined samples from patients suffering from aortic stenosis. Aortic stenosis leads to heart failure 24 and represents the clinical condition that is mechanistically the closest the TAC mouse model. We found that left ventricles from patients with this form of cardiomyopathy also demonstrated a similarly increased fibrosis (FIG. 3*j*) and T cell presence (FIG. 3*k*). Taken together, these results lend further support to a link between T cell presence, cardiac fibrosis and pathological hypertrophy.

Example 5

T Cell Costimulation Blockade Reduces the Severity and Delays the Progression of HF in Mice We hypothesized that specific inhibition of T cell function would have a beneficial effect on HF development. CTLA4 is one of the inhibitory molecules through which naturally occurring regulatory T cells suppress T cell activation under physiological conditions (Wing and Sakaguchi, 2010). It blocks the CD80/CD86 costimulation signals that T cells must receive from antigen presenting cells (dendritic cells, B cells or macrophages) in order to become fully activated (Moreland et al., 2006). CTLA4-Ig fusion protein (abatacept, an FDA-approved drug for the treatment of rheumatoid arthritis, an autoimmune disease) is a stable, soluble form of CTLA4. We therefore tested whether the administration of abatacept produced a beneficial effect in the TAC model of HF. We treated mice that had been TAC- or sham-operated with three intraperitoneal injections per week of 200 micrograms of abatacept, for 4 weeks, starting 2 days after the operation. As controls, TAC- and sham-operated mice received PBS, at the same timepoints. Cardiac function was monitored by transthoracic echocardiography (see Table 2). Day 2 post-operation was chosen as the first time-point of treatment as significant cardiac dysfunction (increase in left ventricle thickness) can already be detected at 2 days post-TAC via clinically-relevant diagnostic techniques (echocardiography).

Figure 4A:
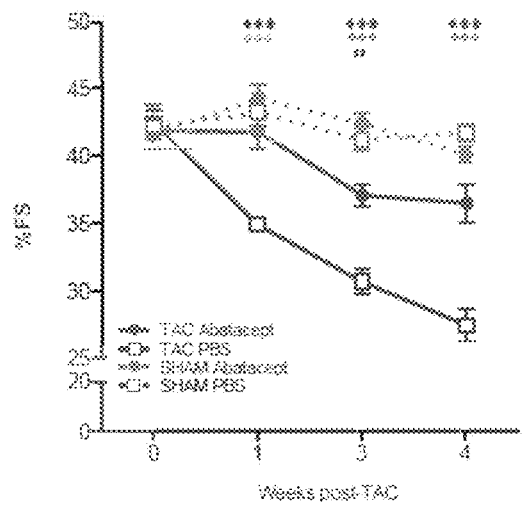
Figure 4B:
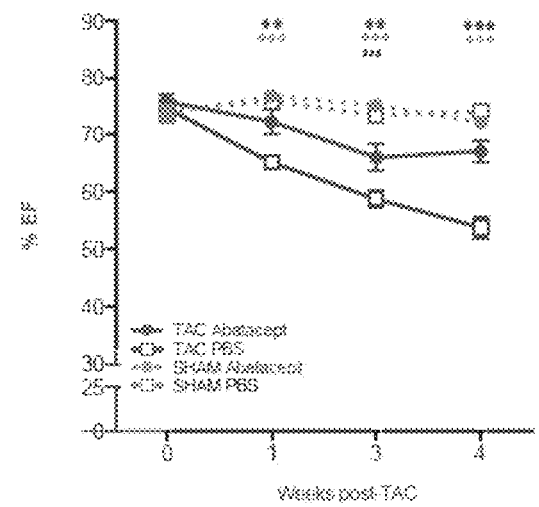
Figure 4C:
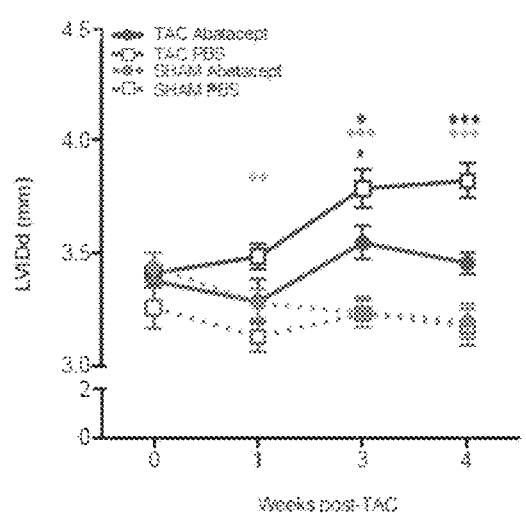
Figure 4D:
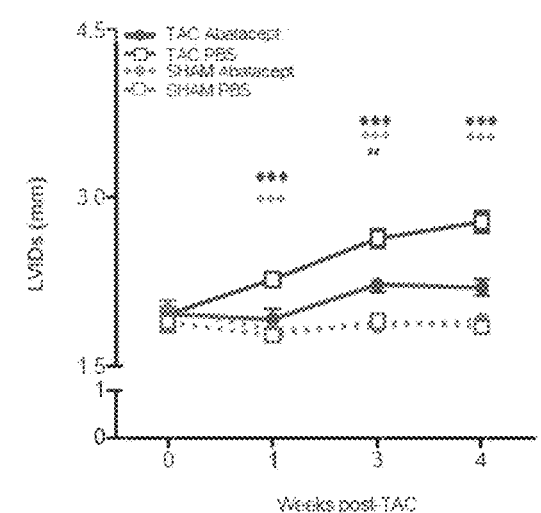
Figure 4E:
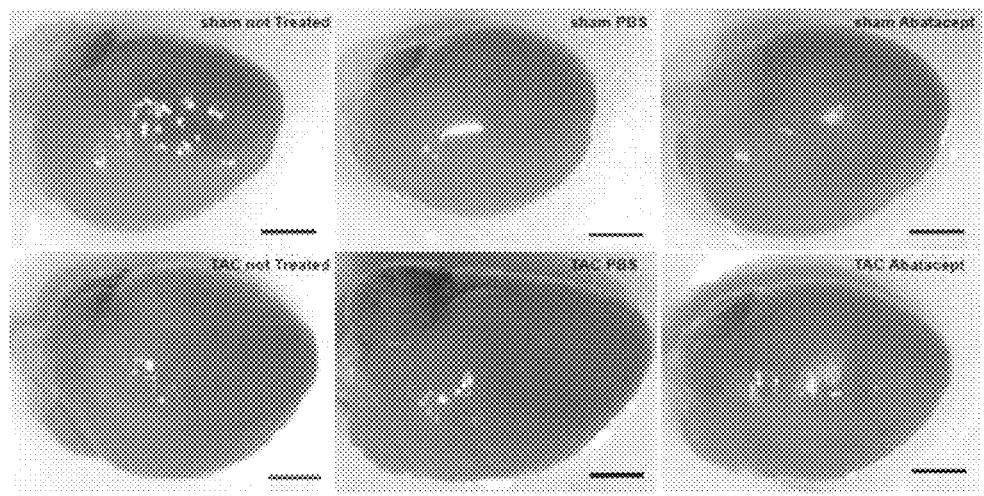
Figure 9A:
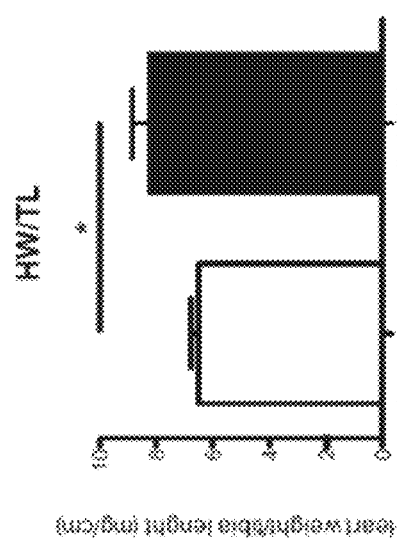
Figure 9B:
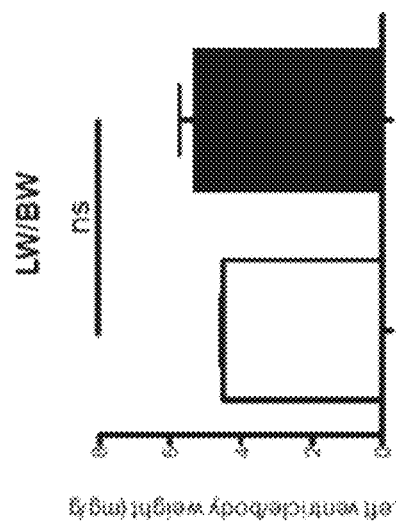
Figure 9C:
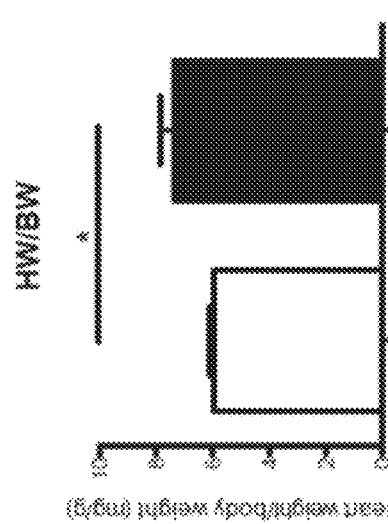
Figure 9D:
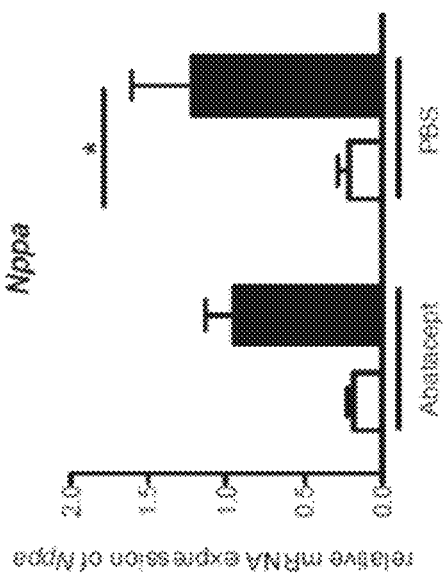
Figure 9E:
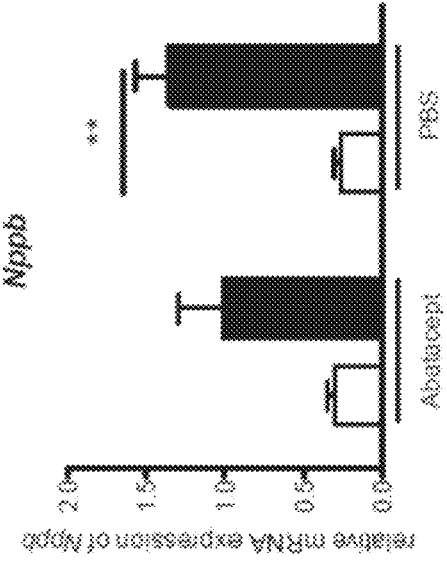
Figure 9F:
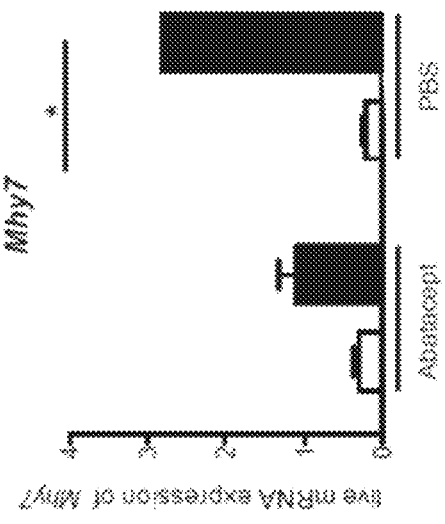

PBS-treated TAC-operated mice at 1 and 4 weeks post-operation displayed a significant reduction in cardiac function, expressed as percent fractional shortening (FS) or ejection fraction (EF) compared to sham controls, whilst abatacept-treated mice had no significant difference in FS or EF from sham controls (FIG. 4A-B). Difference in FS was evident from the first week post-TAC operation, up to the end of the experiment (FIG. 4A); also difference in EF increased in significance with time between the PBS- and abatacept-treated groups (FIG. 4B). Hence by administering abatacept starting from 2 days after TAC surgery, we were able to significantly reduce the extent and delay the progression of degradation of cardiac function. The beneficial effect of abatacept was also evident by analyzing other hemodynamic parameters, including the end-diastolic left ventricular internal diameter (LVIDd) (FIG. 4C), and the end systolic one (LVIDs) (FIG. 4D). Other measured parameters are reported in (Table 2). At 3 weeks post-operation, a transient yet significant difference between abatacept-treated and sham control animals could be seen. At the end of the fourth week, we assessed the morphometric indicators of cardiac hypertrophy: heart weight to body weight ratio (FIG. 9A), left ventricle to body weight ratio (FIG. 9B), heart weight to tibia length ratio (FIG. 9C). TAC-operated mice treated with abatacept displayed significantly lower hypertrophy than PBS-treated controls, according to most of these parameters. Analysis of myocardial "stress genes", a hallmark of cardiac hypertrophy and failure, in the left ventricles by qPCR also showed a significant up-regulation of β-Myosin heavy chain (Mhy7) (FIG. 9D), Brain Natriuretic Peptide (Nppb) (FIG. 9E) and Atrial Natriuretic Factor (Nppa) (FIG. 9F) mRNAs for the PBS- but not for the abatacept-treated groups. Thus, abatacept treatment significantly reduces the severity and delays the progression of the cardiac dysfunction caused by the ventricular pressure overload.

Figure 4F:
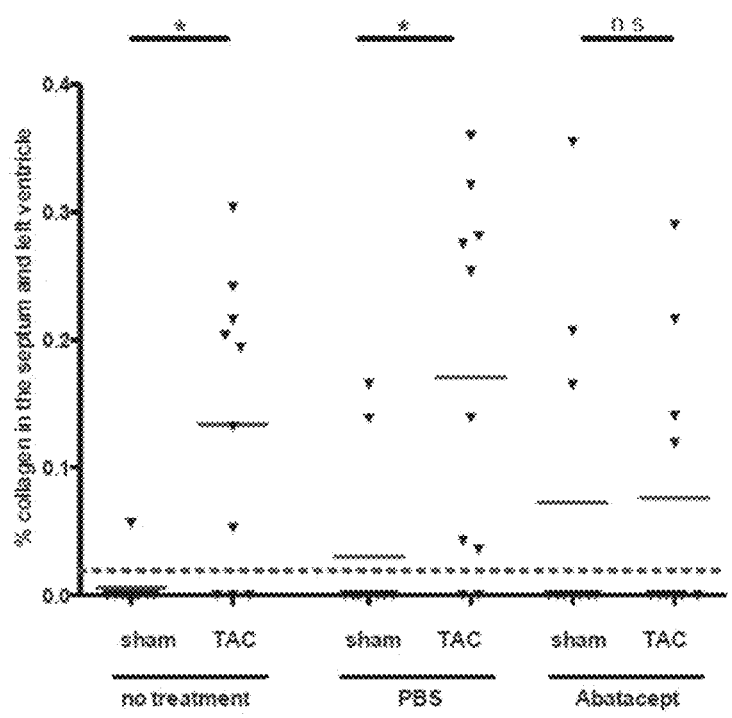
Figure 4H:
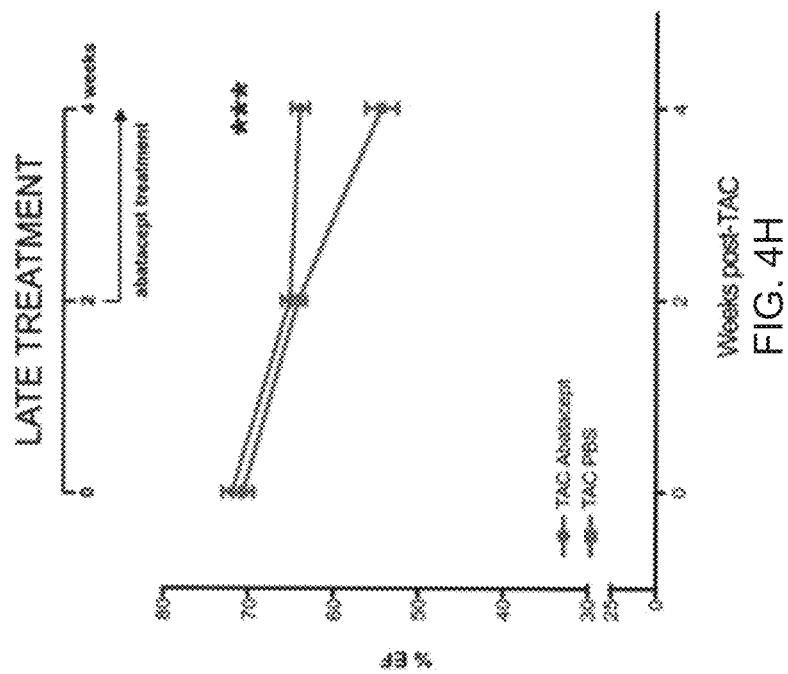
Figure 4G:
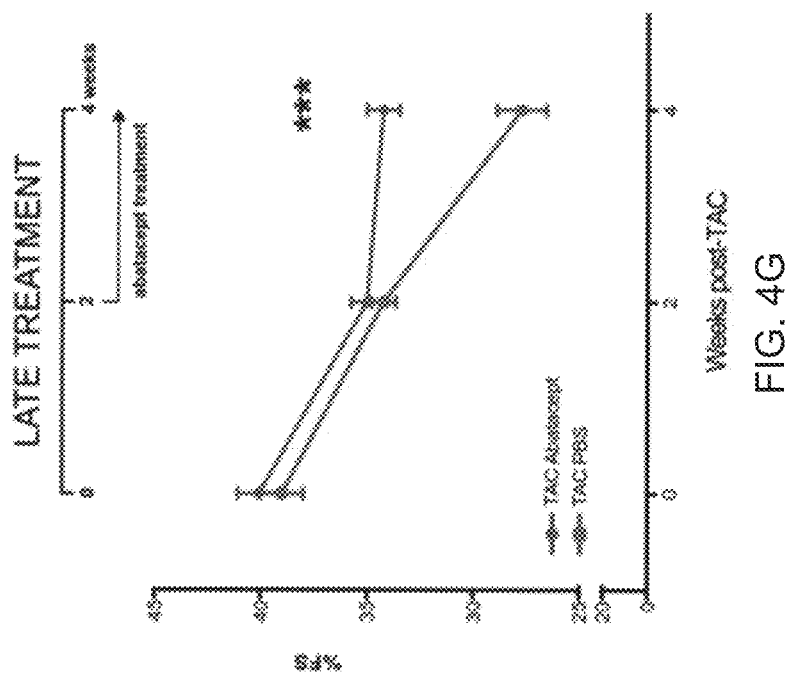

We also examined sections with Azan's trichrome staining in order to assess the levels of fibrosis (Condorelli et al., 1999). A comparison of collagen intensity in identical regions sampled for all treatment groups identified significant increases in fibrosis levels for all TAC-operated groups except for the mice treated with abatacept (FIG. 4F). These results suggest that the beneficial effect of abatacept is also reflected in protection from cardiac fibrosis, a biological response invariably linked to heart failure (Kong et al., 2014).

Importantly, abatacept is based on human CTLA-4 fused with human immunoglobulin and thus suitable for human use, but it has been extensively shown to function in mice, due to the high similarity of human and mouse CTLA-4 (Dhirapong et al., 2013). As human Ig administration could be immunogenic in mice( ), we included a further set of non-operated mice that received abatacept or an isotype control immunoglobulin (Ig), to assess any reactivity of the recipients to the human Ig used in the fusion protein. Neither abatacept alone nor human IgG control injections led to any significant change in heart function (FIG. 10), signifying that any alloreactivity to the immunoglobulin had limited effects.

Figure 10B:
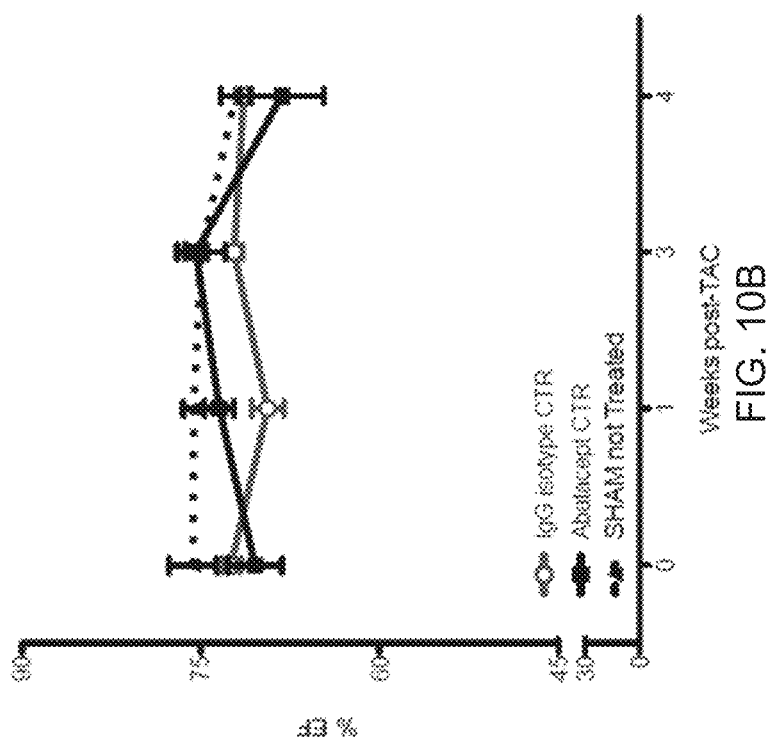
Figure 10A:
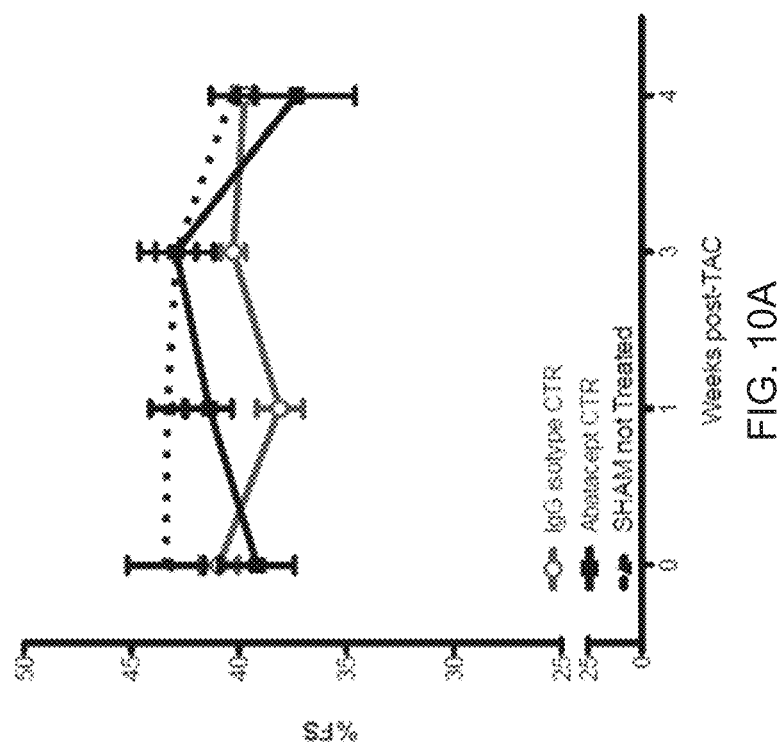
Figure 10D:
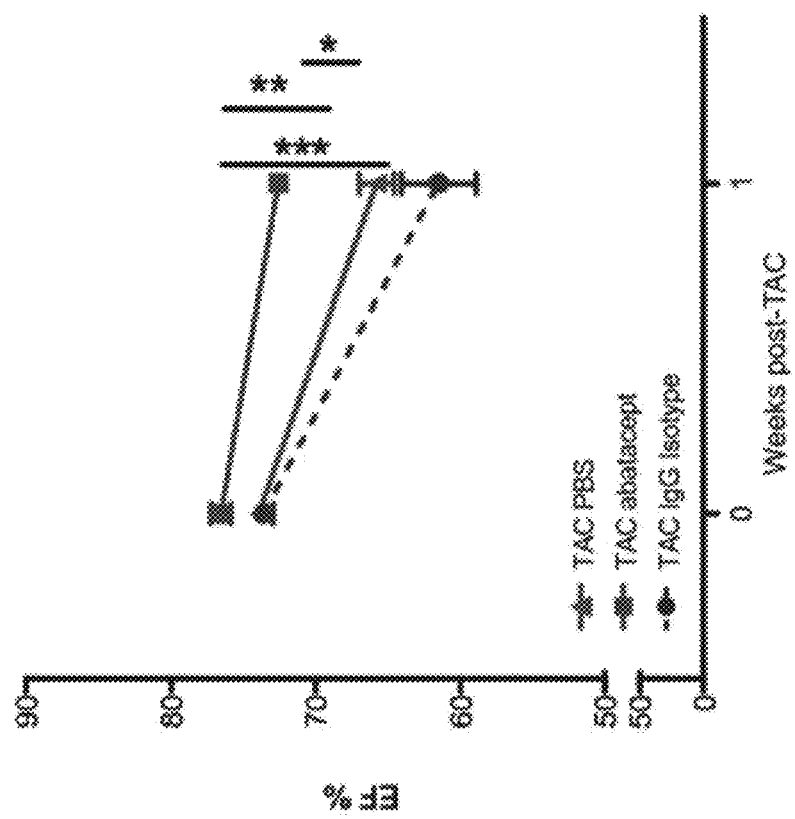
Figure 10C:
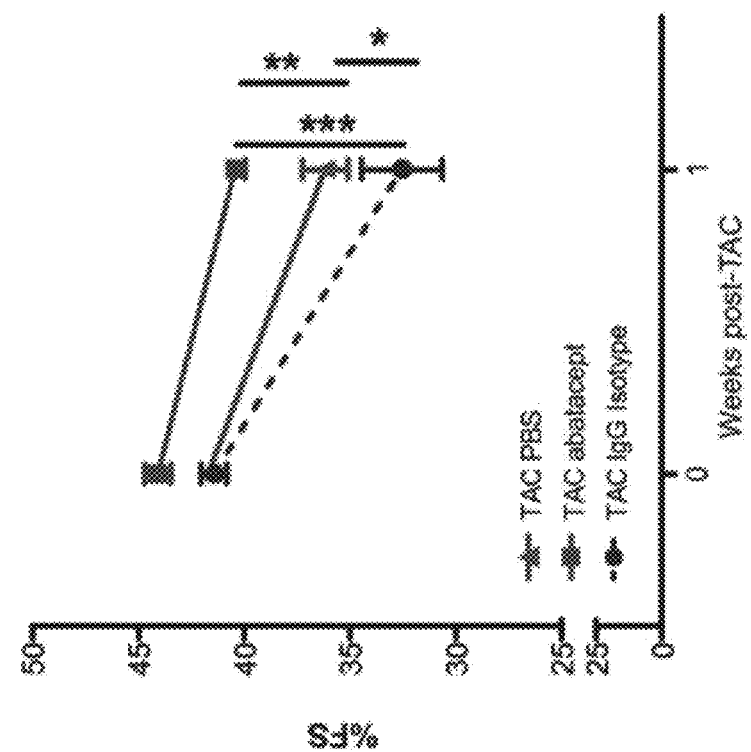
Figure 10F:
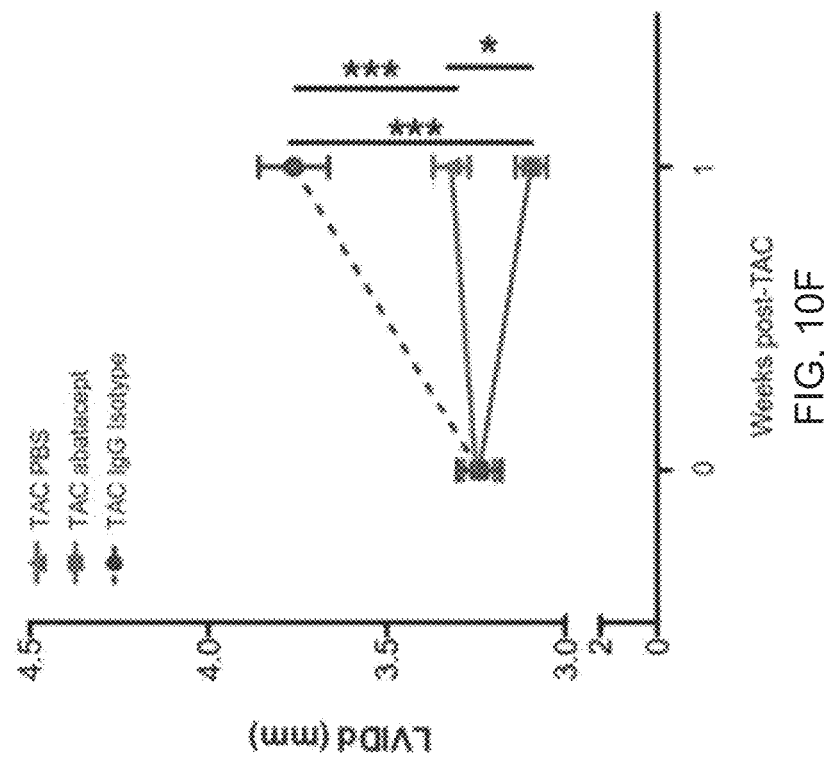
Figure 10E:
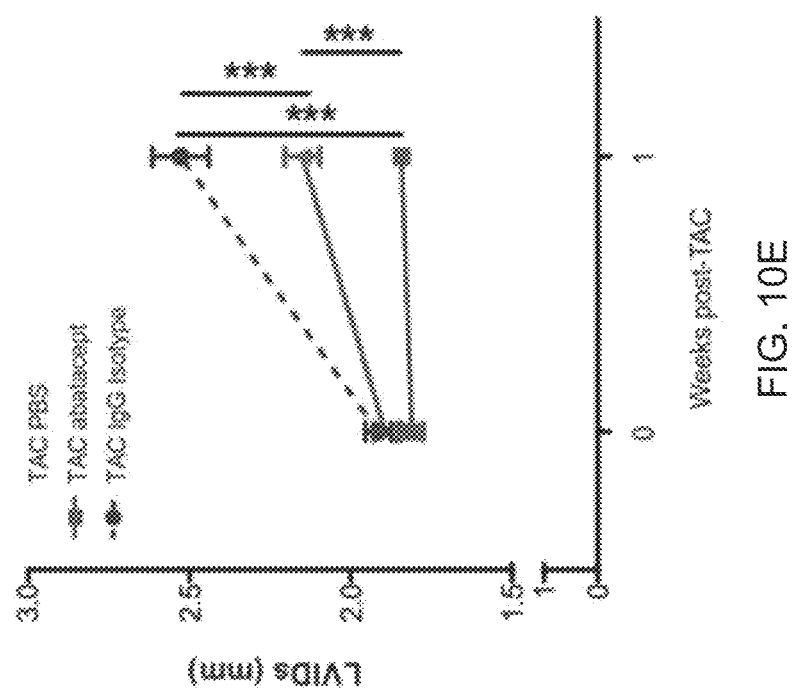
Figure 10H:
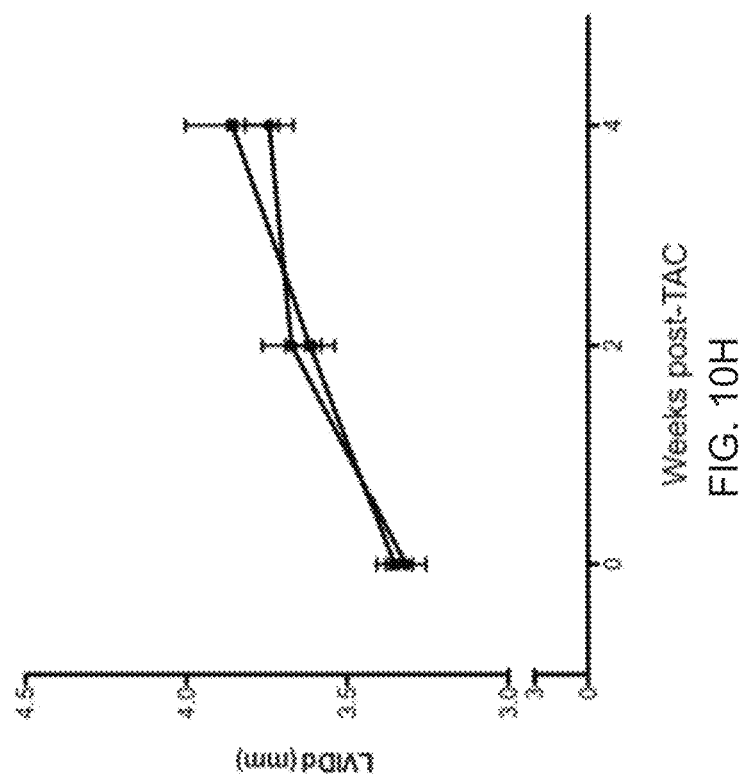

Nonetheless, the potential for alloreactivity of the IgG control, in the absence of the immunosuppressive CTLA-4 domain, could possibly worsen the TAC-induced inflammation. For this reason, we chose to use PBS administration rather than IgG administration as a control for our experiments, so as to avoid any deleterious effect on the controls creating the appearance of a stronger therapeutic effect in the abatacept-treated group. Indeed, when we assessed the in vivo effect of abatacept in TAC-operated mice, we found that its protective effect appeared to be even more significant when compared to isotype control-treated rather than PBS-treated TAC-operated mice (FIG. 10*c,d,e,f*). This confirmed the validity of our choice of controls.

Example 6

Inhibition of T-Cell Costimulation is Effective at an Advanced Stage Disease

Figure 10G:
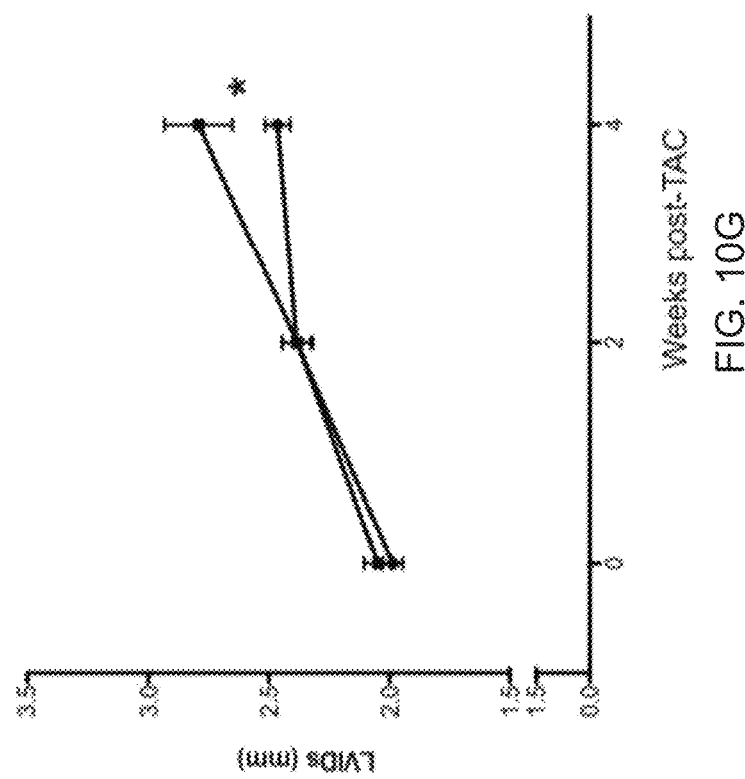

We next wondered whether abatacept treatment would be able to block the progression of cardiac dysfunction if administered only at a late timepoint, when the disease is more advanced. For this reason, we repeated the in vivo treatment with abatacept, albeit commencing the first treatment at 2 weeks post-TAC, instead of 2 days post-TAC. As can be seen (FIG. 4*g, h*) treatment at a late timepoint nonetheless was able to significantly block the further reduction of FS and EF in treated animals. A significant protective effect was also observed in LVIDs (FIG. 10g). These results demonstrate that even late treatment with the drug may have substantial beneficial effects in limiting the progression of HF.

Example 7

Abatacept Protects from Pathological Hypertrophy by Inhibiting T Cell Activation, as Well as by Affecting Macrophages Extensive studies have shown that CTLA4-Ig inhibits T cell function, by blocking the costimulatory receptors on antigen presenting cells, which are required for the full activation of pro-inflammatory T cells (Linsley et al., 1991) (Moreland et al., 2006).

Figures 5A, 5B:
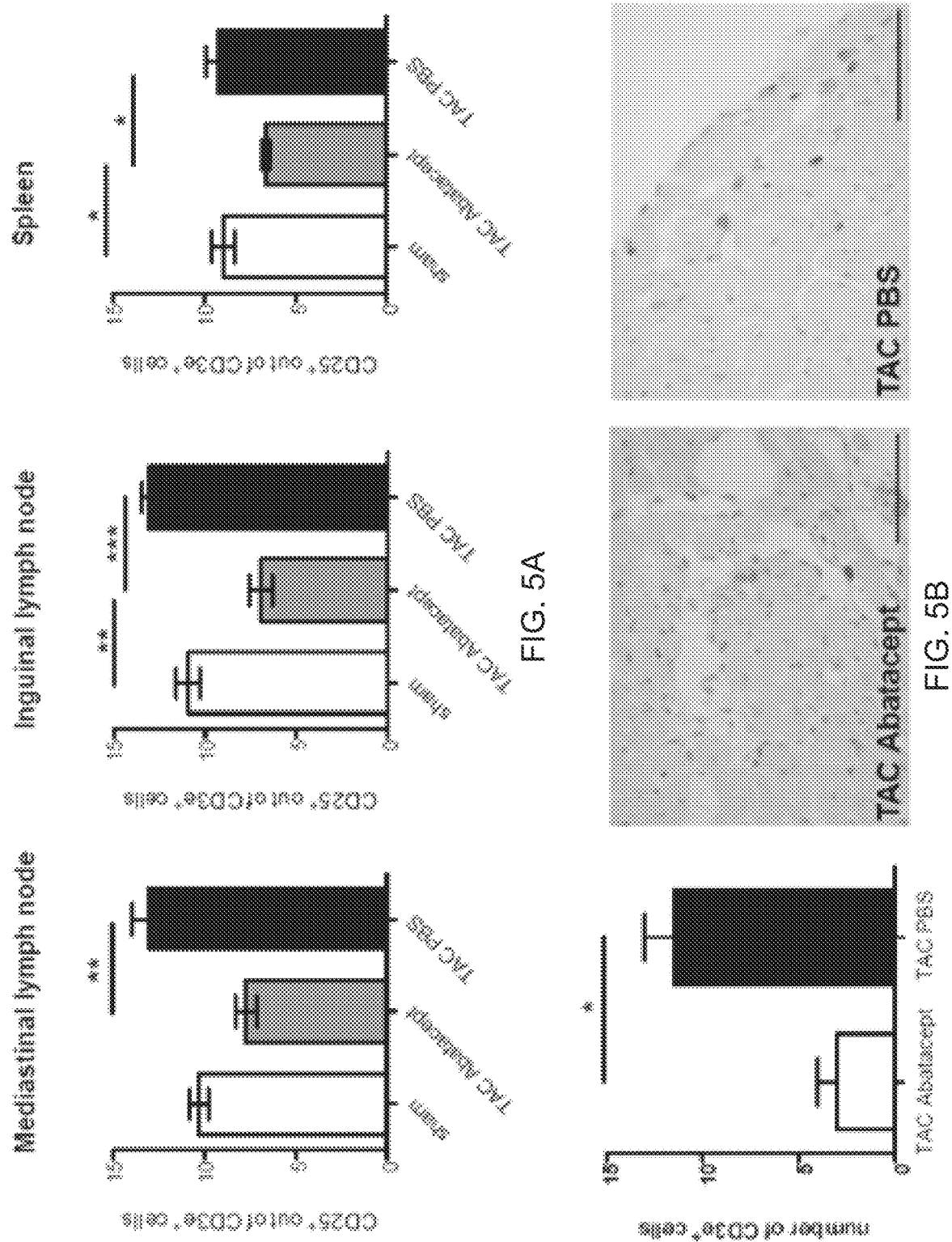

Indeed, the CTLA-4 molecule represents one of the main available mechanisms through which already initiated T cell responses can be physiologically downregulated (Bluestone, 1997) (Krummey and Ford, 2014). We therefore sought to dissect how abatacept was affecting T cell activation in pathological cardiac hypertrophy. For this, we examined via flow cytometry the expression of activation marker CD25 in T cells at an early timepoint (1 week post-TAC), which is likely to be the relevant time window for activation events. Abatacept significantly reduced the percentage of CD25+ cells among T cells, not only in the heart-draining (mediastinal) lymph nodes, but also in inguinal lymph nodes and spleen (FIG. 5A). This suggests that abatacept exerted a systemic dampening of T cell activation. CD25 expression on the T cells infiltrating the heart could not be reliably assessed due to the low number of T cells found in the heart at 1 week post-TAC, which renders flow cytometric analysis of subpopulations technically challenging.

Figure 5C:

Reduced T cell activation is likely to lead to reduced proliferation and lower T cell numbers at later timepoints. Indeed, at 4 weeks after surgery, the myocardium of abatacept-treated mice displayed significantly fewer infiltrating T cells than PBS-treated mice (FIG. 5B). Of note, the IgG isotype control for abatacept had no effect on in vitro T cell responses, unlike abatacept itself (FIG. 11A). We also wondered whether the abatacept-mediated suppression of T cells led to a downstream inhibitory effect on macrophage activation, which has recently been shown to contribute to cardiac pathology (Epelman et al., 2014). We assessed via immunohistochemistry the expression of AIF-1 (Iba-1), a marker of T cell-derived macrophage activation (Utans et al., 1995) (Tian et al., 2006), in the hearts of operated mice. In TAC-operated mice, Abatacept treatment led to a significant reduction in AIF-1 signal compared to PBS-treated controls (FIG. 5C). Sham-operated mice had negligible signals of AIF-1+ cells. At 4 weeks post-surgery, the difference in AIF-1$^+$ macrophages between the two groups was minimal (FIG. 14), most likely as the overall levels of AIF-1$^+$ macrophages, or indeed total CD11b$^+$ innate immune cells (FIG. 1) in TAC-operated mice is reduced at this late stage of the pathology.

We next examined the maturation state of macrophages[38] found in the left ventricles of abatacept or control-treated TAC mice at 1 week post-operation, by flow cytometric analysis. We considered the percentage of Ly6C$^+$F4-80$^+$ (immature macrophages) or Ly6C$^-$F4-80$^+$ (mature macrophages) out of CD11b$^+$CD45$^+$ live single cells (gating strategy shown in FIG. 15). We found that hearts of abatacept-treated animals had significantly higher percentage of immature macrophages (FIG. 5e) and significantly lower percentage of mature macrophages (FIG. 5f), compared to controls.

This finding suggests that the inhibition of T cells according to the invention may also have downstream effects on pathogenic macrophages in the myocardium, including, e.g., on the activation and maturation state of macrophages in the myocardium.

Example 8

The Protective Effect of Abatacept is Dependent on IL-10

Figure 5D:
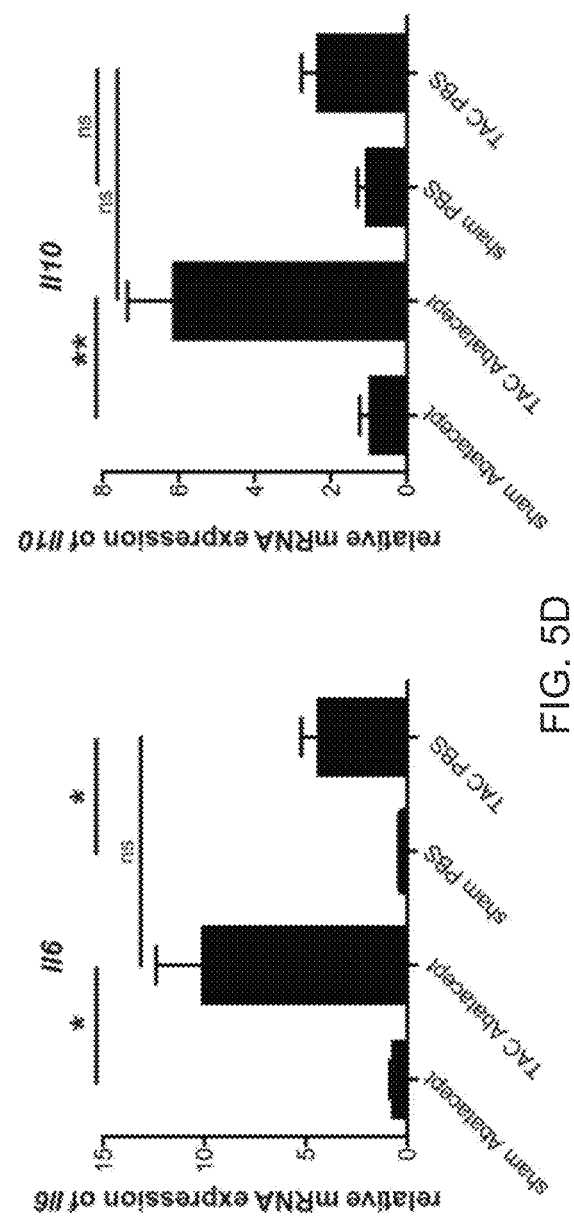
Figure 5F:
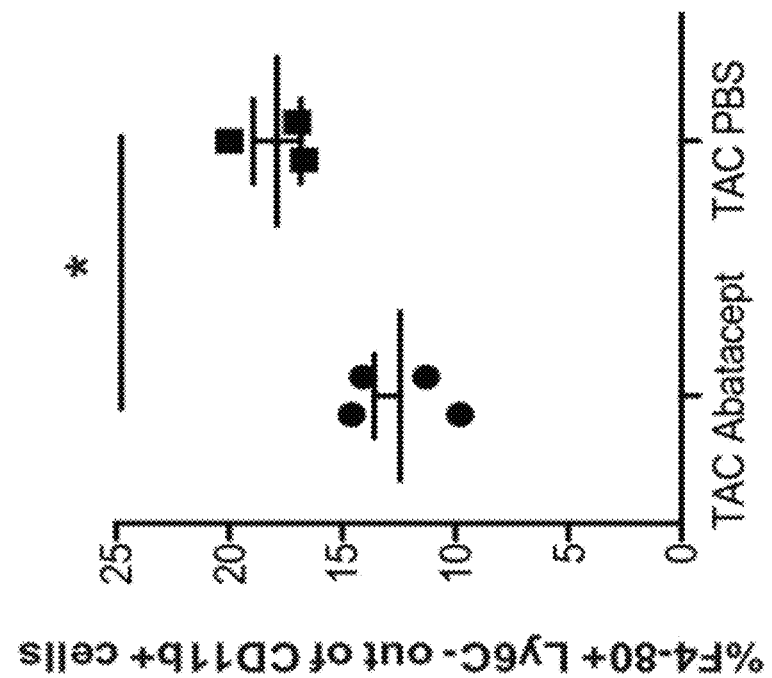
Figure 5E:
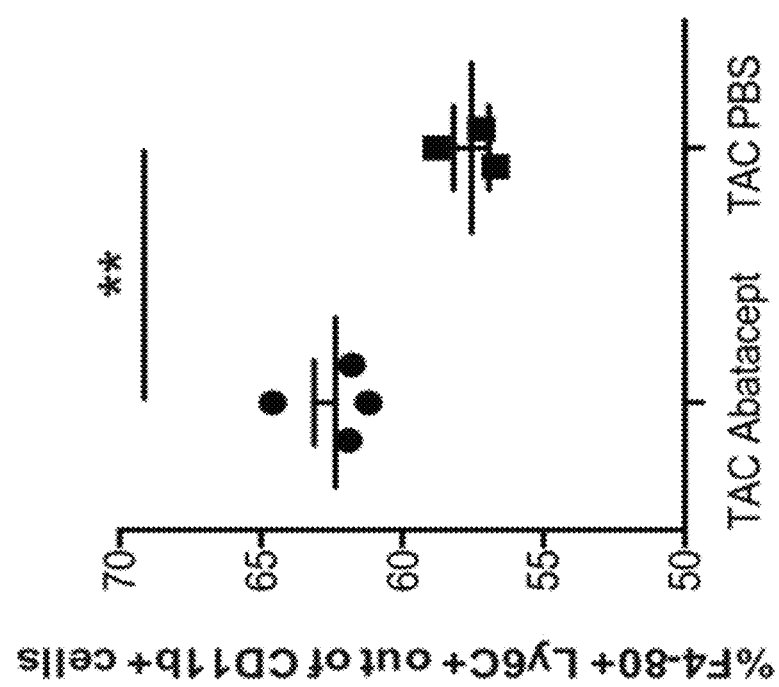

The effect of abatacept on T cell activation occurs via the removal of pro-inflammatory, costimulatory signals (Krummey and Ford, 2014) on antigen presenting cells, but could additionally be dependent on the production of anti-inflammatory signals, actively inhibiting the pathogenic response (Linsley et al., 1991) (Sage et al., 2014). To further investigate this, we examined the presence of immune mediators via real-time qPCR in the treated TAC-operated animals. At 1 week post-operation, a timepoint when abatacept already leads to cardioprotective effects, mRNA expression for the pro-inflammatory cytokine IL-6 was significantly upregulated in both abatacept- and PBS-treated TAC-operated mice (FIG. 5d: il6). This is not surprising as both groups of animals underwent the same TAC treatment, where IL-6 has a central involvement in the stressed myocardium response (Melendez et al., 2010). However, only in the abatacept-treated group could we observe a significant upregulation of mRNA for the cytokine IL-10 (FIG. 5d: il10). Thus, abatacept did produce a significant upregulation of Il10 in TAC-operated mice (FIG. 5D; il10). IL-10 is one of the most potent anti-inflammatory cytokines utilized by the immune system to shut down unwanted or no-longer-needed responses and it has been shown to mediate cardio-protective effects in HF (Verma et al., 2012), its effect on cardiomyocyte function being opposite to that of IL-6 (Melendez et al., 2010). Administration of abatacept itself did not have any direct effects on neonatal cardiomyocytes since in vitro it did not affect their hypertrophic state. These findings, taken together, suggested that abatacept could be mediating anti-inflammatory and subsequent anti-hypertrophic effects via IL-10. As Il10 was upregulated in abatacept-treated TAC mice, we assessed which subset of immune cells could function as sources of IL-10. We examined the expression of intracellular IL-10 by flow cytometry in splenocytes exposed in vitro to abatacept. We found that abatacept induced IL-10 mostly on antigen-presenting cells, the vast majority of which were B cells, whilst a few IL-10 producing T cells could also be identified (FIG. 11B).

We thus examined whether IL-10 was necessary for the protective effects of abatacept. To address this, we analyzed the effect of abatacept on mice deficient for IL-10 (IL-10KO) subjected to TAC. As outlined above, the hallmark of abatacept function is the suppression of T cell responses. Interestingly, in IL-10KO mice abatacept could no longer inhibit T cell presence in the heart of TAC-operated mice (FIG. 6A), demonstrating that IL-10 is required for the T cell-attenuating, anti-inflammatory effect of the drug.

Figure 6F:
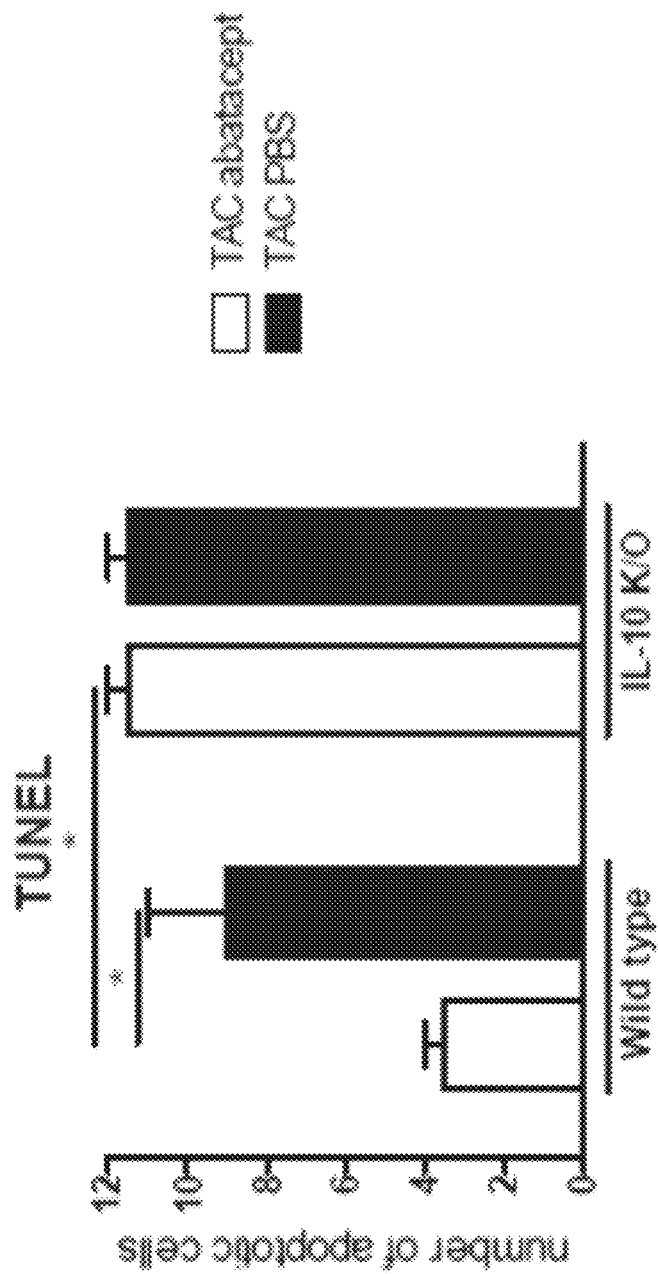
Figure 6H:
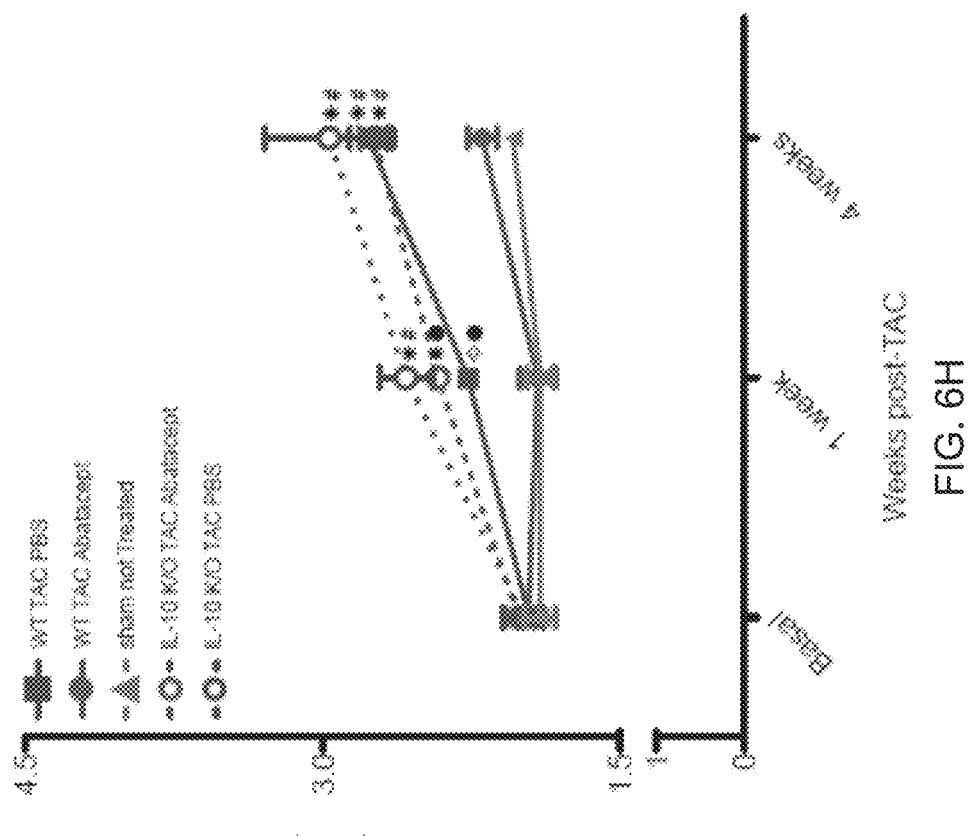

Subsequently, we asked whether IL-10 was necessary for the abatacept-mediated effects on cardiac hypertrophy. Echocardiographic analysis of TAC-operated, IL-10KO mice confirmed that IL-10 was required for the beneficial effect of abatacept on the heart (FIG. 6B-E). Finally, apoptosis of cardiomyocytes is a hallmark of pathological hypertrophy(Condorelli et al., 1999). Whilst abatacept significantly reduced the extent of cardiomyocyte apoptosis in wild-type TAC-operated mice, this did not occur in IL-10KO mice, which were refractive to treatment (FIG. 6F).

Our results, taken together, suggest that abatacept may protect against the progression of HF by removing and actively reversing the pathogenic immune response, consequently affecting cardiac hypertrophy, in a manner dependent on the cytokine IL-10. Calculating and plotting the heart dysfunction and inflammation indices (FIG. 7A,B) shows that abatacept leads to a reduction in inflammation (left-ward shift compared to PBS-treated mice), and consequently to an improvement of cardiac function, evaluated as a reduction in heart dysfunction (shift to lower values on the y axis). Cardiac function was improved also at 4 weeks post-TAC, indicating a delay in the progression of the syndrome (FIG. 7B).

Example 9

Figure 6G:
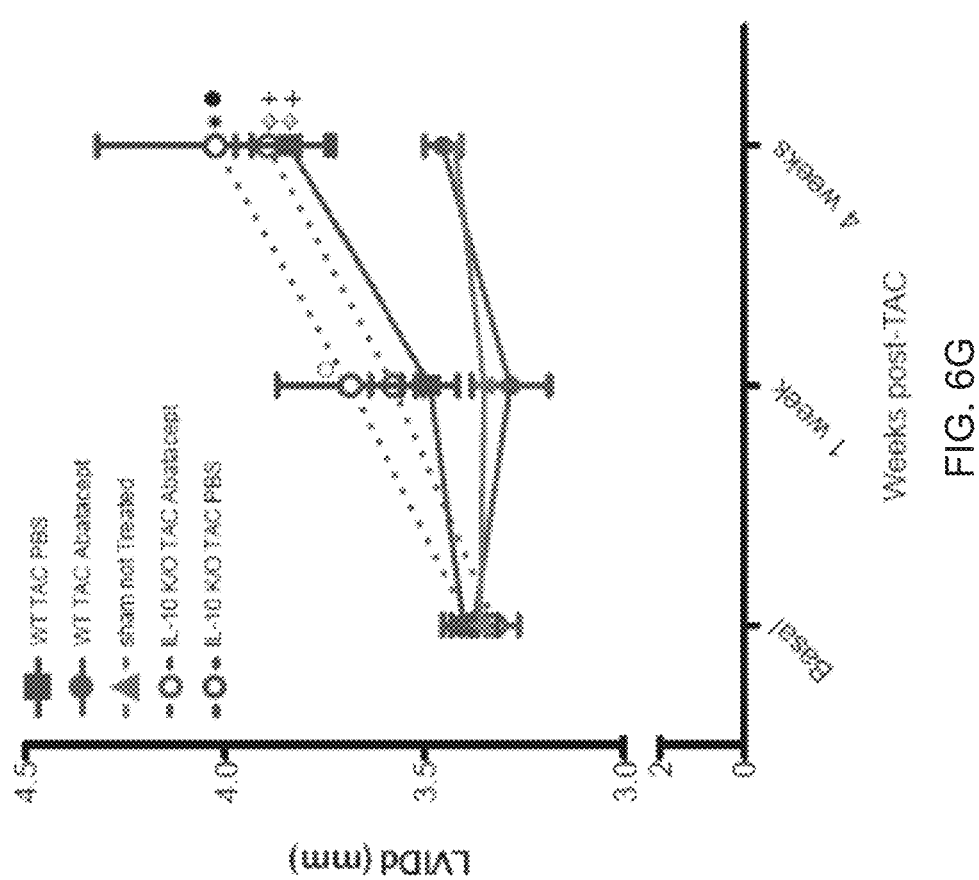

Provision of IL-10 Wild-Type B Cells is Sufficient to Rescue the Loss of the Abatacept-Mediated Protective Effect We then sought to confirm whether the IL-10 producing cells identified above (i.e. mostly B cells, and—to a lesser extent—T cells) could be sufficient to rescue the loss of the protective effect in IL-10KO animals. To achieve this, we first transferred $2 \cdot 10^6$ wild-type (IL-10-sufficient) B cells or $2 \cdot 10^6$ wild-type (IL-10 sufficient) T cells into IL-10KO recipients. We then proceeded to perform TAC surgery followed by abatacept or control treatment, starting from day 2 post-operation. Transfer of IL-10 wild-type B cells was sufficient to rescue the loss of the abatacept-mediated protective effect in IL-10KO TAC-operated mice (FIG. 6g,h: closed squares). On the other hand, transfer of IL10 wild-type T cells could not rescue the protective effect (FIG. 6g,h: open squares). From this we conclude that IL-10 produced by B cells in response to abatacept must be involved in the mechanism of the abatacept-mediated cardioprotective effect. To assess whether this B cell-mediated effect was dependent on the drug's effect on T cells or whether it could be a direct effect on B cells, we assessed the capacity of splenocytes to produce IL-10 after abatacept administration in vitro, in the presence or absence of T cells. We found that the production of IL-10 was unaffected by the absence of T cells (FIG. 16), suggesting that the B cell-mediated effect may be direct.

Our results, taken together, suggest that abatacept may protect against the progression of HF by inhibiting the pathogenic immune response mediated by T cells and macrophages, whilst also directly inducing the beneficial production of anti-inflammatory cytokine IL-10 by B cells.

Discussion

Inventors herein demonstrate how abatacept, an FDA-approved drug that inhibits T cell costimulation, reduces the severity and delays the progression of pressure overload-induced cardiac hypertrophy and fibrosis. This outcome was possible because inventors herein found out that HF pathogenesis is associated with an innate and adaptive immune response. Abatacept blunts this response, and hence inhibits the progression of cardiac pathology, via a mechanism dependent on the action of IL-10.

The cardiac inflammation associated with HF is believed to be triggered by pro-inflammatory cytokine secretion by stressed cardiomyocytes (Shioi et al., 1997,) (Ancey et al., 2002) (Souders et al., 2012). The presence of such cytokines has been used to distinguish between physiological and pathological hypertrophy (Serra et al., 2010). While confirming and extending knowledge of the association between inflammation and cardiac pathology, importantly, we show here that by targeting the cells of the adaptive immune system, it is possible to interfere with cardiac remodeling by blunting the inflammatory response. This is in contrast to unsuccessful attempts to limit pathology by targeting the cytokines, which have proven to be more elusive targets (Yndestad et al., 2006) (Hofmann and Frantz, 2013).

A main clinical feature of pathological cardiac hypertrophy is fibrosis. Fibrosis formation in other contexts appears to require the combined action of Th2-polarized T cells and innate immune cells (Wynn, 2004) (Niedermeier et al., 2009). We delineated how cardiac inflammation is initially mediated by M1-polarized innate immune cells and may subsequently switch to an M2/Th2 polarization as time progresses. This is in agreement with two previous studies reporting worse HF in BALB/c compared to C57BL/6 mice, attributable to a greater Th2-bias in the former strain (Yu et al., 2006) (Peng et al., 2011). We also demonstrated the presence of T cells in biopsies from human HF patients, from both patients with severe dilated cardiomyopathy derived from non-immunological causes, as well as from patients suffering from aortic stenosis.

One of the immune system's main means of regulating the action of T cells is via immunosuppressive regulatory T cells (Treg), which suppress deleterious or unwanted responses (Wing and Sakaguchi, 2010). Intriguingly, evidence has linked Treg deficiency with chronic HF (Tang et al., 2010). We detected the presence of Tregs, via the expression of their genetic marker Foxp3, in TAC mice, but only at 8 weeks post-surgery (FIG. 12). This may be an indication of a natural immunosuppressive attempt that occurs too late to block the pathogenic immune response (Garetto et al., 2015). There have been two successful experimental attempts to utilize syngenic Treg administration (Treg adoptive cell therapy) in models of HF (Kvakan et al., 2009) (Kanellakis et al., 2011). However, adoptive cell therapy, whilst very promising, is a complex and costly procedure that still needs refinement before it can move to clinical use. An alternative means of taking advantage of the suppressive function of Treg is to selectively activate them via super-activating anti-CD28 antibodies. This has been utilized twice in models of cardiac repair after myocardial infarction (MI) (Tang et al., 2012) (Weirather et al., 2014). Whilst MI-induced cardiac stress and its associated immune response have several key differences compared to pressure overload-induced HF, the success of these studies represents nonetheless an encouraging milestone. An important caveat of this approach, however, lies in the fact that human patients have far higher numbers of pro-inflammatory memory T cells, which in past clinical trials have been activated by super-activating anti-CD28 clones, with near-lethal consequences for the patients (Suntharalingam et al., 2006). Whilst this issue is being currently addressed with the use of more precise reagents (Weirather et al., 2014), this solution is not yet fully applicable in the clinic. Hence, searching for a more readily translatable solution, we chose to utilize a fusion protein based on CTLA-4, one of the effector molecules of Treg cells. Treg suppress via surface-bound CTLA-4 as well as soluble IL-10 or TGFβ, inhibiting the function of both innate and adaptive immune cells(Wing and Sakaguchi, 2010). CTLA-4 specifically inhibits T cell function by blocking the ability of T cells to become costimulated. The CTLA4-Ig fusion protein abatacept is easily administered and already in clinical use to suppress autoimmune responses (Moreland et al., 2006). As the drug is functional in mice, for our attempted therapy we chose to utilize the TAC mouse model of HF. The TAC model is considered the gold standard model of overload-induced HF and indeed it has been used in a very large number of studies on a wide range of conditions associated with HF.

Even though we did observe a systemic suppression of T cells evident even in non-draining lymphoid organs of abatacept-treated TAC-operated mice, the established clinical safety record of abatacept reduces the risk that this immunosuppressive treatment could expose the body to opportunistic infections.

We demonstrated that abatacept reduced the severity of cardiac pathology and delayed the development of symptoms of overload-derived cardiac pathology. Importantly, we were able to demonstrate that the drug could significantly limit the progression of pathology even when administration commenced at a late stage of disease.

The drug is known to inhibit T cell function by blocking costimulatory ligands CD80 and CD86 on antigen presenting cells (Moreland et al., 2006). Accordingly, we found that abatacept inhibited T cell responses in vivo (FIG. 5), including in heart-draining lymph nodes, where T cell activation appears to be initiated (FIG. 3e). We also observed an inhibition of cardiac macrophage activation and maturation (FIG. 5c,e,f). Inflammation in abatacept-treated mice was attenuated, affecting cardiac macrophage activation (FIG. 5C) as well as the balance of pro- versus anti- cytokine levels, as it can be readily visualized in the heart dysfunction versus inflammation plots (FIG. 7A,B). Abatacept also induced active anti-inflammatory signals, such as the cytokine IL-10, which we detected in vivo (FIG. 5D) and which could be produced by both T cells and antigen presenting cells (FIG. 11B). IL-10 (FIG. 6b-d) was necessary for the protective effects to occur and IL-10 could be produced by B cells after in vitro treatment with the drug (FIG. 11b). IL-10-sufficient B cells appeared to be sufficient to rescue the loss of cardioprotective effects in IL-10KO TAC-operated animals treated with abatacept (FIG. 6a-h). As T cells and antigen presenting cells co-operate for their mutual full activation (Linsley et al., 1991), it is not surprising that both populations may be involved in the induction of anti-inflammatory signals. The schematic outline of this combined removal of pro-inflammatory T cell activation and induction of anti-inflammatory signals (in B cells) is given in (FIG. 7C). As IL-10 has been shown to be directly cardioprotective and antifibrotic (Verma et al., 2012) (Wynn, 2004), the benefit conferred by abatacept treatment could be due to a combined effect of the removal of the pro-inflammatory signals, as well as direct protective effects of IL-10. Both these effects were dependent upon IL-10 because in mice deficient for the cytokine, abatacept treatment no longer suppressed T cell expansion nor protected from loss of cardiac functionality or cardiomyocyte apoptosis.

Although abatacept has been shown to induce regulatory T cells (Ko et al., 2010), we did not observe any significant induction of Foxp3 mRNA expression in our system. However, we did observe IL-10 production from Foxp3+ Treg cells in vitro following abatacept administration, so this parallel mechanism cannot be formally excluded. As cardiac macrophages, which we found to be suppressed by abatacept, can act as CD80/CD86-expressing antigen presenting cells, we also cannot exclude that the drug suppresses macrophages both via its effect on T cells, and also by acting directly on the macrophages themselves.

The treatment according to the invention targets the costimulation of T cells and thus their optimal activation. T cell activation may also be relevant for the chronicity of the underlying cardiac disease, and the continuous presence of cognate antigens recognized by T cells may stand in the way of resolution. As an example of an inhibitor of T cell costimulation and/or activation and/or function that is already in clinical use, CLTA4-derived molecules such as a CTLA4-Ig, e.g., Abatacept, may be more translationally relevant than other means of targeting T cells currently being explored for the treatment of pressure overload-induced HF. Further, costimulation requires interactions between T cells and antigen presenting cells. Therefore targeting costimulation requires the targeting of CD80/CD86-bearing macrophages and B cells, which contributes to the therapeutic effect, as it affects T cell-associated B cell and macrophage responses.

IL-10 is directly cardioprotective and antifibrotic. Our results showed that the presence of IL-10 was necessary for the cardioprotective effects of abatacept, and also for the suppression of T cell expansion (FIG. 6a). Yet IL-10 acts downstream of the administration of the drug. Thus the regulation of IL-10 induction will be dependent on localization and abundance of the targets of the drug. A T-cell costimulation inhibitor such as the CTLA4-Ig-type T cell inhibitor Abatacept, even when B cells and macrophages are its direct targets, affects only T cell-associated responses. Abatacept did affect T cell activation systemically (as shown in FIG. 5a) but, extrapolating from the data in autoimmune pathologies cited above, is predicted not to affect T cell-independent innate immune responses, even if its action is dependent on IL-10. The proven safety profile of Abatacept in the clinic offers substantial support to the interpretation that the balance of useful immunosuppression versus induction of functional immunodeficiency may be satisfactory in a CTLA4-based T cell inhibitory molecule such as a CTLA4-Ig, e.g., Abatacept.

Taken together, the findings of the present study demonstrate how an FDA-approved drug that inhibits pro-inflammatory T cell function can yield significant therapeutic benefits in a model of HF. The underlying reason for this is that an adaptive immune response is causatively linked to the pathogenesis of pressure overload-induced cardiac hypertrophy and fibrosis. As T cells contribute greatly to the chronicity of the immune response, their targeting seems to be efficacious in controlling the progression of the pathology.

The induction of an immune response as a reaction to cardiac pressure overload could be an unwanted consequence of a response originally evolved to deal with pathogen infections. It may be that the body is unable to distinguish between infection- and pressure overload-induced stress signals. Yet, fortuitously, this link between immunity and pathological cardiac hypertrophy also creates an opportunity: functional and validated therapies—currently in clinical use for treating immune-mediated ailments—could become an important tool in the fight against heart failure.

Thus, in summary, the inventors describe herein that an inhibitor of T cell costimulation and/or activation and/or function is effective in treating or preventing heart failure pathologies that are not induced by inflammatory cardiomyopathies caused by autoimmunity or by immune responses to infection (e.g.: not by viral infection). Pressure-overload induced heart failure is a representative example of the heart failure pathologies thus treated or prevented.

It will of course be understood that the present invention has been described above by way of example only and that modifications of detail can be made within the scope of the appended claims.

Tables

TABLE 1

Hemodynamic parameters of TAC- and sham-operated mice at 1, 3, and 4 weeks post-operation.

| | SHAM | | | | TAC | | | |
|---|---|---|---|---|---|---|---|---|
| | Basal (n = 3) | 1 week post-sham (n = 3) | 3 weeks post-sham (n = 3) | 4 weeks post-sham (n = 3) | Basal (n = 7) | 1 week post-TAC (n = 7) | 3 weeks post-TAC (n = 7) | 4 weeks post-TAC (n = 7) |
| Age | 8.7 ± 0.0 | 9.6 ± 0.1 | 11.7 ± 0.1 | 12.6 ± 0.0 | 8.6 ± 0.1 | 9.6 ± 0.1 | 11.6 ± 0.1 | 12.6 ± 0.0 |
| Weight | 22.0 ± 1.0 | 22.4 ± 0.8 | 23.6 ± 0.9 | 23.9 ± 1.1 | 22.8 ± 1.6 | 22.3 ± 1.3 | 24.0 ± 1.5 | 24.6 ± 1.5 |
| HR M-mode | 545.7 ± 71.1 | 507.7 ± 93.9 | 549.7 ± 66.0 | 598.0 ± 29.0 | 577.0 ± 66.4 | 530.1 ± 48.7 | 517.9 ± 87.1 | 606.0 ± 36.6 |
| % FS | 43.4 ± 3.1 | 43.3 ± 1.4 | 42.9 ± 3.0 | 40.3 ± 1.7 | 40.5 ± 2.4 | 37.7 ± 1.2$^{§†}$ | 33.2 ± 1.5$^{*§}$ | 30.6 ± 2.2$^{*§}$ |
| % EF | 75.7 ± 3.5 | 75.6 ± 1.5 | 75.0 ± 3.5 | 72.1 ± 2.1 | 72.3 ± 3.6 | 69.0 ± 1.6$^{§†}$ | 62.7 ± 2.1$^{*§}$ | 58.8 ± 3.5$^{*§}$ |
| LVIDd | 3.4 ± 0.1 | 3.4 ± 0.1 | 3.5 ± 0.1 | 3.4 ± 0.0 | 3.4 ± 0.1 | 3.4 ± 0.2 | 3.7 ± 0.1$^{°+}$ | 3.7 ± 0.3$^{†}$ |
| LVIDs | 1.9 ± 0.1 | 1.9 ± 0.1 | 2.0 ± 0.2 | 2.0 ± 0.1 | 2.0 ± 0.2 | 2.1 ± 0.1$^{°}$ | 2.5 ± 0.1$^{§*}$ | 2.6 ± 0.3$^{°*}$ |
| IVSd | 0.7 ± 0.0 | 0.8 ± 0.1 | 0.7 ± 0.1 | 0.8 ± 0.1 | 0.7 ± 0.0 | 0.9 ± 0.1$^{°*}$ | 0.9 ± 0.1$^{°*}$ | 1.0 ± 0.1$^{#*}$ |
| IVSs | 1.1 ± 0.1 | 1.2 ± 0.0 | 1.2 ± 0.1 | 1.2 ± 0.1 | 1.2 ± 0.1 | 1.3 ± 0.1$^{†}$ | 1.3 ± 0.1$^{°+}$ | 1.4 ± 0.1$^{°+}$ |
| LVPWd | 0.7 ± 0.1 | 0.8 ± 0.0 | 0.8 ± 0.1 | 0.8 ± 0.1 | 0.8 ± 0.1 | 0.9 ± 0.1 | 0.9 ± 0.1$^{#*}$ | 0.9 ± 0.1$^{†}$ |
| LVPWs | 1.2 ± 0.1 | 1.3 ± 0.0 | 1.2 ± 0.1 | 1.2 ± 0.1 | 1.2 ± 0.1 | 1.3 ± 0.1 | 1.3 ± 0.1$^{°+}$ | 1.3 ± 0.1$^{†}$ |

$^{°}$p < 0.05 TAC versus sham at the same time point
$^{#}$p < 0.01 TAC versus sham at the same time point
$^{§}$p < 0.001 TAC versus sham at same time point
$^{†}$p < 0.05 TAC basal versus TAC at each time point
$^{+}$p < 0.01 TAC basal versus TAC at each time point
$^{*}$p < 0.001 TAC basal versus TAC at each time point
Unpaired T-test

TABLE 2

Hemodynamic parameters of TAC- and sham-operated mice treated with abatacept or PBS at 1, 3, and 4 weeks post-operation.

| | SHAM | | | | | | | |
|---|---|---|---|---|---|---|---|---|
| | Abatacept | | | | PBS | | | |
| | Basal (n = 8) | 1 week post-sham (n = 7) | 3 weeks post-sham (n = 8) | 4 weeks post-sham (n = 8) | Basal (n = 8) | 1 week post-sham (n = 5) | 3 weeks post-sham (n = 7) | 4 weeks post-sham (n = 7) |
| Age (wks) | 9.0 ± 0.3 | 9.9 ± 0.0 | 12.0 ± 0.0 | 12.9 ± 0.0 | 9 ± 0.3 | 10.1 ± 0.0 | 12.0 ± 0.1 | 13.0 ± 0.0 |
| Weight (g) | 22.6 ± 1.4 | 22.1 ± 1.3 | 23.5 ± 1.5 | 23.7 ± 1.7 | 22.6 ± 1.4 | 21.7 ± 1.4 | 23.11 ± 2.1 | 24.0 ± 1.9 |
| HR M-mode (bpm) | 564.4 ± 75.8 | 514.0 ± 56.4 | 602.8 ± 68.6 | 614.4 ± 44.5 | 564.4 ± 75.8 | 579.0 ± 18.9 | 577.3 ± 69.9 | 575.2 ± 85.6 |
| % FS | 41.4 ± 3.8 | 43.0 ± 4.1 | 42.6 ± 1.5 | 40.7 ± 2.0 | 41.4 ± 3.8 | 43.3 ± 2.5 | 40.6 ± 2.5 | 41.4 ± 1.7 |
| % EF | 73.2 ± 4.8 | 75.2 ± 4.8 | 74.9 ± 1.6 | 72.8 ± 2.4 | 73.2 ± 4.8 | 75.8 ± 2.6 | 72.7 ± 3 | 73.8 ± 1.9 |
| LVIDd (mm) | 3.4 ± 0.1 | 3.3 ± 0.2 | 3.3 ± 0.2 | 3.2 ± 0.2 | 3.4 ± 0.1 | 3.1 ± 0.2 | 3.2 ± 0.1 | 3.1 ± 0.3 |
| LVIDs (mm) | 2 ± 0.2 | 1.9 ± 0.2 | 1.9 ± 0.1 | 1.9 ± 0.1 | 2.0 ± 0.2 | 1.8 ± 0.1 | 1.9 ± 0.1 | 1.8 ± 0.2 |
| IVSd (mm) | 0.8 ± 0.0 | 0.7 ± 0.1 | 0.8 ± 0.0 | 0.8 ± 0.1 | 0.8 ± 0.0 | 0.8 ± 0.1 | 0.8 ± 0.0 | 0.8 ± 0.1 |
| IVSs (mm) | 1.2 ± 0.1 | 1.2 ± 0.0 | 1.3 ± 0.0 | 1.2 ± 0.0 | 1.2 ± 0.1 | 1.3 ± 0.1 | 1.2 ± 0.1 | 1.2 ± 0.1 |
| LVPWd (mm) | 0.8 ± 0.1 | 0.8 ± 0.1 | 0.8 ± 0.1 | 0.8 ± 0.0 | 0.8 ± 0.1 | 0.8 ± 0.0 | 0.8 ± 0.1 | 0.9 ± 0.1 |
| LVPWs (mm) | 1.2 ± 0.0 | 1.3 ± 0.0 | 1.2 ± 0.1 | 1.2 ± 0.1 | 1.2 ± 0.0 | 1.2 ± 0.0 | 1.2 ± 0.0 | 1.2 ± 0.0 |

| | TAC | | | | | | | |
|---|---|---|---|---|---|---|---|---|
| | Abatacept | | | | PBS | | | |
| | Basal (n = 9) | 1 week post-TAC (n = 8) | 3 weeks post-TAC (n = 7) | 4 weeks post-TAC (n = 7) | Basal (n = 10) | 1 week post-TAC (n = 10) | 3 weeks post-TAC (n = 10) | 4 weeks post-TAC (n = 10) |
| Age (wks) | 8.9 ± 0.0 | 9.9 ± 0.0 | 11.9 ± 0.0 | 12.9 ± 0.0 | 9.0 ± 0.3 | 10.1 ± 0.0 | 12.1 ± 0.0 | 12.9 ± 0.0 |
| Weight (g) | 22.5 ± 1.6 | 22.1 ± 1.4 | 23.4 ± 1.3 | 24 ± 1.8 | 22.6 ± 1.4 | 21.6 ± 1.8 | 23.6 ± 1.6 | 24.2 ± 1.4 |
| HR M-mode (bpm) | 556.9 ± 86.1 | 546.6 ± 55.8 | 597.9 ± 94.6 | 561.4 ± 66.0 | 564.4 ± 75.8 | 544.7 ± 46.2 | 575.2 ± 85.6 | 558.3 ± 60.9 |
| % FS | 42.0 ± 1.5 | 41.3 ± 3.2$^{#}$ | 37.3 ± 1.6$^{#+}$ | 36.5 ± 3.7$^{#}$ | 41.4 ± 3.8 | 34.9 ± 1.3$^{§}$ | 30.7 ± 3.0$^{§}$ | 27.5 ± 3.8$^{§}$ |
| % EF | 74.1 ± 1.8 | 73.4 ± 3.9$^{#}$ | 68.3 ± 2.2$^{#§}$ | 67.2 ± 4.8$^{#}$ | 73.2 ± 4.8 | 65.2 ± 1.8$^{§}$ | 58.9 ± 4.6$^{§}$ | 53.9 ± 6.2$^{§}$ |

TABLE 2-continued

| | | | | | | | | |
|---|---|---|---|---|---|---|---|---|
| LVIDd (mm) | 3.4 ± 0.1 | 3.3 ± 0.2 | 3.5 ± 0.2$^{\dagger\circ}$ | 3.5 ± 0.1$^{\#}$ | 3.4 ± 0.1 | 3.5 ± 0.2$^{+}$ | 3.8 ± 0.3$^{\S}$ | 3.8 ± 0.2$^{\S}$ |
| LVIDs (mm) | 1.9 ± 0.1 | 1.9 ± 0.2 | 2.2 ± 0.2 | 2.2 ± 0.2 | 2.0 ± 0.2 | 2.3 ± 0.1 | 2.6 ± 0.3 | 2.8 ± 0.3 |
| IVSd (mm) | 0.8 ± 0.1 | 0.9 ± 0.1$^{\S}$ | 0.9 ± 0.1$^{\circ}$ | 1.0 ± 0.0$^{\S}$ | 0.8 ± 0.0 | 0.9 ± 0.1 | 0.9 ± 0.1$^{+}$ | 1.0 ± 0.1$^{\S}$ |
| IVSs (mm) | 1.2 ± 0.1 | 1.3 ± 0.0$^{\S}$ | 1.3 ± 0.1 | 1.4 ± 0.0$^{\S}$ | 1.2 ± 0.1 | 1.3 ± 0.1 | 1.4 ± 0.1$^{\circ}$ | 1.3 ± 0.1 |
| LVPWd (mm) | 0.7 ± 0.1 | 0.9 ± 0.1 | 1 ± 0.1$^{\S}$ | 0.9 ± 0.0$^{\S}$ | 0.8 ± 0.1 | 0.9 ± 0.1$^{\S}$ | 1.0 ± 0.1$^{\S}$ | 1.0 ± 0.1$^{+}$ |
| LVPWs (mm) | 1.2 ± 0.1 | 1.4 ± 0.1 | 1.4 ± 0.1 | 1.4 ± 0.0 | 1.2 ± 0.0 | 1.4 ± 0.1 | 1.4 ± 0.0 | 1.4 ± 0.1 |

$^{\circ}$p < 0.05 TAC Abatacept/PBS versus sham Abatacept/PBS at the same time point
$^{+}$p < 0.01 TAC Abatacept/PBS versus sham Abatacept/PBS at the same time point
$^{\S}$p < 0.001 TAC Abatacept/PBS versus sham Abatacept/PBS at the same time point
$^{\dagger}$p < 0.05 TAC Abatacept versus TAC PBS at the same time point
$^{*}$p < 0.01 TAC Abatacept versus TAC PBS at the same time point
$^{\#}$p < 0.001 TAC Abatacept versus TAC PBS at the same time point

TABLE 3

List of primers used.

| Gene | Forward primer | Reverse primer |
|---|---|---|
| β-Myosin (Mhy7) | 5'-CGCATCAAGGAGCTCACC-3' (SEQ ID NO: 3) | 5'-CTGCAGCCGCAGTAGGTT-3' (SEQ ID NO: 4) |
| Brain Natriuretic Peptide (Nppb) | 5'-GTCAGTCGTTTGGGCTGTAAC-3' (SEQ ID NO: 5) | 5'-AGACCCAGGCAGAGTCAGAA-3' (SEQ ID NO: 6) |
| Atrial Natriuretic Peptide (Nppa) | 5'-CACAGATCTGATGGATTTCAAGA-3' (SEQ ID NO: 7) | 5'-CCTCATCTTCTACCGGCATC-3' (SEQ ID NO: 8) |
| 18S RNA (18S) | 5'-AAATCAGTTATGGTTCCTTTGGTC-3' (SEQ ID NO: 9) | 5'-GCTCTAGAATTACCACAGTTATCCAA-3' (SEQ ID NO: 10) |

The present disclosure also includes the following items:

1. An inhibitor of T cell costimulation and/or activation and/or function for use in the treatment and/or prevention of cardiac pathologies, preferably heart failure diseases, and/or of related symptoms.

2. The inhibitor for use according to item 1 being an inhibitor of at least one molecule promoting T cell costimulation.

3. The inhibitor for use according to item 1 or 2, wherein said inhibitor increases IL-10 levels in the heart.

4. The inhibitor for use according to any one of the previous items comprising or consisting of at least one molecule selected from the group consisting of: CTLA4, PD-1, PD-L1 or PD-L2, BTLA, CD160, LAG-3, 2B4, B7-H3, B7-H4, B7S3, BTNL2, blocking anti-CD28 antibodies, a functional fragment, a functional derivative or a functional analogues thereof.

5. The inhibitor for use according to item 2, wherein the molecule promoting T cell costimulation is selected from the group consisting of: B7-1 and B7-2 (also known as CD80 and CD86), CD40, CD40L (also known as CD154), OX40, OX40L, CD30, CD30L, 4-1BB, 4-BBL, GITR, GITR ligand, LIGHT, CD27, CD45RB, CD2, LFA-3, B7-H3, B7-H4, ICOS and ICOS ligands.

6. The inhibitor for use according to any one of previous items being at least one molecule selected from the group consisting of: blocking antibody or functional fragment thereof, or small molecule inhibitor or polynucleotide.

7. The inhibitor for use according to any one of items 1-3 being a molecule comprising or consisting of CTLA4 or a functional fragment or a functional derivative or a functional analogue thereof.

8. The inhibitor for use according to item 7 being a CTLA4-Ig molecule or a functional fragment or a functional derivative thereof or a functional analogue thereof 9. The inhibitor for use according to item 8, wherein the CTLA4-Ig molecule is a fusion protein comprising a first amino acid sequence containing amino acid residues corresponding to the extracellular domain of CTLA4 and a second amino acid sequence containing the Fc region of the Immunoglobulin IgG1.

10. The inhibitor for use according to item 8 or 9 wherein the CTLA4-Ig molecule comprises or essentially consists of the amino acid sequence of SEQ ID NO: 1, or a functional fragment or a functional derivative thereof or a functional analogue thereof.

11. The inhibitor for use according to any one of the previous items, wherein said inhibitor is Abatacept.

12. A nucleic acid molecule encoding for the inhibitor as defined in any one of items 1-11, for use in the treatment and/or prevention of cardiac pathologies, preferably heart failure diseases, and/or of related symptoms.

13. An expression vector comprising the nucleic acid as defined in item 12 or encoding for the inhibitor as defined in any one of items 1-11, for use in the treatment and/or prevention of cardiac pathologies, preferably heart failure diseases, and/or of related symptoms.

14. A genetically engineered host cell or nanoparticle or microvesicle which expresses the inhibitor as defined in any one of items 1-11, for use in the treatment and/or prevention of cardiac pathologies, preferably heart failure diseases, and/or of related symptoms.

15. A pharmaceutical composition comprising the inhibitor as defined in any one of items 1-11, or the nucleic acid molecule as defined in item 12, or the expression vector as defined in item 13, or the genetically engineered host cell or nanoparticle or microvesicle as defined in item 14, and at least one pharmaceutically acceptable carrier, for use in the treatment and/or prevention of cardiac pathologies, preferably heart failure diseases, and/or of related symptoms.

REFERENCES

Ancey, C., P. Corbi, J. Froger, A. Delwail, J. Wijdenes, H. Gascan, D. Potreau, and J. C. Lecron.

2002. Secretion of IL-6, IL-11 and LIF by human cardiomyocytes in primary culture. Cytokine. 18:199-205.

Bluestone, J. A. 1997. Is CTLA-4 a master switch for peripheral T cell tolerance? J Immunol. 158:1989-1993.

Bulut, D., G. Creutzenberg, and A. Mugge. 2012. The number of regulatory T cells correlates with hemodynamic improvement in patients with inflammatory dilated cardiomyopathy after immunoadsorption therapy. Scand J Immunol. 77:54-61. doi:10.1111/sji.12000.

Condorelli, G., A. Drusco, G. Stassi, A. Bellacosa, R. Roncarati, G. Iaccarino, M. A. Russo, Y. Gu, N. Dalton, C. Chung, M. V. Latronico, C. Napoli, J. Sadoshima, C. M. Croce, and J. J. Ross.

2002. Akt induces enhanced myocardial contractility and cell size in vivo in transgenic mice. Proc Natl Acad Sci USA. 99:12333-12338. doi:10.1073/pnas.172376399.

Condorelli, G., C. Morisco, G. Stassi, A. Notte, F. Farina, G. Sgaramella, A. de Rienzo, R. Roncarati, B. Trimarco, and G. Lembo. 1999. Increased cardiomyocyte apoptosis and changes in proapoptotic and antiapoptotic genes bax and bcl-2 during left ventricular adaptations to chronic pressure overload in the rat. Circulation. 99:3071-3078.

Condorelli, G., R. Roncarati, J. Ross, A. Pisani, G. Stassi, M. Todaro, S. Trocha, A. Drusco, Y. Gu, M. A. Russo, G. Frati, S. P. Jones, D. J. Lefer, C. Napoli, and C. M. Croce.

2001. Heart-targeted overexpression of caspase3 in mice increases infarct size and depresses cardiac function. Proc Natl Acad Sci USA. 98:9977-9982. doi:10.1073/pnas.161120198.

Dhirapong, A., G. X. Yang, S. Nadler, W. Zhang, K. Tsuneyama, P. Leung, S. Knechtle, A. A. Ansari, R. L. Coppel, F. T. Liu, X. S. He, and M. E. Gershwin. 2013. Therapeutic effect of cytotoxic T lymphocyte antigen 4/immunoglobulin on a murine model of primary biliary cirrhosis. Hepatology. 57:708-715. doi: 10.1002/hep.26067.

Epelman, S., K. J. Lavine, A. E. Beaudin, D. K. Sojka, J. A. Carrero, B. Calderon, T. Brija, E. L.

Gautier, S. Ivanov, A. T. Satpathy, J. D. Schilling, R. Schwendener, I. Sergin, B. Razani, E. C.

Forsberg, W. M. Yokoyama, E. R. Unanue, M. Colonna, G. J. Randolph, and D. L. Mann. 2014.

Embryonic and adult-derived resident cardiac macrophages are maintained through distinct mechanisms at steady state and during inflammation. Immunity. 40:91-104. doi: 10.1016/j.immuni.2013.11.019.

Garetto, S., A. E. Trovato, A. Lleo, F. Sala, E. Martini, A. G. Betz, G. D. Norata, P. Invernizzi, and M. Kallikourdis. 2015. Peak inflammation in atherosclerosis, primary biliary cirrhosis and autoimmune arthritis is counter-intuitively associated with regulatory T cell enrichment. Immunobiology. 220:1025-9. doi:10.1016/j.imbio.2015.02.006.

Hofmann, U., and S. Frantz. 2013. How can we cure a heart "in flame"? A translational view on inflammation in heart failure. Basic Res Cardiol. 108:356. doi:10.1007/s00395-013-0356-y.

Kanellakis, P., T. N. Dinh, A. Agrotis, and A. Bobik. 2011. CD4+CD25+Foxp330 regulatory T cells suppress cardiac fibrosis in the hypertensive heart. J Hypertens. 29:1820-1828

Kemi, O. J., M. Ceci, U. Wisloff, S. Grimaldi, P. Gallo, G.L. Smith, G. Condorelli, and O. Ellingsen. 2008. Activation or inactivation of cardiac Akt/mTOR signaling diverges physiological from pathological hypertrophy. J Cell Physiol. 214:316-321. doi:10.1002/jcp.21197.

Ko, H. J., M. L. Cho, S. Y. Lee, H. J. Oh, Y. J. Heo, Y. M. Moon, C. M. Kang, S. K. Kwok, J. H. Ju, S. H. Park, K. S. Park, and H. Y. Kim. 2010. CTLA4-Ig modifies dendritic cells from mice with collagen-induced arthritis to increase the CD4+CD25+Foxp3+ regulatory T cell population. J Autoimmun. 34:111-120. doi:10.1016/j.jaut.2009.07.006.

Kong, P., P. Christia, and N. G. Frangogiannis. 2014. The pathogenesis of cardiac fibrosis. Cell Mol Life Sci. 71:549-574. doi:10.1007/s00018-013-1349-6.

Krummey, S. M., and M. L. Ford. 2014. Braking bad: novel mechanisms of ctla-4 inhibition of T cell responses. Am J Transplant. 14:2685-2690. doi:10.1111/ajt.12938.

Kuang, S. Q., L. Geng, S. K. Prakash, J. M. Cao, S. Guo, C. Villamizar, C. S. Kwartler, A. M. Peters, A. R. Brasier, and D. M. Milewicz. 2013. Aortic remodeling after transverse aortic constriction in mice is attenuated with AT1 receptor blockade. Arterioscler Thromb Vasc Biol. 33:2172- 2179. doi:10.1161/ATVBAHA.113.301624.

Kvakan, H., M. Kleinewietfeld, F. Qadri, J. K. Park, R. Fischer, I. Schwarz, H. P. Rahn, R. Plehm, M. Wellner, S. Elitok, P. Gratze, R. Dechend, F. C. Luft, and D. N. Muller. 2009. Regulatory T cells ameliorate angiotensin II-induced cardiac damage. Circulation. 119:2904-2912. doi:10.1161/CIRCULATIONAHA.108.832782.

Lai, N. C., M. H. Gao, E. Tang, R. Tang, T. Guo, N. D. Dalton, A. Deng, and T. Tang. 2012. Pressure overload-induced cardiac remodeling and dysfunction in the absence of interleukin 6 in mice. Lab Invest. 92:1518-1526. doi:10.1038/labinvest.2012.97.

Linsley, P. S., W. Brady, M. Urnes, L. S. Grosmaire, N. K. Damle, and J. A. Ledbetter. 1991. CTLA-4 is a second receptor for the B cell activation antigen B7. J Exp Med. 174:561-569.

Loke, P., I. Gallagher, M. G. Nair, X. Zang, F. Brombacher, M. Mohrs, J. P. Allison, and J. E. Allen. 2007. Alternative activation is an innate response to injury that requires CD4+ T cells to be sustained during chronic infection. J Immunol. 179:3926-3936.

Mann, D. L. 2002. Inflammatory mediators and the failing heart: past, present, and the foreseeable future. Circ Res. 91:988-998.

Mantovani, A., A. Sica, S. Sozzani, P. Allavena, A. Vecchi, and M. Locati. 2004. The chemokine system in diverse forms of macrophage activation and polarization. Trends Immunol. 25:677- 686. doi:10.1016/j.it.2004.09.015.

Melendez, G. C., J. L. McLarty, S. P. Levick, Y. Du, J. S. Janicki, and G. L. Brower. 2010. Interleukin 6 mediates myocardial fibrosis, concentric hypertrophy, and diastolic dysfunction in rats. Hypertension. 56:225-231. doi: 10.1161/HYPERTENSIONAHA.109.148635.

Moreland, L., G. Bate, and P. Kirkpatrick. 2006. Abatacept. Nat Rev Drug Discov. 5:185-186. doi:10.1038/nrd1989.

Niedermeier, M., B. Reich, M. Rodriguez Gomez, A. Denzel, K. Schmidbauer, N. Gobel, Y. Talke, F. Schweda, and M. Mack. 2009. CD4+ T cells control the differentiation of Grl+ monocytes into fibrocytes. Proc Natl Acad Sci USA. 106:17892-17897. doi:10.1073/pnas.0906070106.

Oka, T., S. Hikoso, O. Yamaguchi, M. Taneike, T. Takeda, T. Tamai, J. Oyabu, T. Murakawa, H. Nakayama, K. Nishida, S. Akira, A. Yamamoto, I. Komuro, and K. Otsu.

2012. Mitochondrial DNA that escapes from autophagy causes inflammation and heart failure. Nature. 485:251-255. doi:10.1038/nature10992.

Peng, H., X. P. Yang, O. A. Carretero, P. Nakagawa, M. D'Ambrosio, P. Leung, J. Xu, E. L. Peterson, G. E. Gonzalez, P. Harding, and N. E. Rhaleb. 2011. Angiotensin II-induced dilated cardiomyopathy in Balb/c but not C57BL/6J mice. Exp Physiol. 96:756-764. doi: 10.1113/expphysiol.2011.057612.

Perrino, C., S. V. Naga Prasad, L. Mao, T. Noma, Z. Yan, H. S. Kim, O. Smithies, and H. A. Rockman. 2006. Intermittent pressure overload triggers hypertrophy-independent cardiac dysfunction and vascular rarefaction. J Clin Invest. 116:1547-1560. doi:10.1172/JCI25397.

Pilat, N, C Schwarz, and T Wekerle (2012), 'Modulating T-cell costimulation as new immunosuppressive concept in organ transplantation.', *Curr Opin Organ Transplant*, 17 (4), 368-75.

Roncarati, R., C. Viviani Anselmi, P. Krawitz, G. Lattanzi, Y. von Kodolitsch, A. Perrot, E. di Pasquale, L. Papa, P. Portararo, M. Columbaro, A. Forni, G. Faggian, G. Condorelli, and P. N. Robinson. 2013. Doubly heterozygous LMNA and TTN mutations revealed by exome sequencing in a severe form of dilated cardiomyopathy. Eur J Hum Genet. 21:1105-1111. doi:10.1038/ejhg.2013.16.

Sage, P. T., A. M. Paterson, S. B. Lovitch, and A. H. Sharpe. 2014. The coinhibitory receptor CTLA-4 controls B cell responses by modulating T follicular helper, T follicular regulatory, and T regulatory cells. Immunity. 41:1026-1039. doi:10.1016/j.immuni.2014.12.005.

Serra, A. J., M. H. Santos, D. S. Bocalini, E. L. Antonio, R. F. Levy, A. A. Santos, M. L. Higuchi, J. A. Silva, F. C. Magalhaes, V. G. Barauna, J. E. Krieger, and P. J. Tucci. 2010. Exercise training inhibits inflammatory cytokines and more than prevents myocardial dysfunction in rats with sustained beta-adrenergic hyperactivity. J Physiol. 588:2431-2442. doi:10.1113/jphysiol.2010.187310.

Sharpe, A H (2009), 'Mechanisms of costimulation.', *Immunol Rev*, 229 (1), 5-11.

Shioi, T., A. Matsumori, Y. Kihara, M. Inoko, K. Ono, Y. Iwanaga, T. Yamada, A. Iwasaki, K. Matsushima, and S. Sasayama. 1997. Increased expression of interleukin-1 beta and monocyte chemotactic and activating factor/monocyte chemoattractant protein-1 in the hypertrophied and failing heart with pressure overload. Circ Res. 81:664-671.

Souders, C. A., T. K. Borg, I. Banerjee, and T. A. Baudino. 2012. Pressure overload induces early morphological changes in the heart. Am J Pathol. 181:1226-1235. doi: 10.1016/j.ajpath.2012.06.015.

Stolen, T. O., M. A. Hoydal, O. J. Kemi, D. Catalucci, M. Ceci, E. Aasum, T. Larsen, N. Rolim, G. Condorelli, G. L. Smith, and U. Wisloff. 2009. Interval training normalizes cardiomyocyte function, diastolic Ca2+ control, and SR Ca2+ release synchronicity in a mouse model of diabetic cardiomyopathy. Circ Res. 105:527-536. doi:10.1161/CIRCRESAHA.109.199810.

Suntharalingam, G., M. R. Perry, S. Ward, S. J. Brett, A. Castello-Cortes, M. D. Brunner, and N. Panoskaltsis. 2006. Cytokine storm in a phase 1 trial of the anti-CD28 monoclonal antibody TGN1412. N Engl J Med. 355: 1018-1028. doi:10.1056/NEJMoa063842.

Tang, T. T., Y. J. Ding, Y. H. Liao, X. Yu, H. Xiao, J. J. Xie, J. Yuan, Z. H. Zhou, M. Y. Liao, R. Yao, Y. Cheng, and X. Cheng. 2010. Defective circulating CD4CD25+Foxp3+CD127(low) regulatory T-cells in patients with chronic heart failure. Cell Physiol Biochem. 25:451-458. doi: 10.1159/000303050.

Tang, T. T., J. Yuan, Z. F. Zhu, W. C. Zhang, H. Xiao, N. Xia, X. X. Yan, S. F. Nie, J. Liu, S. F. Zhou, J. J. Li, R. Yao, M. Y. Liao, X. Tu, Y. H. Liao, and X. Cheng. 2012. Regulatory T cells ameliorate cardiac remodeling after myocardial infarction. Basic Res Cardiol. 107:232. doi: 10.1007/s00395-011-0232-6.

Tian, Y., S. E. Kelemen, and M. V. Autieri. 2006. Inhibition of AIF-1 expression by constitutive siRNA expression reduces macrophage migration, proliferation, and signal transduction initiated by atherogenic stimuli. Am J Physiol Cell Physiol. 290:C1083-91. doi:10.1152/ajpcell.00381.2005.

Utans, U., R. J. Arceci, Y. Yamashita, and M. E. Russell. 1995. Cloning and characterization of allograft inflammatory factor-1: a novel macrophage factor identified in rat cardiac allografts with chronic rejection. J Clin Invest. 95:2954-2962. doi:10.1172/JCI118003.

Verma, S. K., P. Krishnamurthy, D. Barefield, N. Singh, R. Gupta, E. Lambers, M. Thal, A. Mackie, E. Hoxha, V. Ramirez, G. Qin, S. Sadayappan, A. K. Ghosh, and R. Kishore. 2012. Interleukin-10 treatment attenuates pressure overload-induced hypertrophic remodeling and improves heart function via signal transducers and activators of transcription 3-dependent inhibition of nuclear factor-kappaB. Circulation. 126:418-429. doi:10.1161/CIRCULATIONAHA.112.112185.

Weirather, J., U. Hofmann, N. Beyersdorf, G. C. Ramos, B. Vogel, A. Frey, G. Ertl, T. Kerkau, and S. Frantz. 2014. Foxp3+CD4+ T Cells Improve Healing after Myocardial Infarction by Modulating Monocyte/Macrophage Differentiation. Circ Res. 115:55-67. doi:10.1161/CIRCRESAHA.115.303895.

Wing, K., and S. Sakaguchi. 2010. Regulatory T cells exert checks and balances on self tolerance and autoimmunity. Nat Immunol. 11:7-13

Wynn, T. A. 2004. Fibrotic disease and the T(H)1/T(H)2 paradigm. Nat Rev Immunol. 4:583 594. doi:10.1038/nri1412.

Xia, Y., K. Lee, N. Li, D. Corbett, L. Mendoza, and N. G. Frangogiannis. 2009. Characterization of the inflammatory and fibrotic response in a mouse model of cardiac pressure overload. Histochem Cell Biol. 131:471-481. doi:10.1007/s00418-008-0541-5.

Yndestad, A., J. K. Damas, E. Oie, T. Ueland, L. Gullestad, and P. Aukrust. 2006. Systemic inflammation in heart failure—the whys and wherefores. Heart Fail Rev. 11:83-92. doi:10.1007/s10741-006-9196-2.

Yu, Q., K. Horak, and D. F. Larson. 2006. Role of T lymphocytes in hypertension-induced cardiac extracellular matrix remodeling. Hypertension. 48:98-104. doi: 10.1161/01.HYP.0000227247.27111.b2.

Zarrinkoub, R., B. Wettermark, P. Wandell, M. Mejhert, R. Szulkin, G. Ljunggren, and T. Kahan. 2013. The epidemiology of heart failure, based on data for 2.1 million inhabitants in Sweden. Eur J Heart Fail. 15:995-1002. doi:10.1093/eurjhf/hft064.

The invention claimed is:

1. A method of treating or preventing pressure overload-induced heart failure comprising a step of inhibiting T cell costimulation and/or activation,
wherein the step of inhibiting is carried out by administration of an inhibitor,
wherein the inhibitor comprises a CTLA4 extracellular domain which binds CD80 and/or CD86.

2. The method of claim 1, wherein the pressure overload-induced heart failure comprises cardiac hypertrophy and fibrosis.

3. The method of claim 1, wherein the inhibitor is an inhibitor of T cell costimulation.

4. The method of claim 1, wherein the inhibitor increases IL-10 levels in the heart.

5. The method of claim 1, wherein the inhibitor inhibits the costimulatory function of CD80 and/or CD86.

6. The method of claim 1, wherein the CTLA4 extracellular domain has at least 85% sequence identity to amino acids 1-125 of SEQ ID NO: 1.

7. The method of claim 1, wherein the inhibitor is a CTLA4-Ig molecule which binds CD80 and/or CD86.

8. The method of claim 1, wherein the inhibitor has at least 85% sequence identity to SEQ ID NO:1.

9. The method of claim 1, wherein the inhibitor comprises amino acids 1-125 of SEQ ID NO: 1.

10. The method of claim 1, wherein the inhibitor comprises the amino acid sequence SEQ ID NO: 1.

11. The method of claim 1, wherein the inhibitor is Abatacept.

12. The method of claim 1, wherein pressure overload-induced cardiac hypertrophy and fibrosis are treated and/or prevented.

13. The method of claim 1, wherein the heart failure is of New York Heart Association Class III or IV, or of stage C or D according to the classification by the American College of Cardiology and the American Heart Association.

14. The method of claim 1, wherein the heart failure is of New York Heart Association Class I or II, or of stage A or B according to the classification by the American College of Cardiology and the American Heart Association.

15. The method of claim 1, wherein a nucleic acid molecule encoding the inhibitor is administered.

16. The method of claim 15, wherein the nucleic acid molecule is comprised in an expression vector.

17. The method of claim 1, wherein the inhibitor is administered as a pharmaceutical composition comprising the inhibitor and at least one pharmaceutically acceptable carrier.

* * * * *